(12) United States Patent
Hsieh et al.

(10) Patent No.: US 8,507,502 B2
(45) Date of Patent: Aug. 13, 2013

(54) FUSED BICYCLIC AND TRICYCLIC PYRIMIDINE COMPOUNDS AS TYROSINE KINASE INHIBITORS

(75) Inventors: Hsing-Pang Hsieh, Miaoli County (TW); Selvaraj Mohane Coumar, Pondicherry (IN); Tsu-An Hsu, Miaoli County (TW); Wen-Hsing Lin, Miaoli County (TW); Yi-Rong Chen, Miaoli County (TW); Yu-Sheng Chao, Monmouth Junction, NJ (US)

(73) Assignee: National Health Research Institutes, Miaoli County (TW)

( * ) Notice: Subject to any disclaimer, the term of this patent is extended or adjusted under 35 U.S.C. 154(b) by 726 days.

(21) Appl. No.: 12/614,584

(22) Filed: Nov. 9, 2009

(65) Prior Publication Data

US 2010/0120805 A1 May 13, 2010

Related U.S. Application Data

(60) Provisional application No. 61/112,865, filed on Nov. 10, 2008.

(51) Int. Cl.
C07D 487/04 (2006.01)
A61K 31/519 (2006.01)
A61P 35/00 (2006.01)

(52) U.S. Cl.
USPC ........ 514/260.1; 544/278; 544/250; 544/293; 544/277; 544/255; 514/267; 514/266.3; 514/266.4

(58) Field of Classification Search
USPC ...................................... 544/278; 514/260.1
See application file for complete search history.

(56) References Cited

U.S. PATENT DOCUMENTS

| | | | |
|---|---|---|---|
| 2005/0148562 A1 | 7/2005 | Pairet et al. | |
| 2005/0239778 A1 | 10/2005 | Konetzki et al. | |
| 2007/0037781 A1 | 2/2007 | Konetzki et al. | |

FOREIGN PATENT DOCUMENTS

| | | |
|---|---|---|
| WO | 95-19774 | 7/1995 |
| WO | WO9616960 | 6/1996 |
| WO | WO97/02266 | 1/1997 |
| WO | WO97/38983 | 10/1997 |
| WO | WO97/49689 | 12/1997 |
| WO | 98-02437 | 1/1998 |
| WO | WO9802437 | 1/1998 |
| WO | WO00/51991 | 9/2000 |
| WO | WO00/78735 | 12/2000 |
| WO | WO01/49688 | 7/2001 |
| WO | WO01/77104 | 10/2001 |
| WO | WO02/18370 | 3/2002 |
| WO | WO02/18373 | 3/2002 |
| WO | WO02/18375 | 3/2002 |
| WO | WO02/18376 | 3/2002 |
| WO | WO02/050043 | 7/2002 |
| WO | WO03/066060 | 8/2003 |
| WO | WO03/068264 | 8/2003 |
| WO | WO03/094921 | 11/2003 |
| WO | WO2004/004775 | 1/2004 |
| WO | WO2005/011701 | 2/2005 |
| WO | WO2005/065687 | 7/2005 |
| WO | WO2005/067546 | 7/2005 |
| WO | WO2006/015775 | 2/2006 |
| WO | WO2006/082129 | 8/2006 |
| WO | WO2007/003554 | 1/2007 |
| WO | WO2007/054551 | 5/2007 |
| WO | WO2007/056208 | 5/2007 |
| WO | WO2007/109279 | 9/2007 |
| WO | WO2008/006287 | 1/2008 |
| WO | WO2009/033581 | 3/2009 |

OTHER PUBLICATIONS

Foloppe et al., "Structure-Based Design of Novel Chk1 Inhibitors: Insights into Hydrogen Bonding and Protein-Ligand Affinity," J. Med. Chem., 48:4332-4345 (2005).
Bridges et al., "Enantioselective Inhibition of the Epidermal Growth Factor Receptor Tyrosine Kinase by 4-(α-Phenethylamino)quinazolines," Bioorganic & Medicinal Chemistry 3(12):1651-1656 (1995).
Salomon et al., "Epidermal Growth Factor-Related Peptides and Their Receptors in Human Malignancies," Critical Review in Oncology/Hematology, 19:183-232 (1995).
Munchhof et al., "Design and SAR of thienopyrimidine and thienopyridine inhibitors of VEGFR-2 kinase activity," Bioorganic & Medicinal Chemistry Letters 14:21-24 (2004).
Uberall et al., "The Status and Role of ErbB Receptors in Human Cancer," Experimental and Molecular Pathology, 84:79-89 (2008).
Yoon et al., "Efficient Synthesis of 4-Aminoquinazoline and Thieno[3,2-d]pyrimidin-4-ylamine Derivatives by Microwave Irridation," Organic Letters, 6(25):4775-4778 (2004).
Lin et al., "A Cell-Based High-Throughput Screen for Epidermal Growth Factor Receptor Pathway Inhibitors," Analytical Biochemistry, 377:89-94 (2008).
Kamath et al. "Targeting EGFR and HER-2 Receptor Tyrosine Kinases for Cancer Drug Discovery and Development." Medicinal Research Reviews, vol. 26, No. 5, 2006, pp. 569-594.
Hollis et al. "Tyrosine Kinase Inhibitors. 16. 6,5,6-Tricyclic Benzothieno[3,4-d]pyrimidines and Pyrimido[5,4-b]- and -[4,5-b] indoles as Potent Inhibitors of the Epidermal Growth Factor Receptor Tyrosine Kinase." J. Med. Chem. 1999, 42, 1999, pp. 5464-5474.
International Search Report issued in Application No. PCT/US2009/063684 dated Jul. 20, 2010, 7 pages.

Primary Examiner — Susanna Moore
(74) Attorney, Agent, or Firm — Occhiuti Rohlicek & Tsao LLP

(57) ABSTRACT

Fused bicyclic or tricyclic compounds of formula (I):

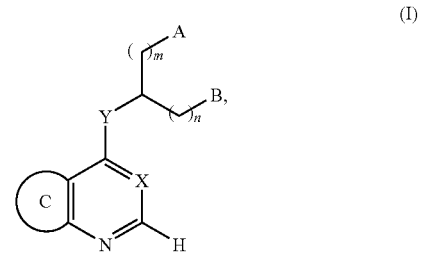

wherein A, B, C, X, Y, m, and n are defined herein. Also disclosed are a method for inhibiting EGFR kinase activity and a method for treating cancer with these compounds.

19 Claims, No Drawings

FUSED BICYCLIC AND TRICYCLIC PYRIMIDINE COMPOUNDS AS TYROSINE KINASE INHIBITORS

CROSS-REFERENCE TO RELATED APPLICATION

This application claims the benefit of the priority pursuant to 35 U.S.C. §119(e) of U.S. Provisional Patent Application No. 61/112,865, filed Nov. 10, 2008. The content of the prior application is incorporated herein by its entirety.

BACKGROUND

Protein kinases play important roles in cellular signal pathways that regulate various cell functions such as differentiation, proliferation, migration, and apoptosis. Deregulation of protein kinases is implicated in a number of diseases including cancer. Thus protein kinases are attractive therapeutic targets in cancer treatment.

Epidermal growth factor receptor (EGFR) is a subfamily of four closely related receptor tyrosine kinases: EGFR, HER2, HER3, and HER4. Binding of EGF ligand to the extracellular domain of EGFR leads to activation of the intracellular protein-tyrosine kinase activity. As a result, autophosphorylation of several tyrosine residues in the C-terminal domain of EGFR occurs. (Kamath, S., Buolamwini, J. K., *Med. Res. Rev.* 2006, 26, 569-594).

Deregulation in the EGFR signaling cascade has been implicated in the development of various cancers such as bladder, breast, colon, and lung cancer. Several EGFR kinase inhibitors, such as Gefitinib and Erlotinib, have been used for treating cancer, particularly Non-Small Cell Lung cancer (NSCLC). However, only 10-20% of the NSCLC patients respond to Gefitinib treatment, mainly due to drug resistance caused by T790M mutation in EGFR kinase. Thus, it is of great interest to develop EGFR kinase inhibitors, especially those which can inhibit activity of EGFR mutants (e.g., the T790M mutant), as anti-cancer drugs.

SUMMARY

This invention is based on the unexpected discovery that certain fused bicyclic or tricyclic compounds can be used to inhibit activity of EGFR kinase (e.g., EGFR T790M mutant), which allows these compounds to be applied in treating cancer (e.g., NSCLC).

In one aspect, this invention relates to a fused bicyclic or tricyclic compound of formula (I):

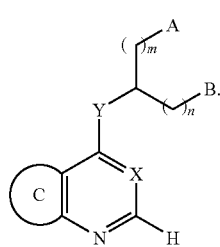

In formula (I), X is N or $CR_1$, in which $R_1$ is CN, $CONH_2$, halo, or H; Y is O, S, or $NR_2$, in which $R_2$ is H, alkyl, alkenyl, alkynyl, aryl, heteroaryl, cycloalkyl, cycloalkenyl, heterocycloalkyl, or heterocycloalkenyl; A is alkyl, alkenyl, alkynyl, aryl, heteroaryl, cycloalkyl, cycloalkenyl, heterocycloalkyl, heterocycloalkenyl, halo, cyano, nitro, $OR_3$, $OC(O)R_3$, $C(O)R_3$, $C(O)OR_3$, $C(O)NR_3R_4$, $NR_3R_4$, $NHC(O)R_3$, $NHC(O)NR_3R_4$, $NHC(S)R_3$, $NHC(O)OR_3$, $SO_2R_3$, $SO_3R_3$, or $SO_2NR_3R_4$, in which each of $R_3$ and $R_4$, independently, is H, alkyl, alkenyl, alkynyl, silyl, aryl, heteroaryl, cycloalkyl, cycloalkenyl, heterocycloalkyl, or heterocycloalkenyl, or $R_3$ and $R_4$, together with the nitrogen atoms to which they are bonded, are heterocycloalkyl, heterocycloalkenyl, or heteroaryl; B is aryl or heteroaryl; each of m and n, independently, is 0, 1, or 2; and ring C is

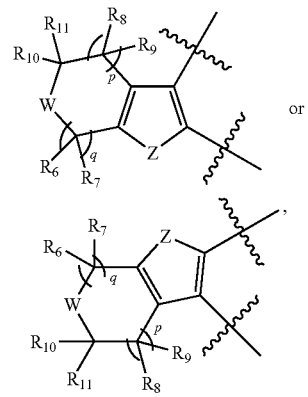

in which p is 0, 1, or 2, q is 1 or 2, Z is O, S, or NH, W is $CH_2$ or $NR_5$, in which $R_5$ is H, alkyl, alkenyl, alkynyl, aryl, heteroaryl, cycloalkyl, cycloalkenyl, heterocycloalkyl, heterocycloalkenyl, $C(O)R_a$, $C(O)C(O)R_a$, $C(O)OR_a$, $C(O)NR_aR_b$, or $SO_2R_a$, in which each of $R_a$ and $R_b$, independently, is H, alkyl, alkenyl, alkynyl, aryl, heteroaryl, cycloalkyl, cycloalkenyl, heterocycloalkyl, or heterocycloalkenyl, or $R_a$ and $R_b$, together with the nitrogen atoms to which they are bonded, are heterocycloalkyl, heterocycloalkenyl, or heteroaryl, and each of $R_6$, $R_7$, $R_8$, $R_9$, $R_{10}$, and $R_{11}$, independently, is H, alkyl, or halo. In particular, this invention relates to a fused bicyclic or tricyclic compound of formula (II):

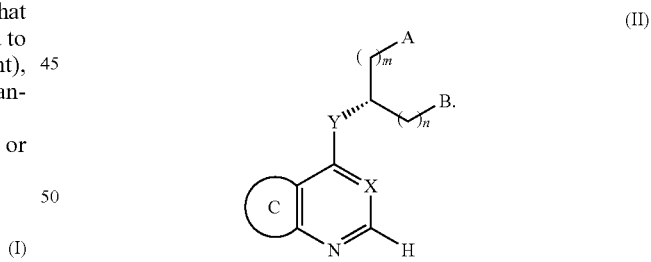

One subset of the above-described compounds includes those in which W is $NR_5$, $R_5$ being $SO_2R_a$,

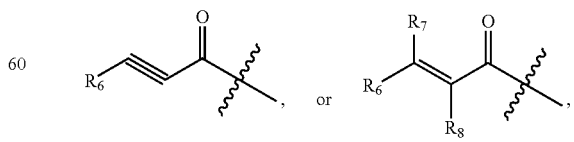

in which each of $R_6$ and $R_7$, independently, is H, alkyl optionally substituted with alkylamino (e.g., dialkylamino), alkenyl, alkynyl, aryl, heteroaryl, cycloalkyl, cycloalkenyl, heterocycloalkyl, heterocycloalkenyl, C(O)R$_c$, C(O)OR$_c$, C(O)NR$_c$R$_d$, or CH$_2$NR$_c$R$_d$, in which each of R$_c$ and R$_d$, independently, is H, alkyl, alkenyl, alkynyl, aryl, heteroaryl, cycloalkyl, cycloalkenyl, heterocycloalkyl, or heterocycloalkenyl, or R$_c$ and R$_d$, together with the nitrogen atoms to which they are bonded, are heterocycloalkyl, heterocycloalkenyl, or heteroaryl, and R$_g$ is H, alkyl, alkenyl, alkynyl, aryl, heteroaryl, cycloalkyl, cycloalkenyl, heterocycloalkyl, or heterocycloalkenyl. In these compounds, A can be OR$_3$, R$_3$ being H, aryl, heteroaryl, or C$_{1-3}$ alkyl optionally substituted with aryl or heteroaryl or A can be C(O)OR$_3$; B can be phenyl; m can be 0 or 1; n can be 0; X can be N; Y can be NH; or Z can be S.

Another subset of the compounds includes those in which W is CH$_2$. In these compounds, A can be OR$_3$, R$_3$ being H, aryl, heteroaryl, or C$_{1-3}$ alkyl optionally substituted with aryl or heteroaryl, or A can be C(O)OR$_3$; B can be phenyl; m can be 0 or 1; n can be 0; X can be N; Y can be NH; or Z can be S.

The term "alkyl" refers to a straight or branched monovalent hydrocarbon containing 1-20 carbon atoms (e.g., C$_1$-C$_{10}$). Examples of alkyl include, but are not limited to, methyl, ethyl, n-propyl, i-propyl, n-butyl, i-butyl, and t-butyl. The term "alkenyl" refers to a straight or branched monovalent hydrocarbon containing 2-20 carbon atoms (e.g., C$_2$-C$_{10}$) and one or more double bonds. Examples of alkenyl include, but are not limited to, ethenyl, propenyl, and allyl. The term "alkynyl" refers to a straight or branched monovalent hydrocarbon containing 2-20 carbon atoms (e.g., C$_2$-C$_{10}$) and one or more triple bonds. Examples of alkynyl include, but are not limited to, ethynyl, 1-propynyl, 1- and 2-butynyl, and 1-methyl-2-butynyl. The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., C$_3$-C$_{12}$). Examples of cycloalkyl include, but are not limited to, cyclopropyl, cyclobutyl, cyclopentyl, cyclohexyl, cycloheptyl, and cyclooctyl. The term "cycloalkenyl" refers to a monovalent non-aromatic hydrocarbon ring system having 3 to 30 carbons (e.g., C$_3$-C$_{12}$) and one or more double bonds. Examples include cyclopentenyl, cyclohexenyl, and cycloheptenyl. The term "heterocycloalkyl" refers to a monovalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, C$_1$-C$_{10}$ alkoxy, aryl, aryloxy, heteroaryl, heteroaryloxy, amino, C$_1$-C$_{10}$ alkylamino, arylamino, hydroxy, halo, oxo (O═), thioxo (S═), thio, silyl, C$_1$-C$_{10}$ alkylthio, arylthio, C$_1$-C$_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except C$_1$-C$_{10}$ alkyl. Cycloalkyl, cycloalkenyl, heterocycloalkyl, heterocycloalkenyl, aryl, and heteroaryl can also be fused with each other.

In another aspect, this invention relates to a fused bicyclic or tricyclic compound of formula (I):

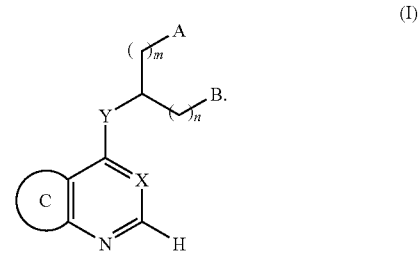

In formula (I), X is N or CR$_1$, in which R$_1$ is CN, CONH$_2$, halo, or H; Y is O, S, or NR$_2$, in which R$_2$ is H, alkyl, alkenyl, alkynyl, aryl, heteroaryl, cycloalkyl, cycloalkenyl, heterocycloalkyl, or heterocycloalkenyl; A is alkyl, alkenyl, alkynyl, aryl, heteroaryl, cycloalkyl, cycloalkenyl, heterocycloalkyl, heterocycloalkenyl, halo, cyano, nitro, OR$_3$, OC(O)R$_3$, C(O)R$_3$, C(O)OR$_3$, C(O)NR$_3$R$_4$, NR$_3$R$_4$, NHC(O)R$_3$, NHC(O)NR$_3$R$_4$, NHC(S)R$_3$, NHC(O)OR$_3$, SO$_2$R$_3$, SO$_3$R$_3$, or SO$_2$NR$_3$R$_4$, in which each of R$_3$ and R$_4$, independently, is H, alkyl, alkenyl, alkynyl, silyl, aryl, heteroaryl, cycloalkyl, cycloalkenyl, heterocycloalkyl, or heterocycloalkenyl, or R$_3$ and R$_4$, together with the nitrogen atoms to which they are bonded, are heterocycloalkyl, heterocycloalkenyl, or heteroaryl; B is aryl or heteroaryl; each of m and n, independently, is 0, 1, or 2; and ring C is

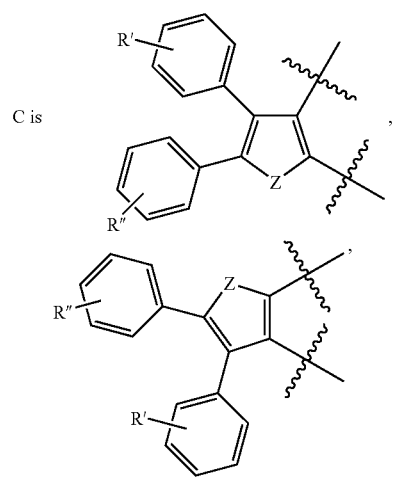

-continued

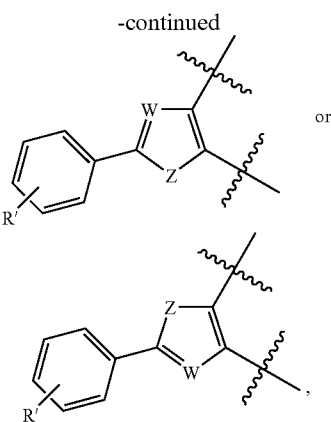

in which each of R' and R", independently, is H, alkyl, alkenyl, alkynyl, aryl, heteroaryl, cycloalkyl, cycloalkenyl, heterocycloalkyl, heterocycloalkenyl, halo, nitro, cyano, $OR_a$, $OR_aO$, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$, in which each of $R_a$ and $R_b$, independently, is H, alkyl, alkenyl, alkynyl, aryl, heteroaryl, cycloalkyl, cycloalkenyl, heterocycloalkyl, or heterocycloalkenyl, or $R_a$ and $R_b$, together with the nitrogen atoms to which they are bonded, are heterocycloalkyl, heterocycloalkenyl, or heteroaryl, Z is O or NH, provided that at most one of R' and R" is H, and W is N or $CR_5$, in which $R_5$ is alkenyl, alkynyl, aryl substituted with $OR_a$, $OR_aO$, or $NR_b$-$C(O)R_a$, heteroaryl, cycloalkyl, cycloalkenyl, heterocycloalkyl, heterocycloalkenyl, halo, nitro, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$. In particular, the compound is of formula (II):

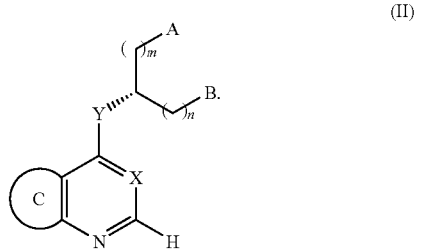

(II)

One subset of the compounds described immediately above includes those in which R' is

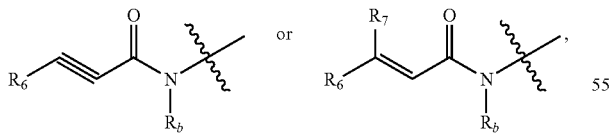

$R_6$ being H, alkyl, alkenyl, alkynyl, aryl, heteroaryl, cycloalkyl, cycloalkenyl, heterocycloalkyl, heterocycloalkenyl, $C(O)R_c$, $C(O)OR_c$, $C(O)NR_cR_d$, or $CH_2NR_cR_d$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl, or $R_c$ and $R_d$, together with the nitrogen atoms to which they are bonded, are heterocycloalkyl, heterocycloalkenyl, or heteroaryl, and $R_7$ being H, alkyl, alkenyl, alkynyl, aryl, heteroaryl, cycloalkyl, cycloalkenyl, heterocycloalkyl, or heterocycloalkenyl. In these compounds, A can be $OR_3$, $R_3$ being H, aryl, heteroaryl, or $C_{1-3}$ alkyl optionally substituted with aryl or heteroaryl; B can be phenyl; m can be 1; n can be 0; X can be N; Y can be NH; or Z can be O.

Another subset of the compounds includes those in which B is phenyl and n is 0. In these compounds, A can be $OR_3$, $R_3$ being H, aryl, heteroaryl, or $C_{1-3}$ alkyl optionally substituted with aryl or heteroaryl, or A can be $C(O)OR_3$; m can be 0 or 1; X can be N; Y can be NH; Z can be O; W can be $CR_5$, in which $R_5$ is halo; or each of R' and R", independently, can be $OR_a$.

In still another aspect, this invention relates to a fused bicyclic or tricyclic compound of formula (I):

(I)

In formula (I), X is N or $CR_1$, in which $R_1$ is CN, $CONH_2$, halo, or H; Y is O, S, or $NR_2$, in which $R_2$ is H, alkyl, alkenyl, alkynyl, aryl, heteroaryl, cycloalkyl, cycloalkenyl, heterocycloalkyl, or heterocycloalkenyl; A is alkenyl, alkynyl, aryl, heteroaryl, cycloalkyl, cycloalkenyl, heterocycloalkyl, heterocycloalkenyl, halo, cyano, nitro, $OC(O)R_3$, $C(O)R_3$, $C(O)OR_3$, $C(O)NR_3R_4$, $NR_3R_4$, $NHC(O)R_3$, $NHC(O)NR_3R_4$, $NHC(S)R_3$, $NHC(O)OR_3$, $SO_2R_3$, $SO_3R_3$, or $SO_2NR_3R_4$, in which each of $R_3$ and $R_4$, independently, is H, alkyl, alkenyl, alkynyl, aryl, heteroaryl, cycloalkyl, cycloalkenyl, heterocycloalkyl, or heterocycloalkenyl, or $R_3$ and $R_4$, together with the nitrogen atoms to which they are bonded, are heterocycloalkyl, heterocycloalkenyl, or heteroaryl; B is aryl or heteroaryl; each of m and n, independently, is 0, 1, or 2; and ring C is

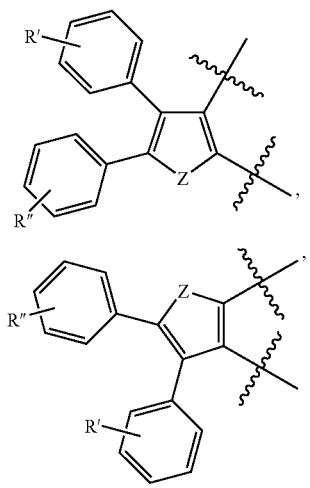

-continued

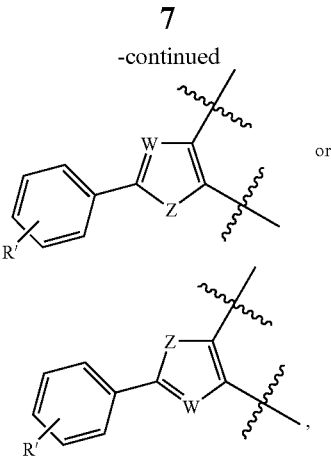

in which each of R' and R", independently, is H, alkyl, alkenyl, alkynyl, aryl, heteroaryl, cycloalkyl, cycloalkenyl, heterocycloalkyl, heterocycloalkenyl, halo, nitro, cyano, $OR_a$, $OR_aO$, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$, in which each of $R_a$ and $R_b$, independently, is H, alkyl, alkenyl, alkynyl, aryl, heteroaryl, cycloalkyl, cycloalkenyl, heterocycloalkyl, or heterocycloalkenyl, or $R_a$ and $R_b$, together with the nitrogen atoms to which they are bonded, are heterocycloalkyl, heterocycloalkenyl, or heteroaryl, Z is O or NH, and W is N or $CR_5$, in which $R_5$ is alkenyl, alkynyl, aryl, heteroaryl, cycloalkyl, cycloalkenyl, heterocycloalkyl, heterocycloalkenyl, halo, nitro, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$. In particular, the compound is of formula (II):

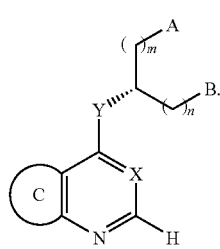

(II)

In yet another aspect, this invention relates to a fused bicyclic or tricyclic compound of formula (I):

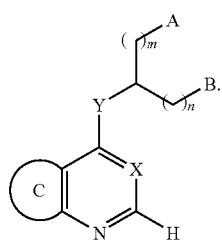

(I)

In formula (I), X is N or $CR_1$, in which $R_1$ is CN, $CONH_2$, halo, or H; Y is O, S, or $NR_2$, in which $R_2$ is H, alkyl, alkenyl, alkynyl, aryl, heteroaryl, cycloalkyl, cycloalkenyl, heterocycloalkyl, or heterocycloalkenyl; A is alkenyl, alkynyl, aryl, heteroaryl, cycloalkyl, cycloalkenyl, heterocycloalkyl, heterocycloalkenyl, halo, cyano, nitro, $OR_3$, $OC(O)R_3$, $C(O)R_3$, $C(O)OR_3$, $C(O)NR_3R_4$, $NR_3R_4$, $NHC(O)R_3$, $NHC(O)NR_3R_4$, $NHC(S)R_3$, $NHC(O)OR_3$, $SO_2R_3$, $SO_3R_3$, or $SO_2NR_3R_4$, in which each of $R_3$ and $R_4$, independently, is H, alkyl, alkenyl, alkynyl, silyl, aryl, heteroaryl, cycloalkyl, cycloalkenyl, heterocycloalkyl, or heterocycloalkenyl, or $R_3$ and $R_4$, together with the nitrogen atoms to which they are bonded, are heterocycloalkyl, heterocycloalkenyl, or heteroaryl when X is N, and A is H, alkyl, alkenyl, alkynyl, aryl, heteroaryl, cycloalkyl, cycloalkenyl, heterocycloalkyl, heterocycloalkenyl, halo, cyano, nitro, $OR_3$, $OC(O)R_3$, $C(O)R_3$, $C(O)OR_3$, $C(O)NR_3R_4$, $NR_3R_4$, $NHC(O)R_3$, $NHC(O)NR_3R_4$, $NHC(S)R_3$, $NHC(O)OR_3$, $SO_2R_3$, $SO_3R_3$, or $SO_2NR_3R_4$ when X is $CR_1$; B is aryl or heteroaryl; each of m and n, independently, is 0, 1, or 2; and ring C is

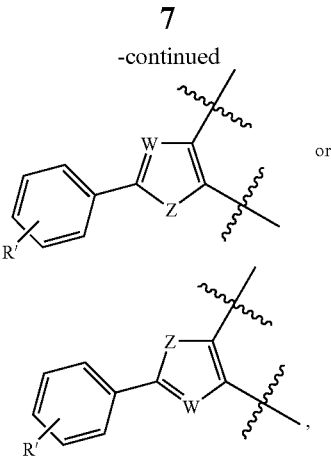

in which each of R' and R", independently, is H, alkyl, alkenyl, alkynyl, aryl, heteroaryl, cycloalkyl, cycloalkenyl, heterocycloalkyl, heterocycloalkenyl, halo, nitro, cyano, $OR_a$, $OR_aO$, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$, in which each of $R_a$ and $R_b$, independently, is H, alkyl, alkenyl, alkynyl, aryl, heteroaryl, cycloalkyl, cycloalkenyl, heterocycloalkyl, or heterocycloalkenyl, or $R_a$ and $R_b$, together with the nitrogen atoms to which they are bonded, are heterocycloalkyl, heterocycloalkenyl, or heteroaryl, Z is S, and W is N or $CR_5$, in which $R_5$ is H, alkyl, alkenyl, alkynyl, aryl, heteroaryl, cycloalkyl, cycloalkenyl, heterocycloalkyl, heterocycloalkenyl, halo, nitro, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$. In particular, the compound is of formula (II):

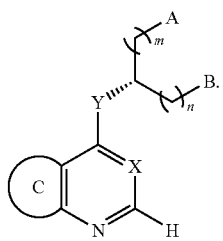

(II)

Further, this invention relates to a fused bicyclic or tricyclic compound of formula

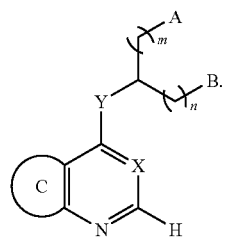

(I)

In formula (I), X is N or $CR_1$, in which $R_1$ is CN, $CONH_2$, halo, or H; Y is O, S, or $NR_2$, in which $R_2$ is H, alkyl, alkenyl, alkynyl, aryl, heteroaryl, cycloalkyl, cycloalkenyl, heterocycloalkyl, or heterocycloalkenyl; A is alkyl, alkenyl, alkynyl, aryl, heteroaryl, cycloalkyl, cycloalkenyl, heterocycloalkyl, heterocycloalkenyl, halo, cyano, nitro, $OR_3$, $OC(O)R_3$, $C(O)R_3$, $C(O)OR_3$, $C(O)NR_3R_4$, $NR_3R_4$, $NHC(O)R_3$, $NHC(O)NR_3R_4$, $NHC(S)R_3$, $NHC(O)OR_3$, $SO_2R_3$, $SO_3R_3$, or $SO_2NR_3R_4$, in which each of $R_3$ and $R_4$, independently, is H, alkyl, alkenyl, alkynyl, silyl, aryl, heteroaryl, cycloalkyl, cycloalkenyl, heterocycloalkyl, or heterocycloalkenyl, or $R_3$ and $R_4$, together with the nitrogen atoms to which they are bonded, are heterocycloalkyl, heterocycloalkenyl, or heteroaryl; B is aryl or heteroaryl; each of m and n, independently, is 0, 1, or 2; and ring C is

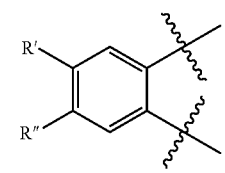

in which each of R' and R", independently, is H, alkyl, alkenyl, alkynyl, aryl, heteroaryl, cycloalkyl, cycloalkenyl, heterocycloalkyl, heterocycloalkenyl, nitro, cyano, $OR_a$, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$, in which each of $R_a$ and $R_b$, independently, is H, alkyl, alkenyl, alkynyl, aryl, heteroaryl, cycloalkyl, cycloalkenyl, heterocycloalkyl, or heterocycloalkenyl, or $R_a$ and $R_b$, together with the nitrogen atoms to which they are bonded, are heterocycloalkyl, heterocycloalkenyl, or heteroaryl, provided that at least one of R' and R" is $NR_bC(O)R_a$, $NHC(O)NR_aR_b$, $NR_bC(S)R_a$, or $NHSO_2R_a$. In particular, the compound is of formula (II):

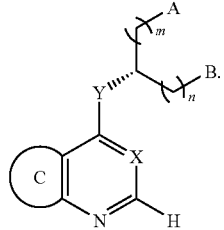

(II)

One subset of the compounds described immediately above includes those in which R' is

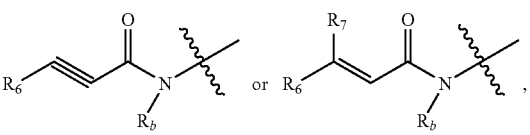

$R_6$ being H, alkyl, alkenyl, alkynyl, aryl, heteroaryl, cycloalkyl, cycloalkenyl, heterocycloalkyl, heterocycloalkenyl, $C(O)R_c$, $C(O)OR_c$, $C(O)NR_cR_d$, or $CH_2NR_cR_d$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl, or $R_c$ and $R_d$, together with the nitrogen atoms to which they are bonded, are heterocycloalkyl, heterocycloalkenyl, or heteroaryl, and $R_7$ being H, alkyl, alkenyl, alkynyl, aryl, heteroaryl, cycloalkyl, cycloalkenyl, heterocycloalkyl, or heterocycloalkenyl. In these compounds, A can be $OR_3$, $R_3$ being H, aryl, heteroaryl, or $C_{1-3}$ alkyl optionally substituted with aryl or heteroaryl, or A can be $C(O)OR_3$; B can be phenyl; m can be 0 or 1; or n can be 0.

In yet another aspect, this invention relates to a fused bicyclic or tricyclic compound of formula (I):

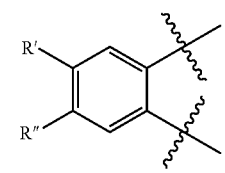

(I)

In formula (I), X is N or $CR_1$, in which $R_1$ is CN, $CONH_2$, halo, or H; Y is O, S, or $NR_2$, in which $R_2$ is H, alkyl, alkenyl, alkynyl, aryl, heteroaryl, cycloalkyl, cycloalkenyl, heterocycloalkyl, or heterocycloalkenyl; A is alkenyl, alkynyl, aryl, heteroaryl, cycloalkyl, cycloalkenyl, heterocycloalkyl, heterocycloalkenyl, halo, cyano, nitro, $OR_3$, $OC(O)R_3$, $C(O)R_3$, $C(O)OR_3$, $C(O)NR_3R_4$, $NR_3R_4$, $NHC(O)R_3$, $NHC(O)NR_3R_4$, $NHC(S)R_3$, $NHC(O)OR_3$, $SO_2R_3$, $SO_3R_3$, or $SO_2NR_3R_4$, in which each of $R_3$ and $R_4$, independently, is H, alkyl, alkenyl, alkynyl, silyl, aryl, heteroaryl, cycloalkyl, cycloalkenyl, heterocycloalkyl, or heterocycloalkenyl, or $R_3$ and $R_4$, together with the nitrogen atoms to which they are bonded, are heterocycloalkyl, heterocycloalkenyl, or heteroaryl when X is N, and A is H, alkyl, alkenyl, alkynyl, aryl, heteroaryl, cycloalkyl, cycloalkenyl, heterocycloalkyl, heterocycloalkenyl, halo, cyano, nitro, $OR_3$, $OC(O)R_3$, $C(O)R_3$, C(O)OR₃, C(O)NR₃R₄, NR₃R₄, NHC(O)R₃, NHC(O)NR₃R₄, NHC(S)R₃, NHC(O)OR₃, SO₂R₃, SO₃R₃, or SO₂NR₃R₄ when X is CR₁; B is aryl or heteroaryl; each of m and n, independently, is 0, 1, or 2; and ring C is

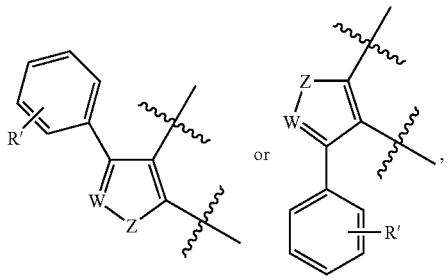

in which each of R' is H, alkyl, alkenyl, alkynyl, aryl, heteroaryl, cycloalkyl, cycloalkenyl, heterocycloalkyl, heterocycloalkenyl, halo, nitro, cyano, OR_a, OR_aO, C(O)OR_a, C(O)NR_aR_b, NR_bC(O)R_a, NHC(O)NR_aR_b, NR_aC(S)R_a, NHSO₂R_a, or NR_aR_b, in which each of R_a and R_b, independently, is H, alkyl, alkenyl, alkynyl, aryl, heteroaryl, cycloalkyl, cycloalkenyl, heterocycloalkyl, or heterocycloalkenyl, or R_a and R_b, together with the nitrogen atoms to which they are bonded, are heterocycloalkyl, heterocycloalkenyl, or heteroaryl, Z is O or S, and W is N or CR₅, in which R₅ is H, alkyl, alkenyl, alkynyl, aryl, heteroaryl, cycloalkyl, cycloalkenyl, heterocycloalkyl, heterocycloalkenyl, halo, nitro, C(O)OR_a, C(O)NR_aR_b, NR_bC(O)R_a, NHC(O)NR_aR_b, NR_bC(S)R_a, NHSO₂R_a, or NR_aR_b. In particular, the compound is of formula (II):

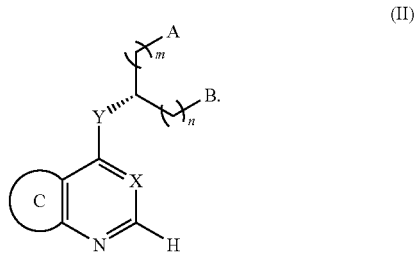

(II)

One subset of the compounds described immediately above includes those in which m is 1 and A is OR₃, R₃ being H, aryl, heteroaryl, or C₁₋₃ alkyl optionally substituted with aryl or heteroaryl. In these compounds, R' is

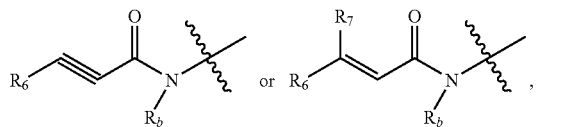

in which R₆ is H, alkyl, alkenyl, alkynyl, aryl, heteroaryl, cycloalkyl, cycloalkenyl, heterocycloalkyl, heterocycloalkenyl, C(O)R_c, C(O)OR_c, C(O)NR_cR_d, or CH₂NR_cR_d, in which each of R_c and R_d, independently, is H, alkyl, alkenyl, alkynyl, aryl, heteroaryl, cycloalkyl, cycloalkenyl, heterocycloalkyl, or heterocycloalkenyl, or R_c and R_d, together with the nitrogen atoms to which they are bonded, are heterocycloalkyl, heterocycloalkenyl, or heteroaryl, and R₇ is H, alkyl, alkenyl, alkynyl, aryl, heteroaryl, cycloalkyl, cycloalkenyl, heterocycloalkyl, or heterocycloalkenyl.

The fused bicyclic or tricyclic compounds described above include the compounds themselves, as well as their salts, their solvates, and their prodrugs, if applicable. A salt, for example, can be formed between an anion and a positively charged group (e.g., amino) on a fused bicyclic or tricyclic compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a fused bicyclic or tricyclic compound. Suitable cations include sodium ion, potassium ion, magnesium ion, calcium ion, and an ammonium cation such as tetramethylammonium ion. The fused bicyclic or tricyclic compounds also include those salts containing quaternary nitrogen atoms. Examples of prodrugs include esters and other pharmaceutically acceptable derivatives, which, upon administration to a subject, are capable of providing active fused bicyclic or tricyclic compounds.

This invention also relates to a method of inhibiting EGFR kinase (or other tyrosine kinases such as ERBB2 kinase) activity by contacting a cell expressing the protein kinase with an effective amount of one or more of the fused bicyclic or tricyclic compounds described above. The cell can be a tumor cell or a cell that over-expresses the protein kinase.

In addition, this invention encompasses a method of treating an EGFR kinase-mediated disorder (or other tyrosine kinases—such as ERBB2 kinase-related disorder) such as cancer by administering to a subject in need thereof an effective amount of one or more of the fused bicyclic or tricyclic compounds described above.

Also within the scope of this invention is a pharmaceutical composition containing one or more of the above-described fused bicyclic or tricyclic compounds for use in treating cancer (e.g., NSCLC), as well as this therapeutic use and use of the compounds for the manufacture of a medicament for treating cancer.

(S)-2-(5,6-dimethylthieno[2,3-d]pyrimidin-4-ylamino)-2-phenylethanol, (S)-2-(5-methylthieno[2,3-d]pyrimidin-4-ylamino)-2-phenylethanol, (S)-2-phenyl-2-(thieno[2,3-d]pyrimidin-4-ylamino)ethanol, and their analogs, as well as their therapeutic use as described above, are also contemplated.

The details of one or more embodiments of the invention are set forth in the description below. Other features, objects, and advantages of the invention will be apparent from the description and from the claims.

DETAILED DESCRIPTION

Shown below are exemplary compounds described herein:

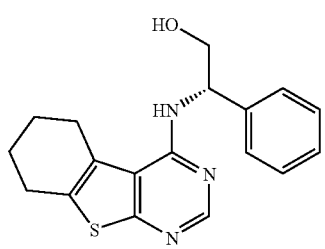

Compound 1

Compound 2
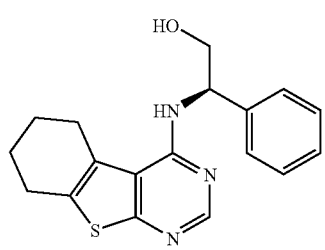
Compound 3
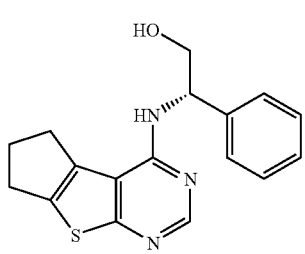
Compound 4
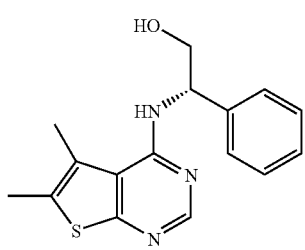
Compound 5
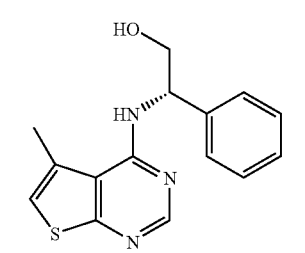
Compound 6
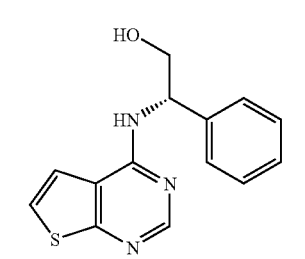
Compound 7
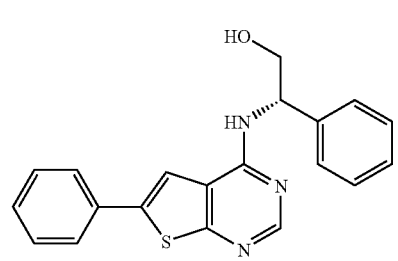
Compound 8
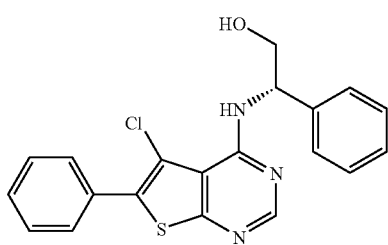
Compound 9
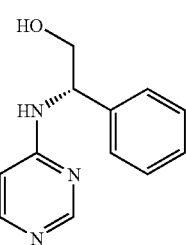
Compound 10
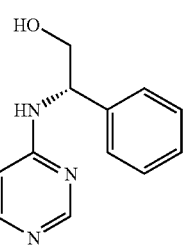
Compound 11
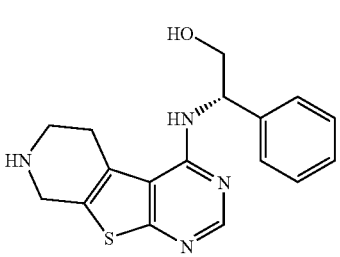
Compound 12
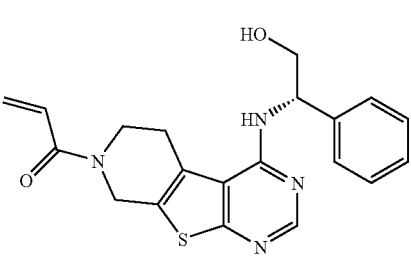
Compound 13
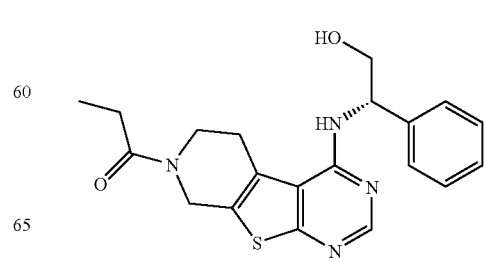

-continued
Compound 14
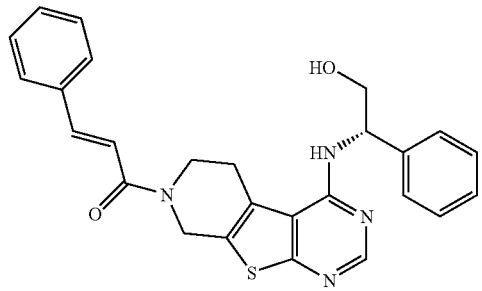
Compound 15
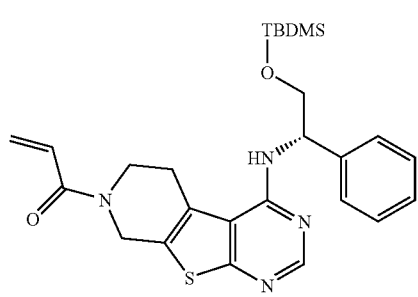
Compound 16
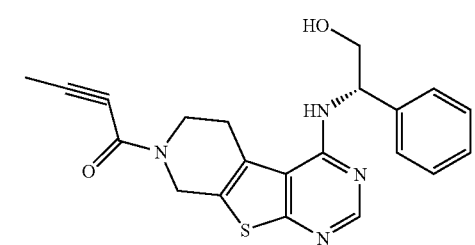
Compound 17
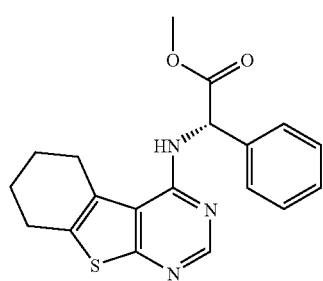
Compound 18
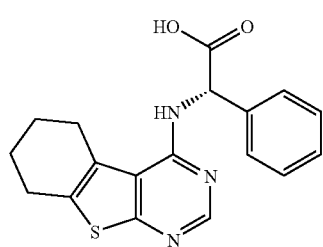
-continued
Compound 19
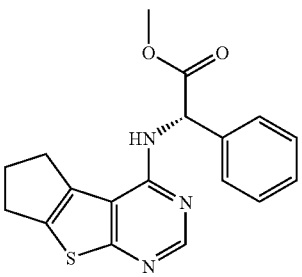
Compound 20
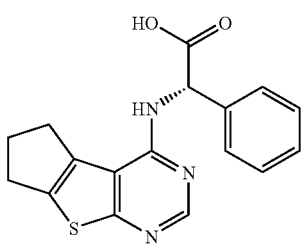
Compound 21
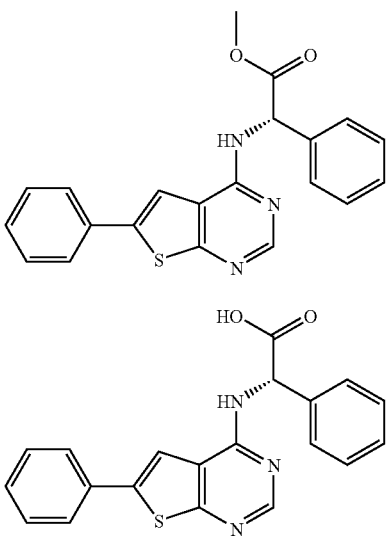
Compound 22
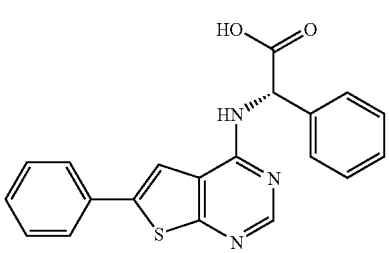
Compound 23
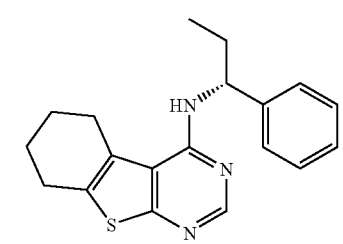
Compound 24
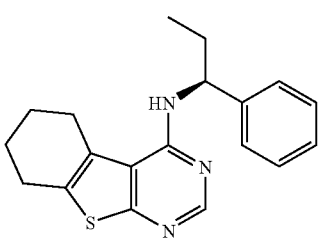

Compound 25
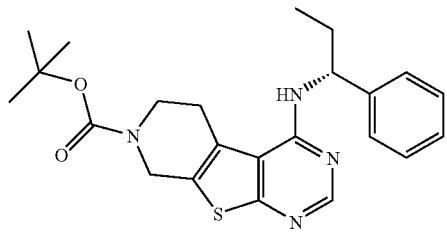
Compound 26
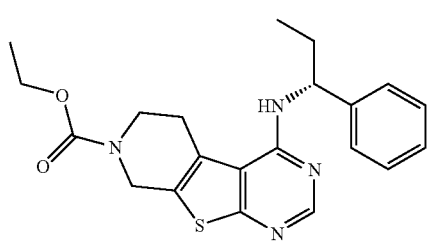
Compound 27
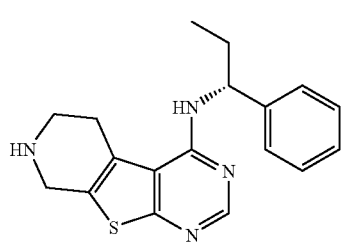
Compound 28
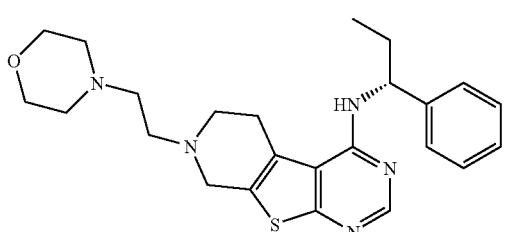
Compound 29
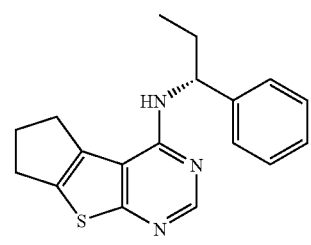
Compound 30
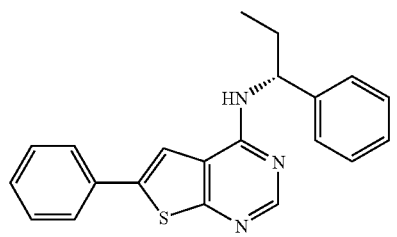
Compound 31
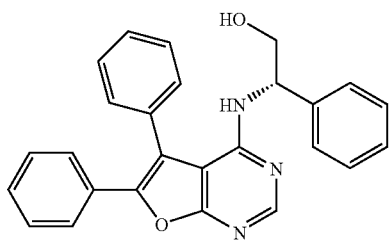
Compound 32
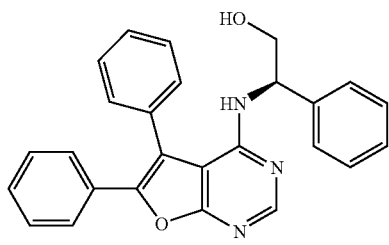
Compound 33
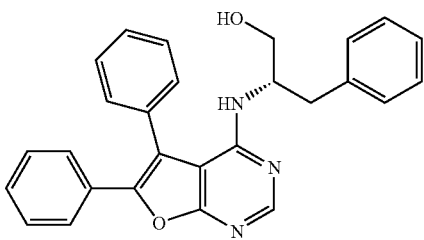
Compound 34
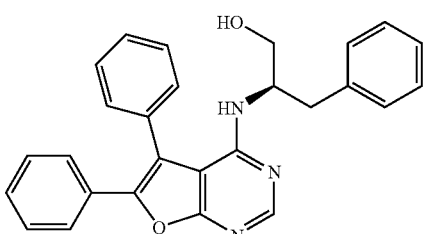
Compound 35
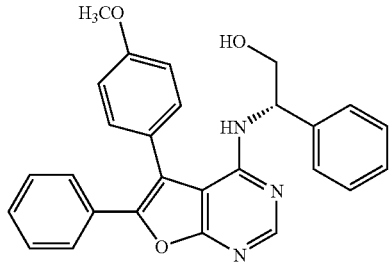
Compound 36
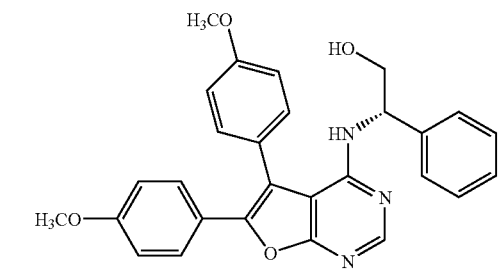

Compound 37
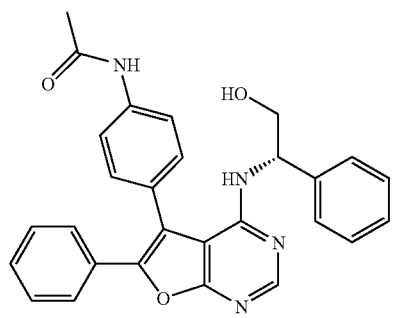
Compound 38
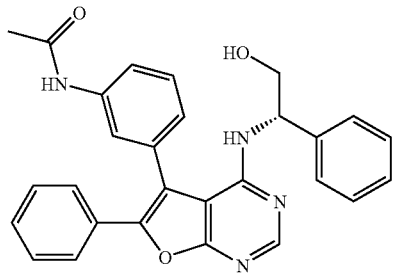
Compound 39
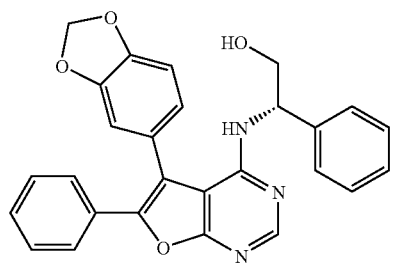
Compound 40
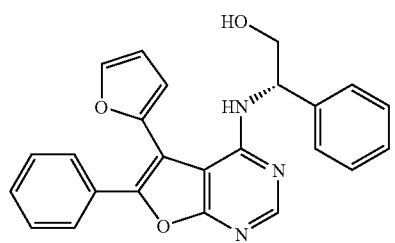
Compound 41
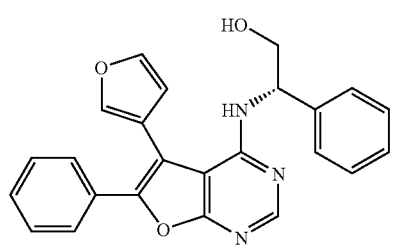
Compound 42
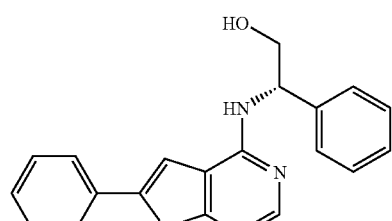
Compound 43
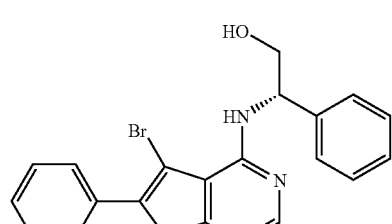
Compound 44
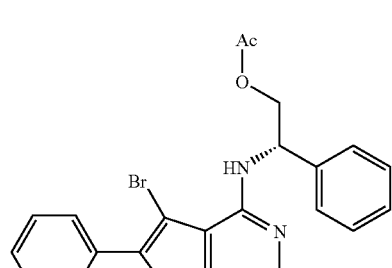
Compound 45
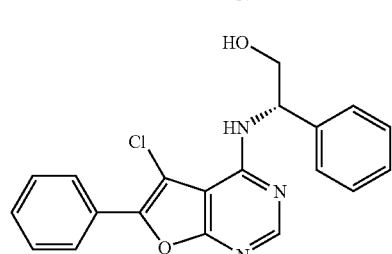
Compound 46
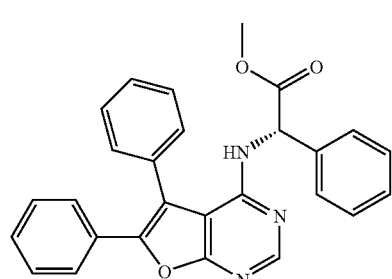
Compound 47
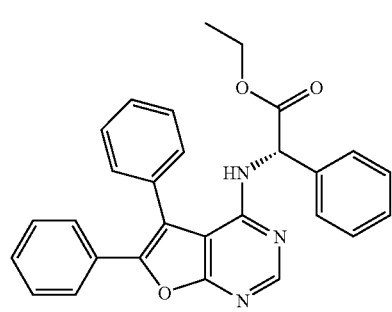

-continued
Compound 48
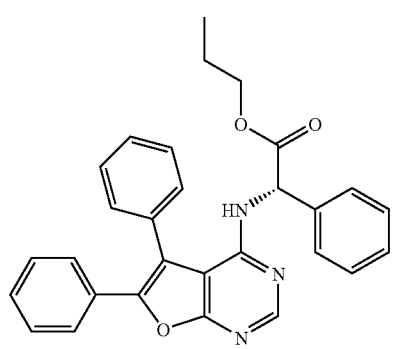
Compound 49
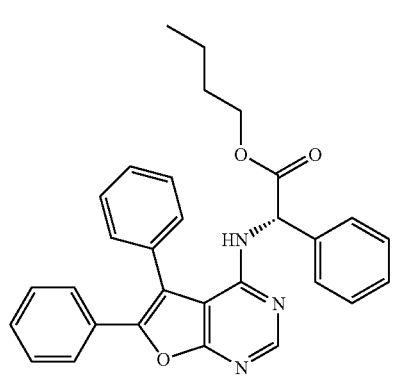
Compound 50
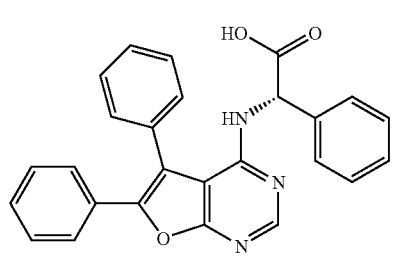
Compound 51
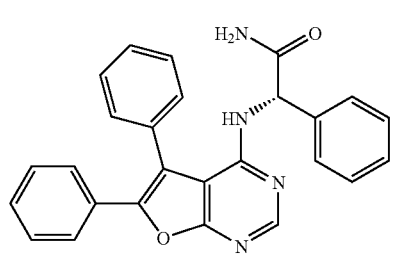
Compound 52
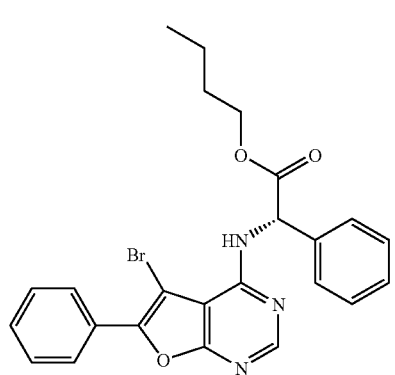
-continued
Compound 53
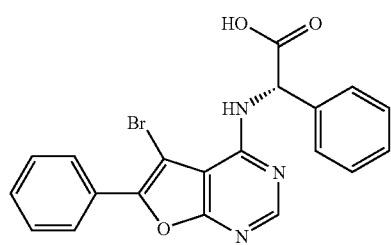
Compound 54
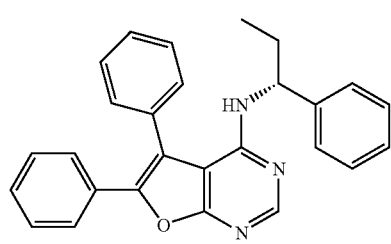
Compound 55
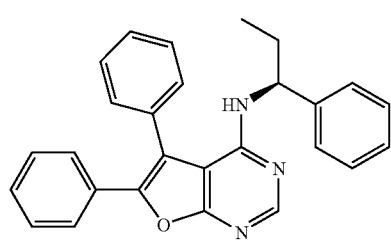
Compound 56
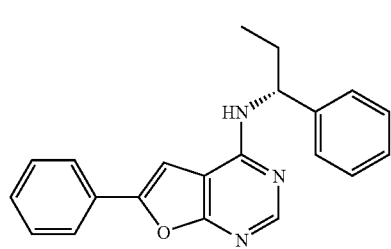
Compound 57
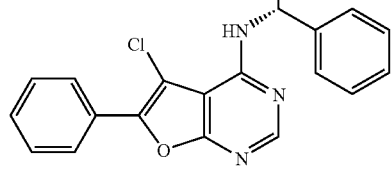
Compound 58
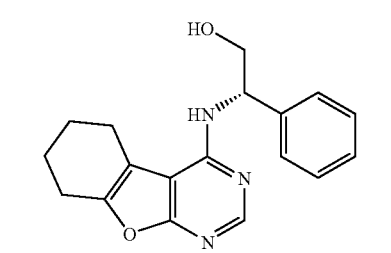

Compound 59
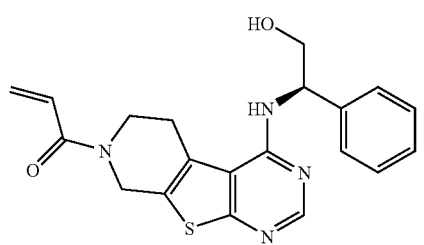
Compound 60
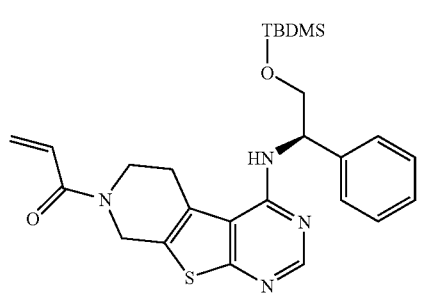
Compound 61
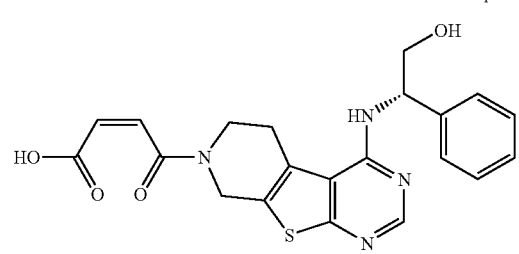
Compound 62
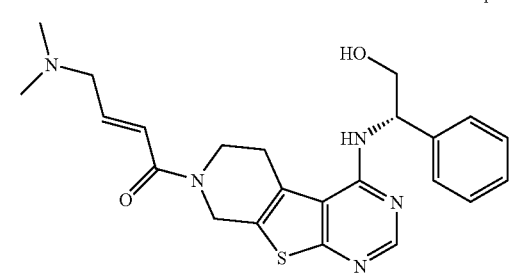
Compound 63
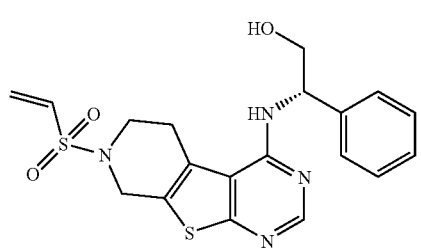
Compound 64
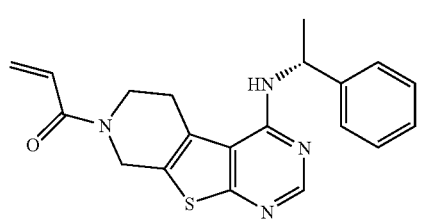
Compound 65
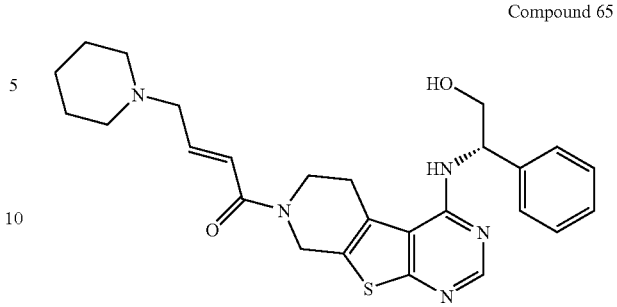
Compound 66
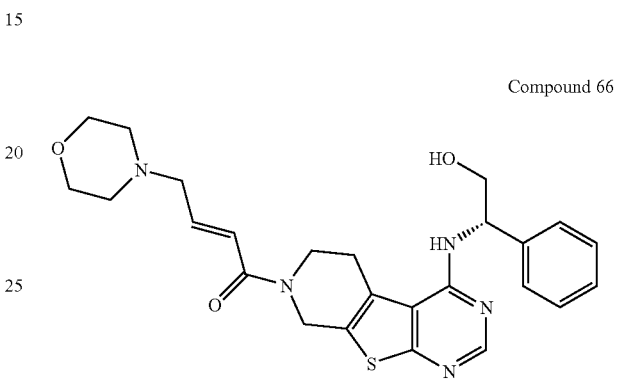
Compound 67
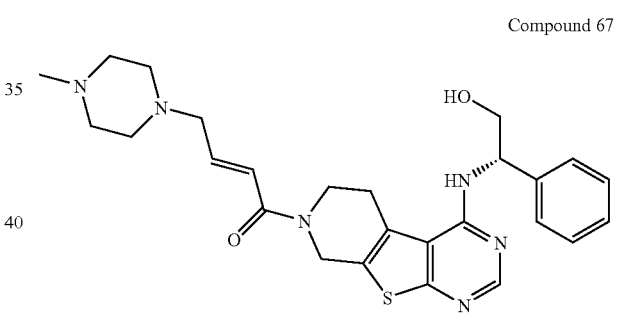
Compound 68
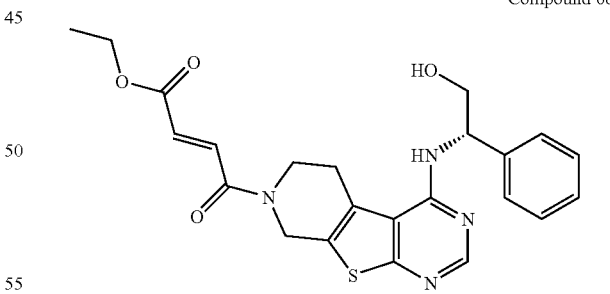
Compound 69
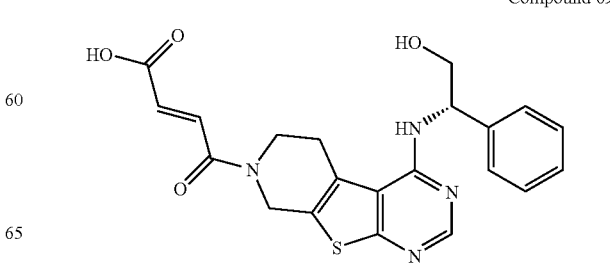

Compound 70
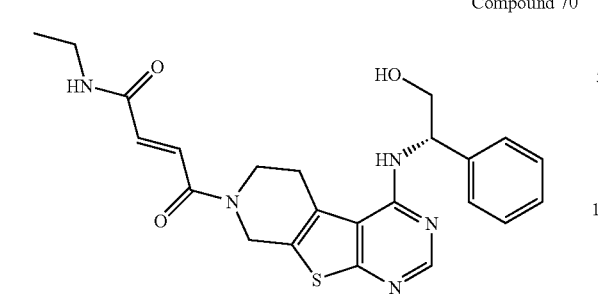
Compound 75
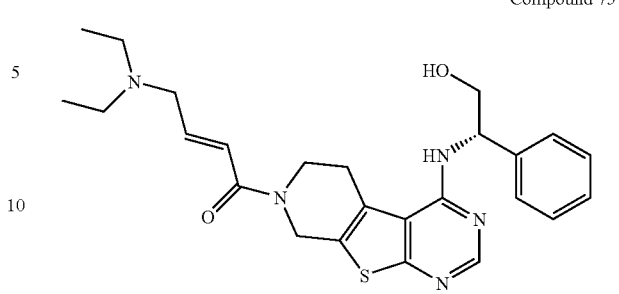
Compound 76
Compound 71
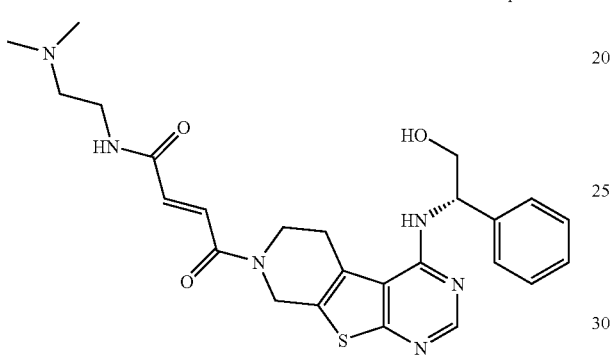
Compound 77
Compound 72
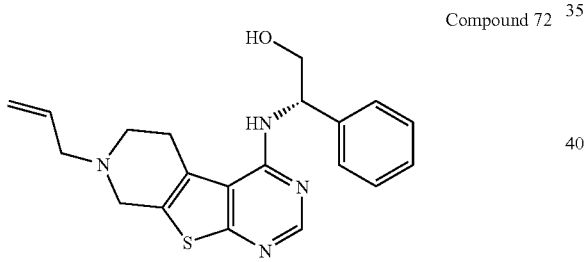
Compound 78
Compound 73
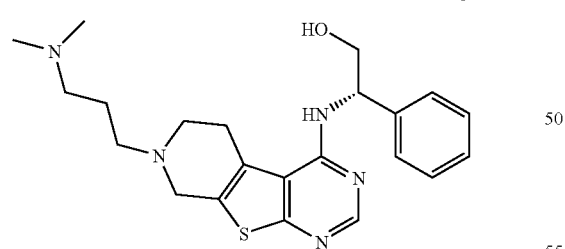
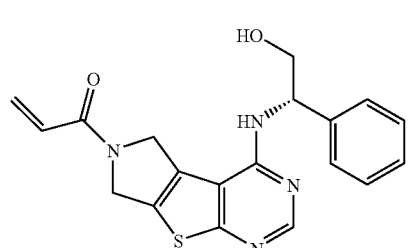
Compound 79
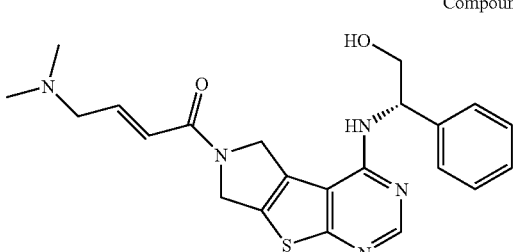
Compound 74
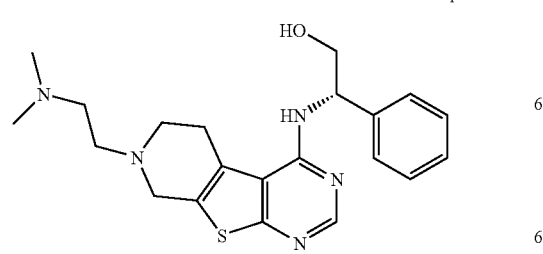
Compound 80
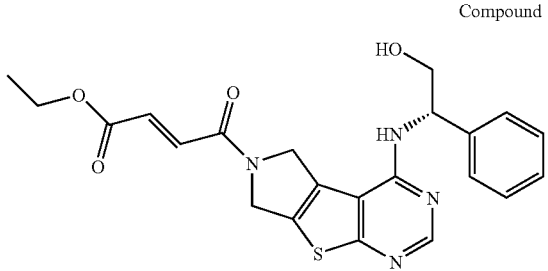

Compound 81
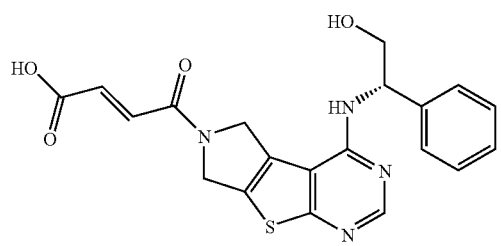
Compound 82
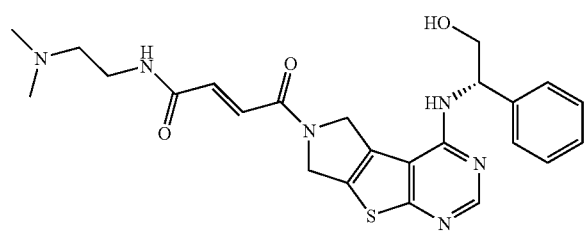
Compound 83
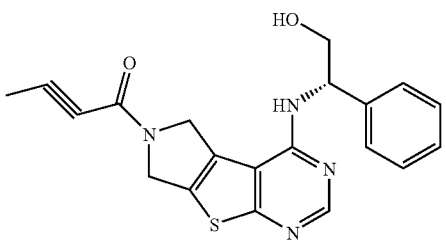
Compound 84
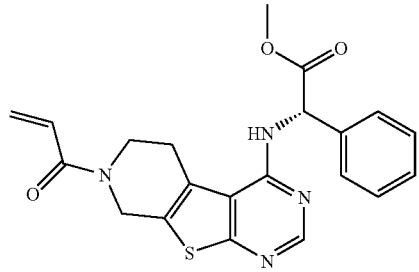
Compound 85
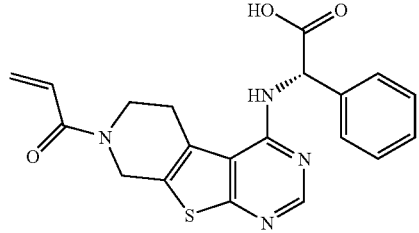
Compound 86
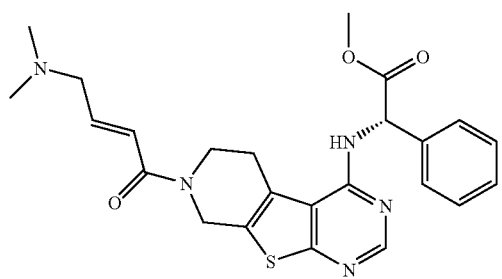
Compound 87
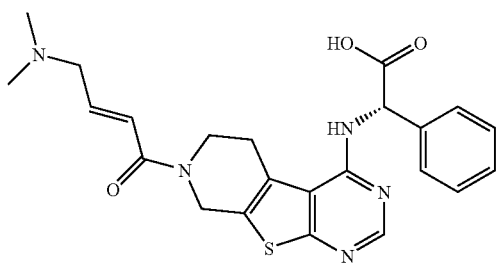
Compound 88
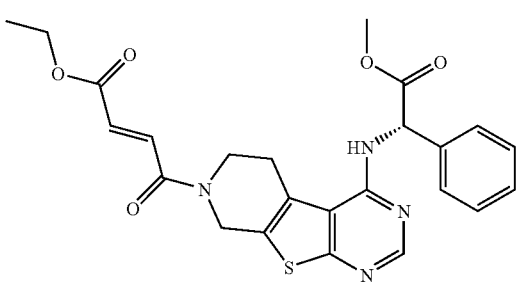
Compound 89
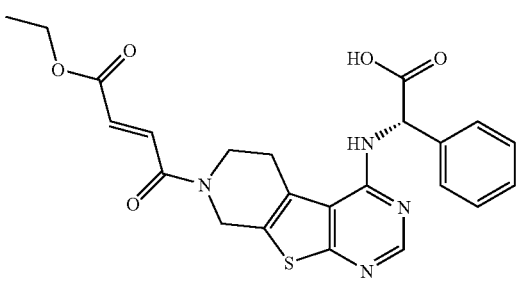
Compound 90
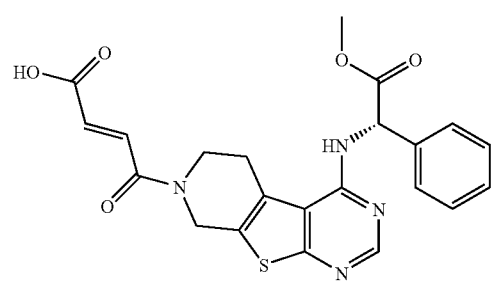
Compound 91
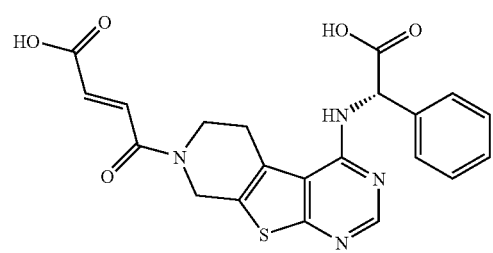

Compound 92
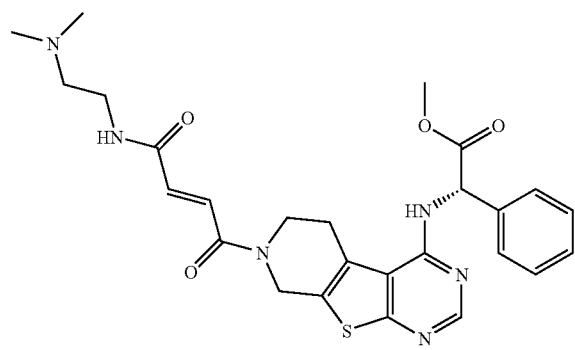
Compound 93
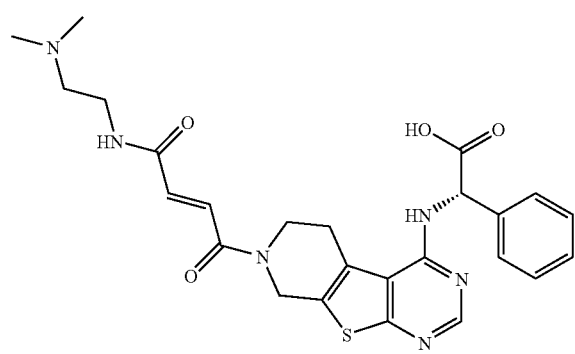
Compound 94
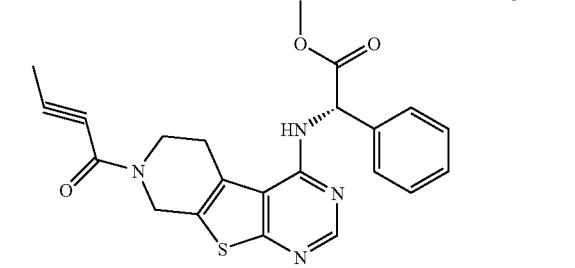
Compound 95
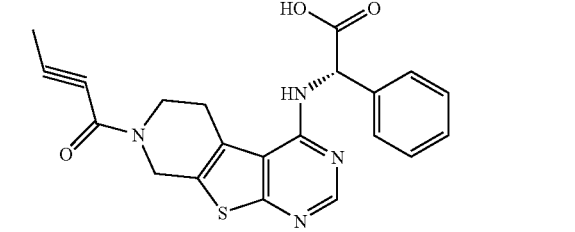
Compound 96
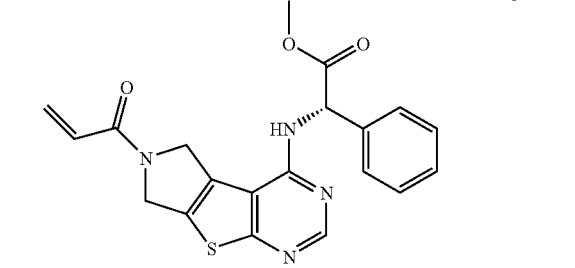
Compound 97
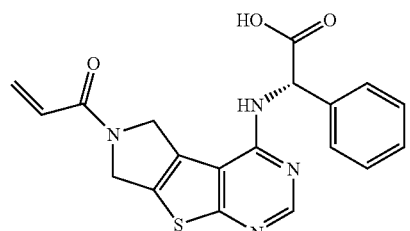
Compound 98
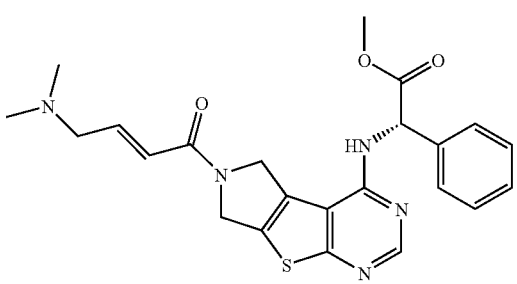
Compound 99
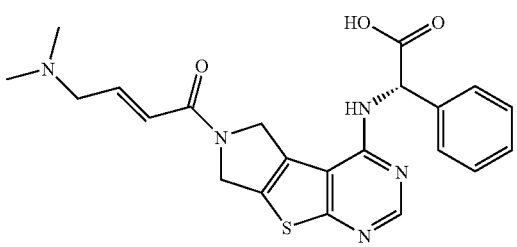
Compound 100
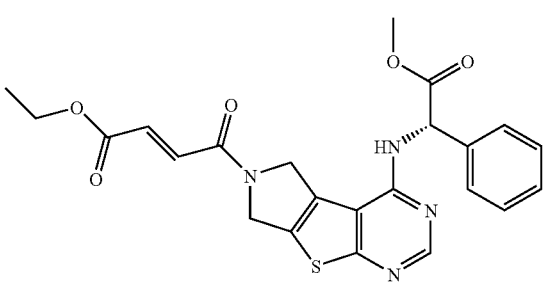
Compound 101
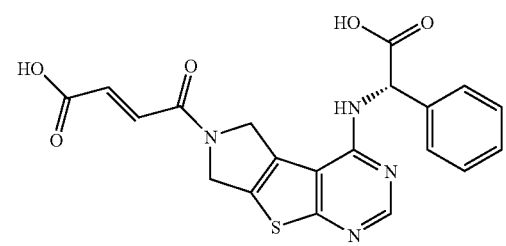
Compound 102
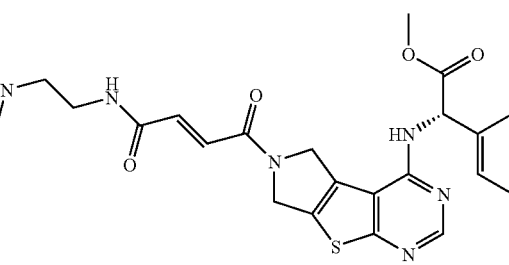

Compound 103
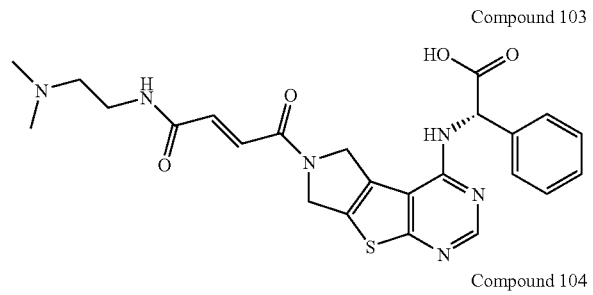
Compound 104
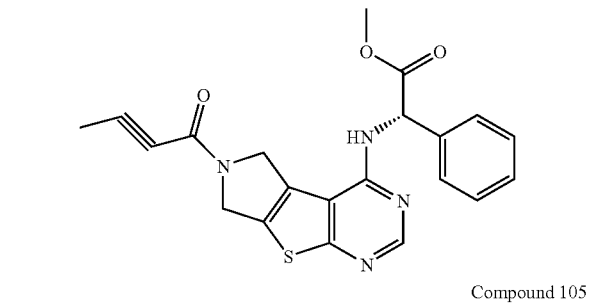
Compound 105
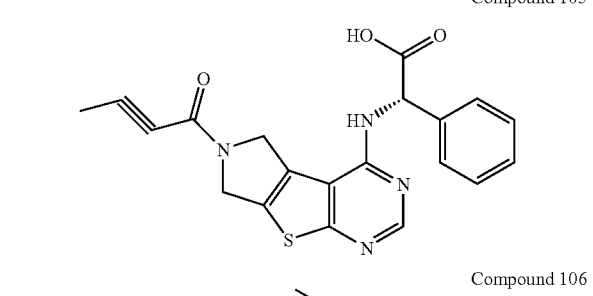
Compound 106
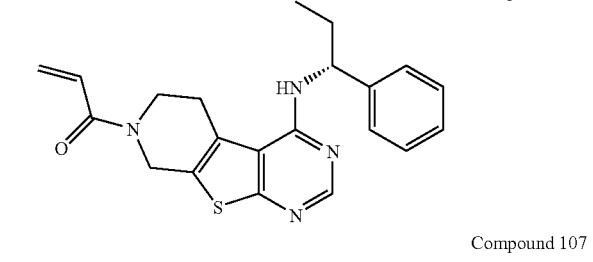
Compound 107
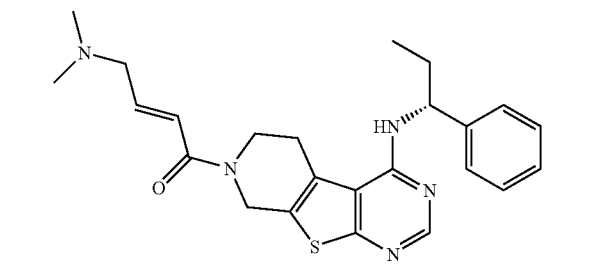
Compound 108
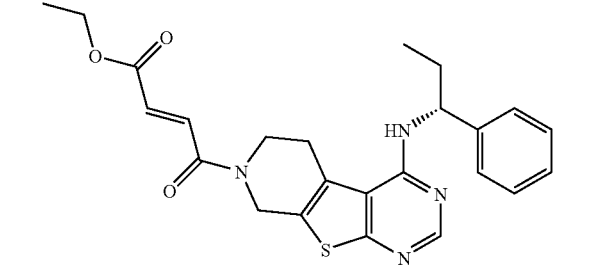
Compound 109
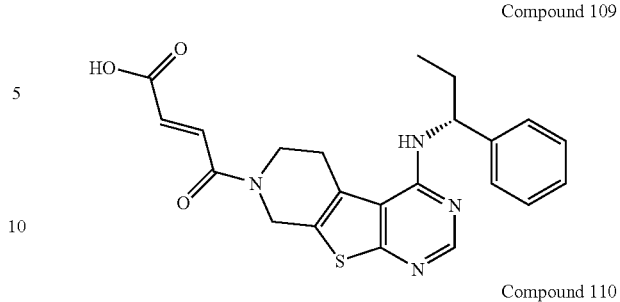
Compound 110
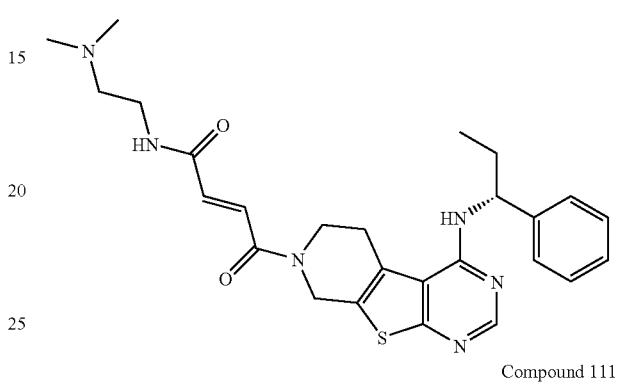
Compound 111
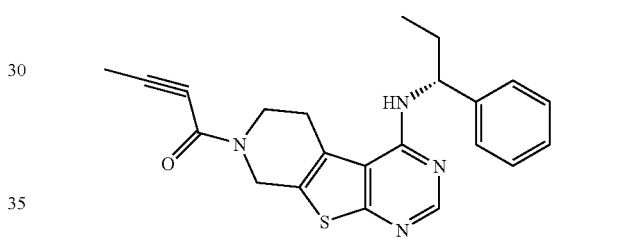
Compound 112
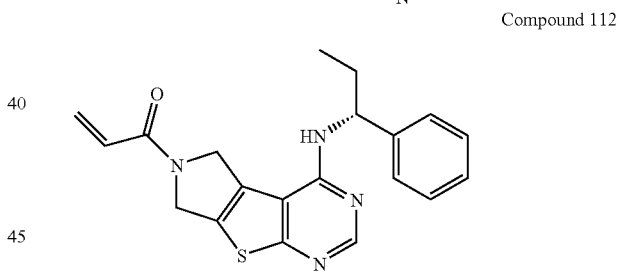
Compound 113
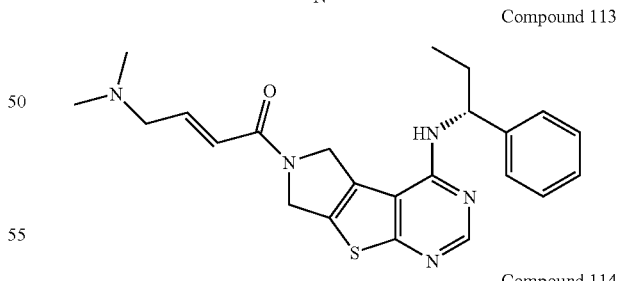
Compound 114
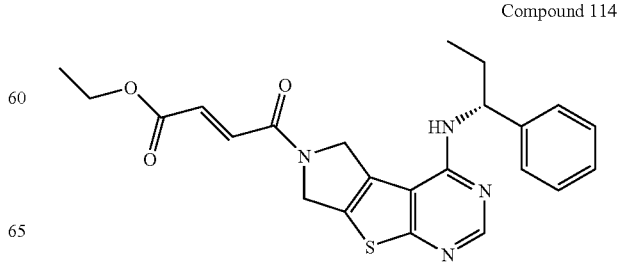

Compound 115
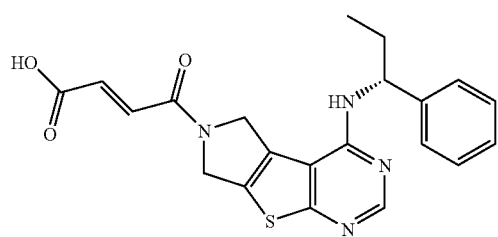
Compound 116
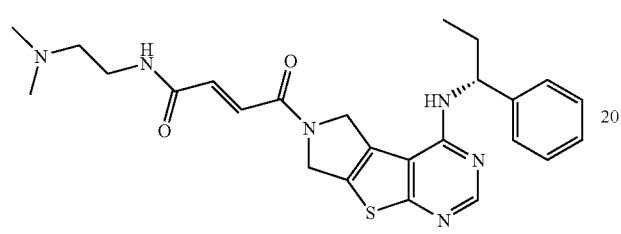
Compound 117
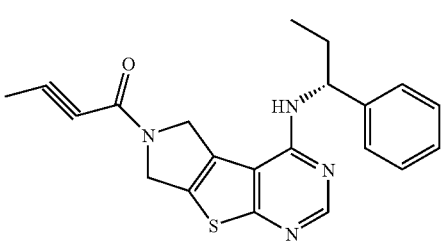
Compound 118
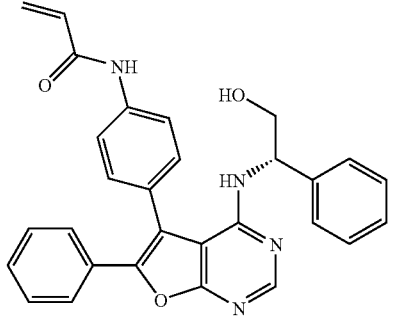
Compound 119
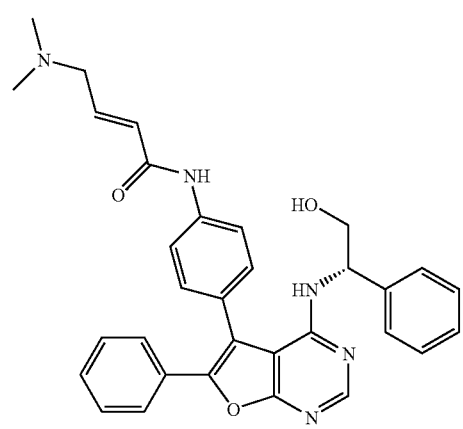
Compound 120
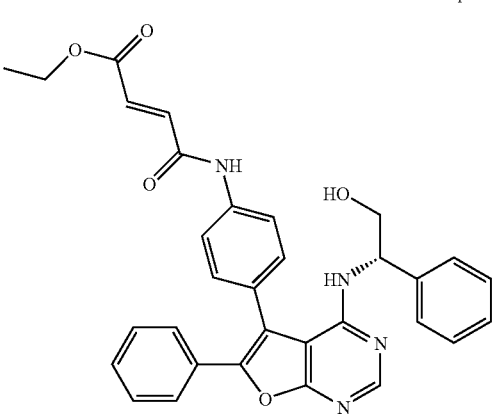
Compound 121
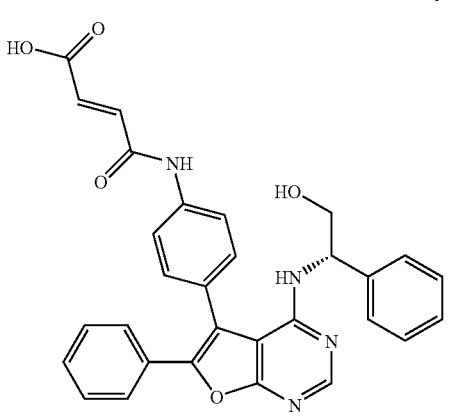
Compound 122
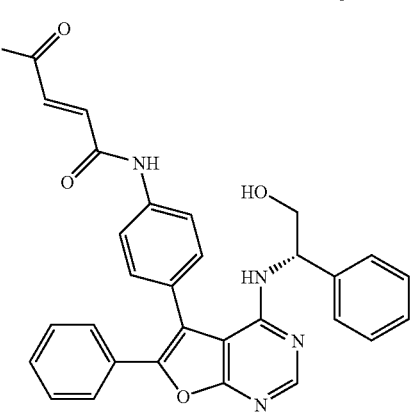
Compound 123
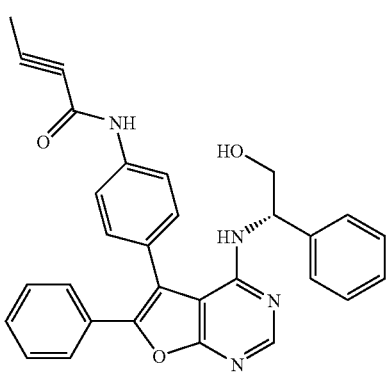

Compound 124
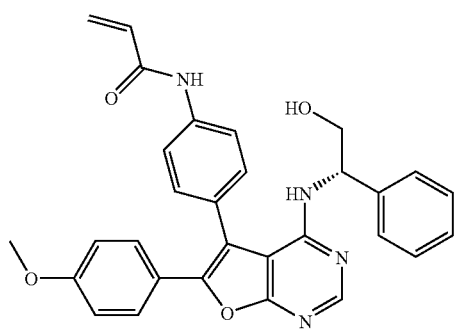
Compound 128
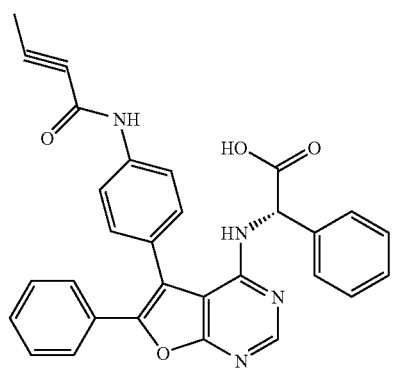
Compound 125
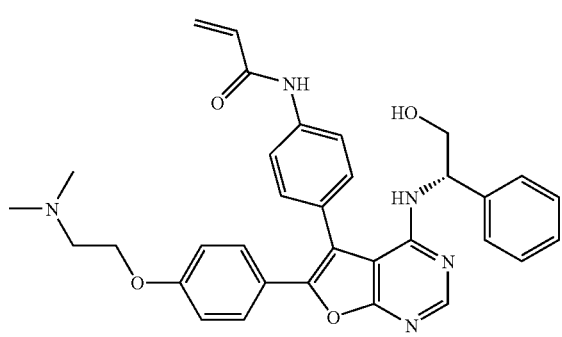
Compound 129
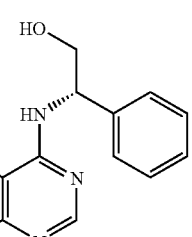
Compound 126
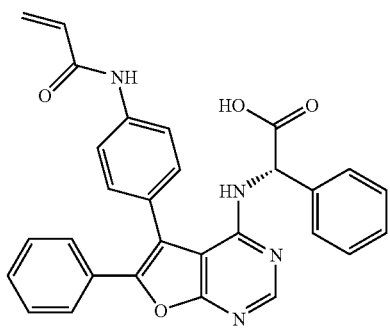
Compound 130
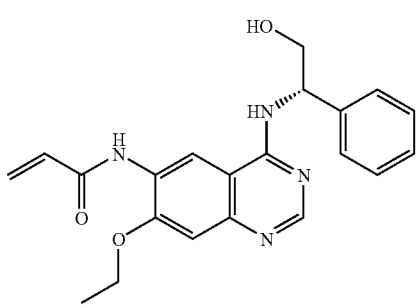
Compound 127
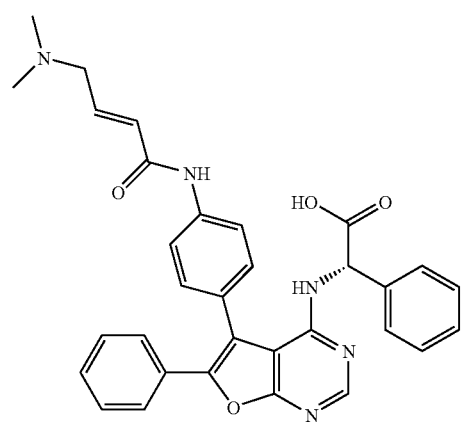
Compound 131
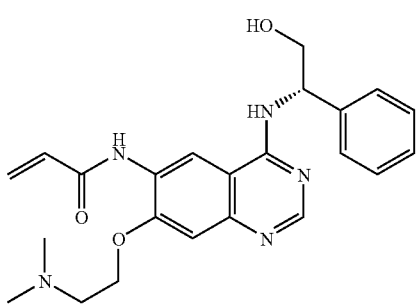
Compound 132
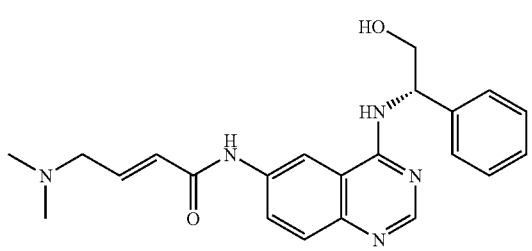

Compound 133
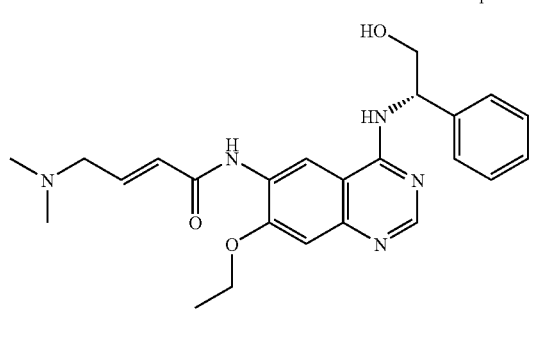
Compound 138
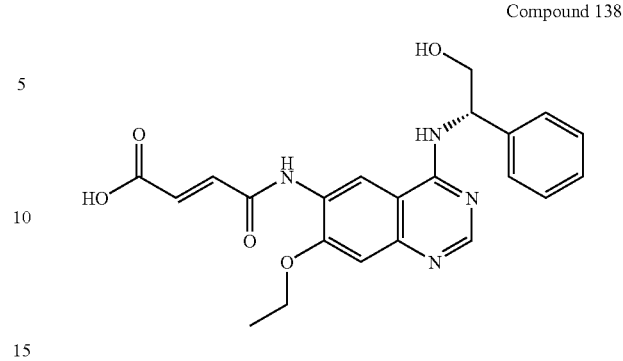
Compound 134
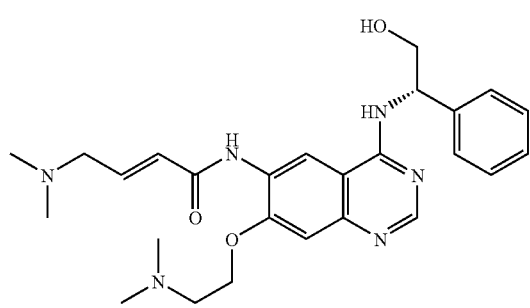
Compound 139
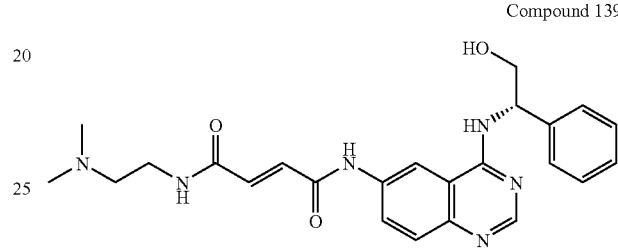
Compound 135
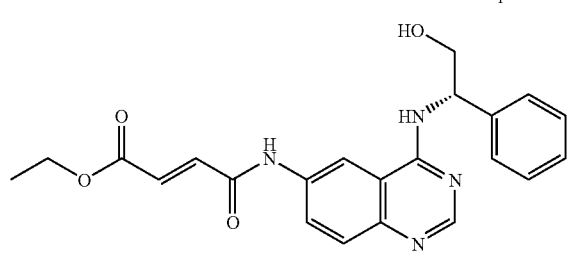
Compound 140
Compound 136
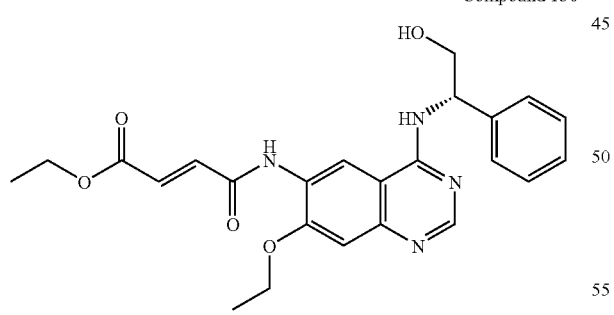
Compound 141
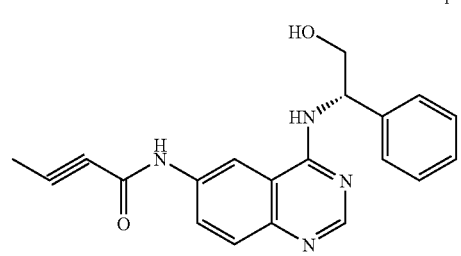
Compound 137
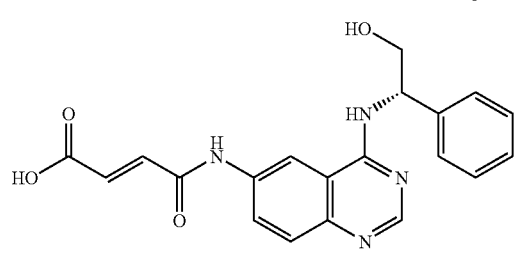
Compound 142

-continued
Compound 143
Compound 144
Compound 145
Compound 146
Compound 147
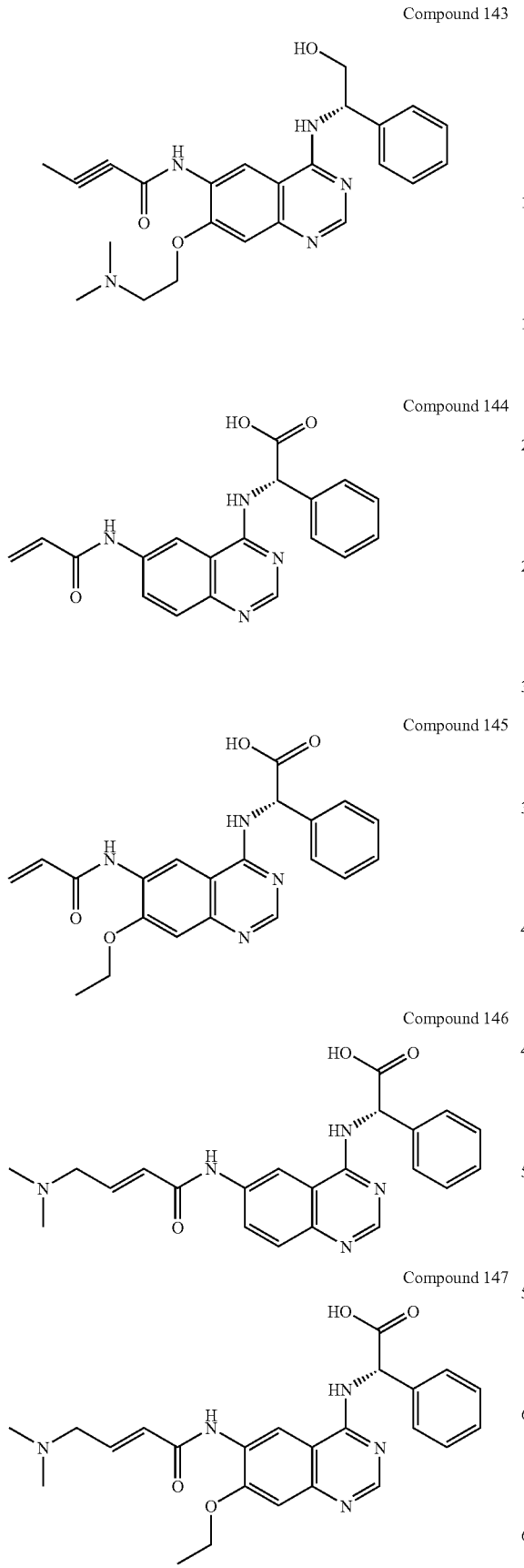
-continued
Compound 148
Compound 149
Compound 150
Compound 151
Compound 152
Compound 153
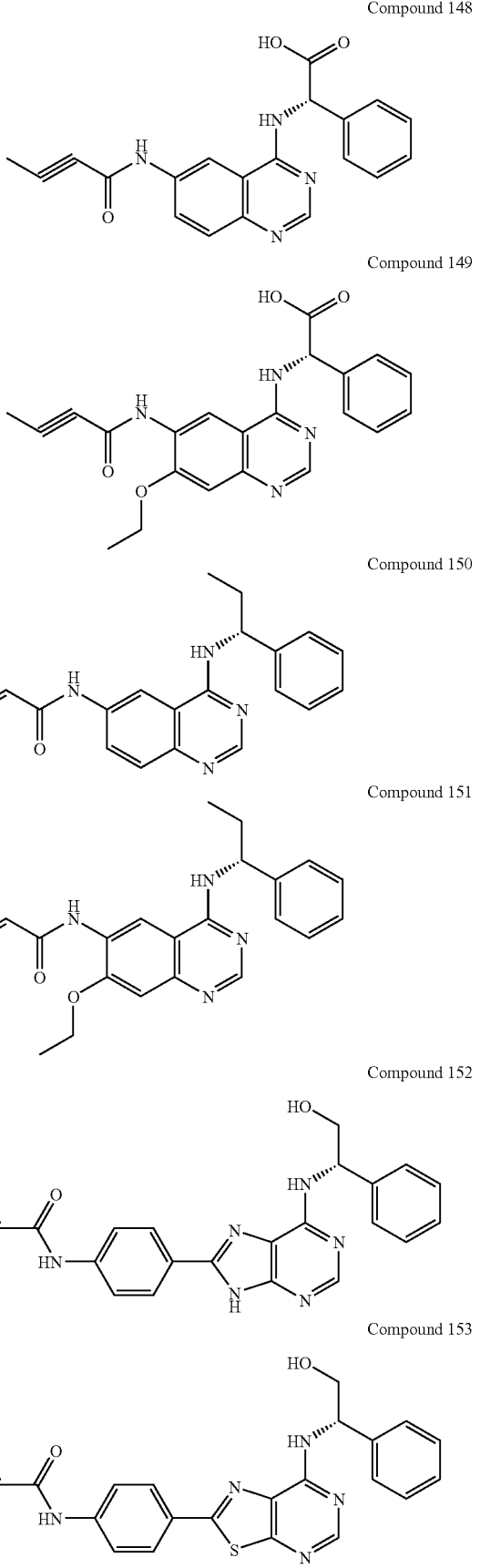

Compound 154
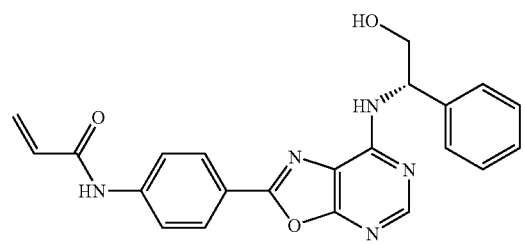
Compound 155
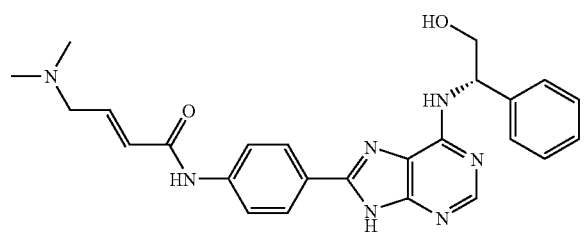
Compound 156
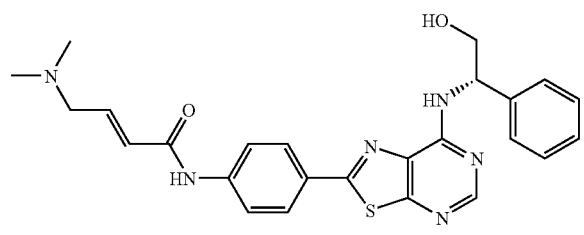
Compound 157
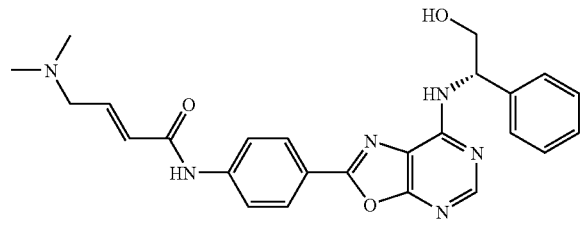
Compound 158
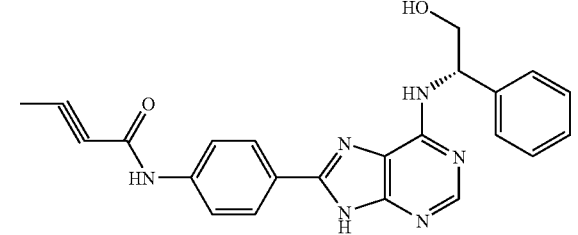
Compound 159
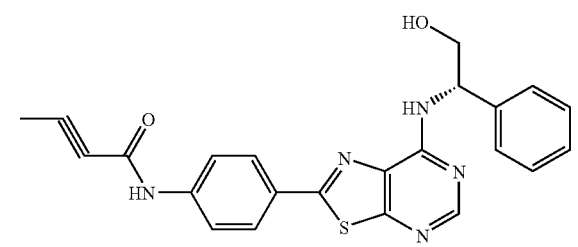
Compound 160
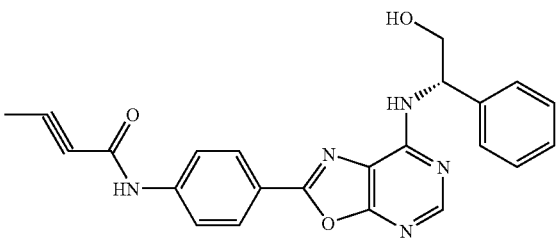
Compound 161
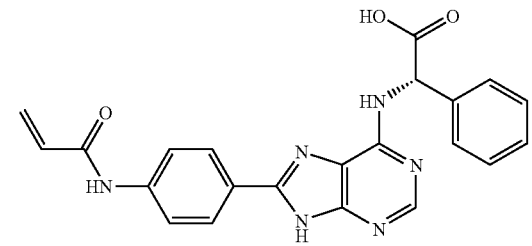
Compound 162
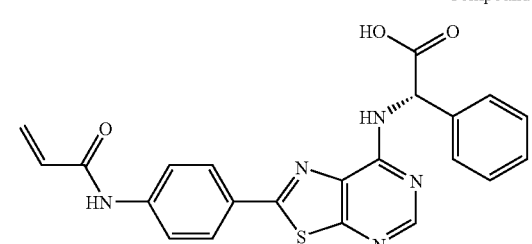
Compound 163
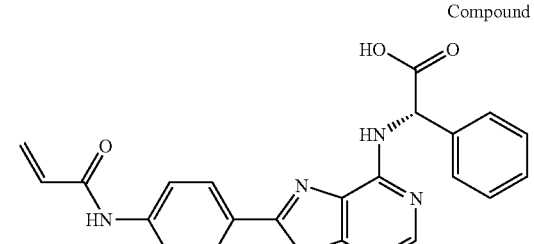
Compound 164
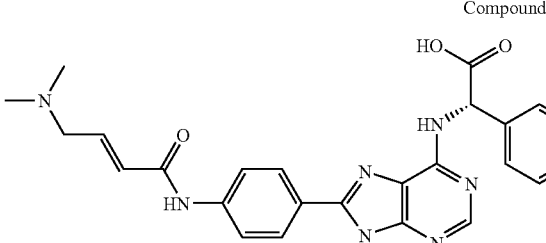
Compound 165
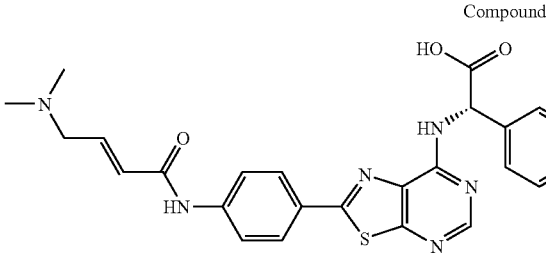

Compound 166
Compound 167
Compound 168
Compound 169
Compound 170
Compound 171
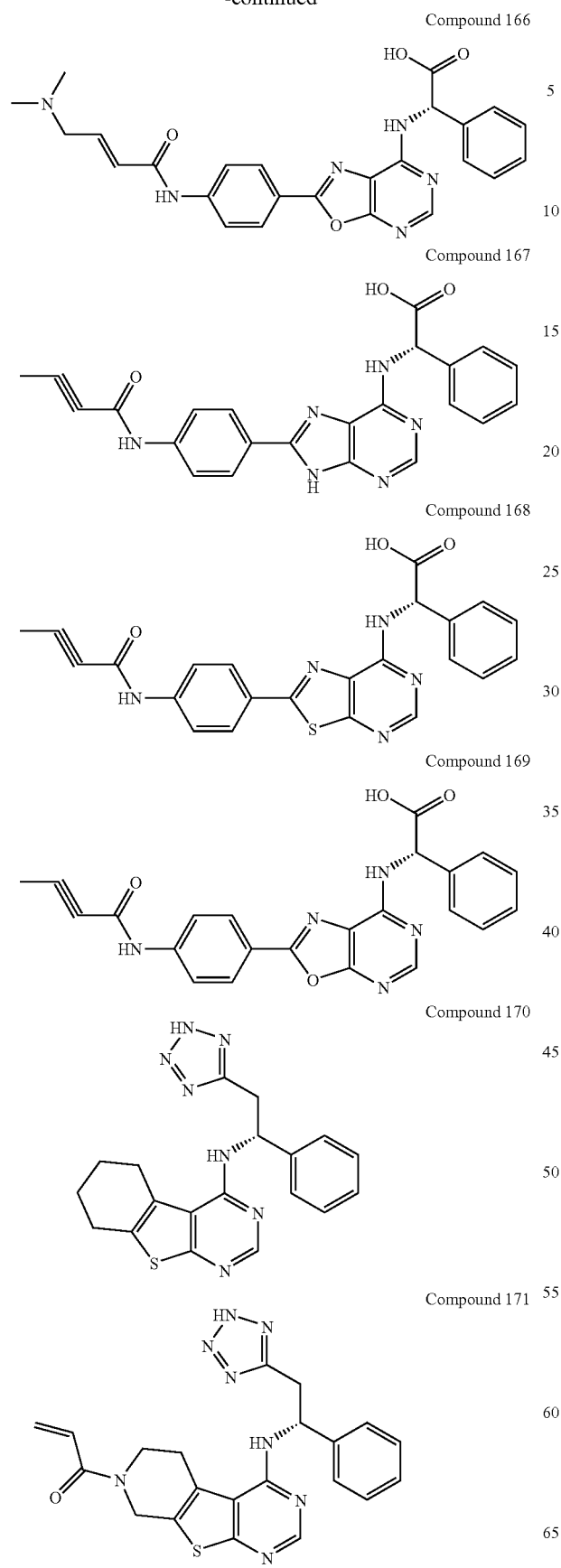
Compound 172
Compound 173
Compound 174
Compound 175
Compound 176
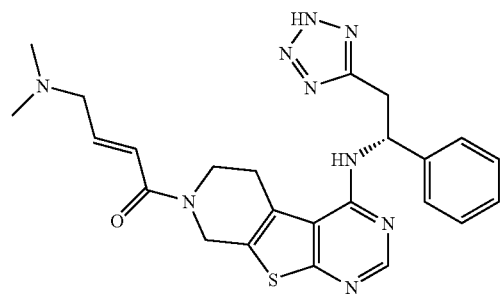
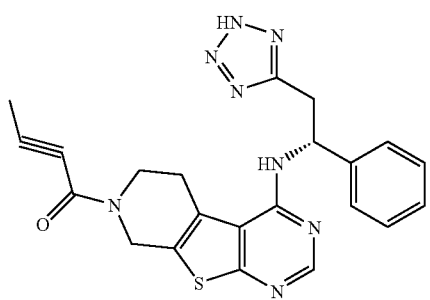
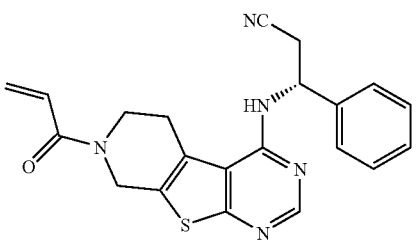
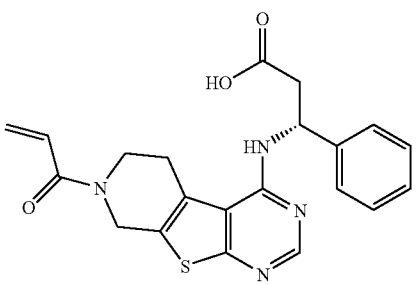
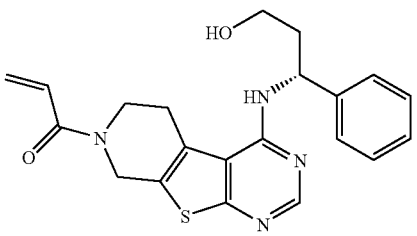

Compound 177
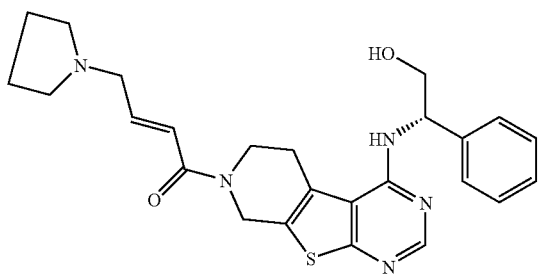
Compound 178
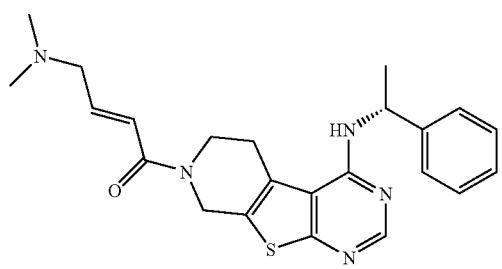
Compound 179
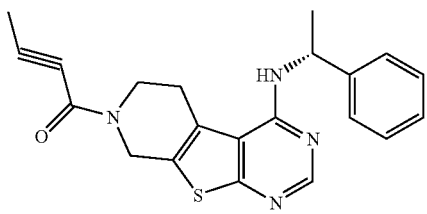
Compound 180
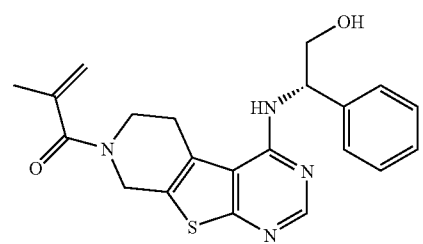
Compound 181
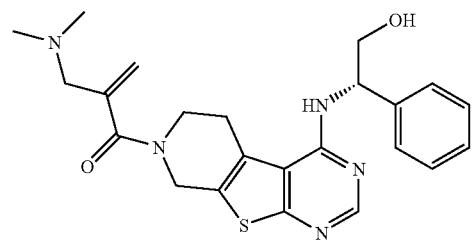
Compound 182
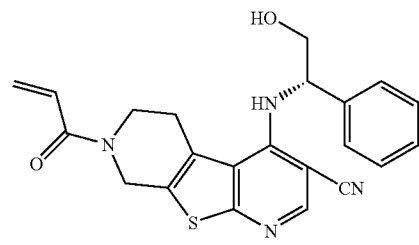
Compound 183
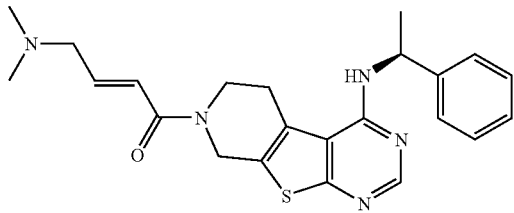
Compound 184
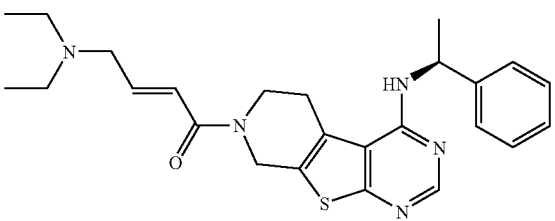
Compound 185
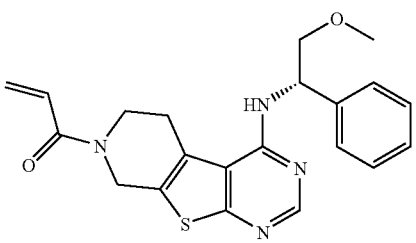
Compound 186
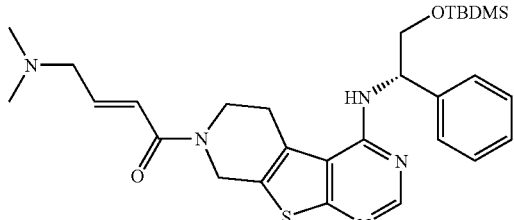
Compound 187
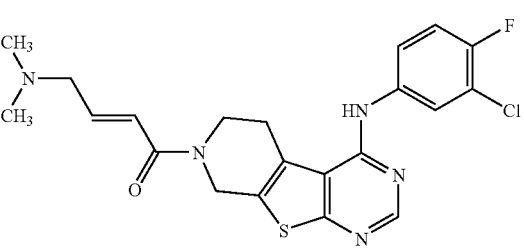
Compound 188
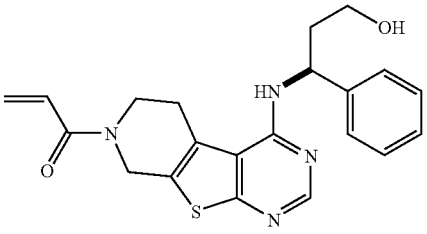

-continued
Compound 189
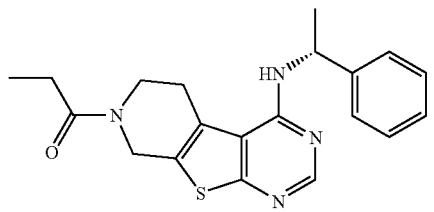
Compound 190
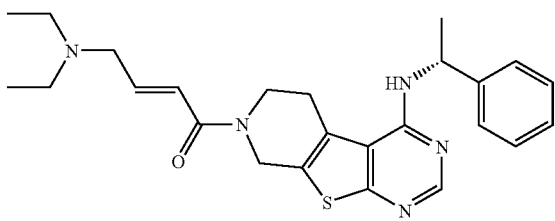
Compound 191
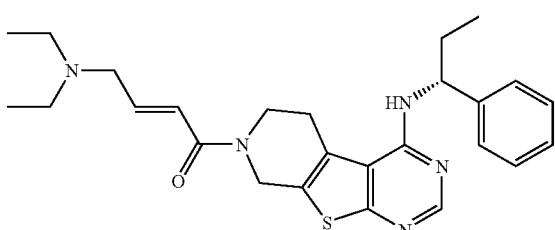
Compound 192
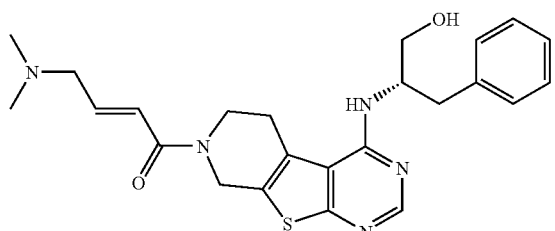
Compound 193
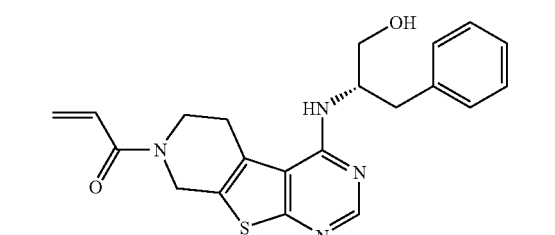
Compound 194
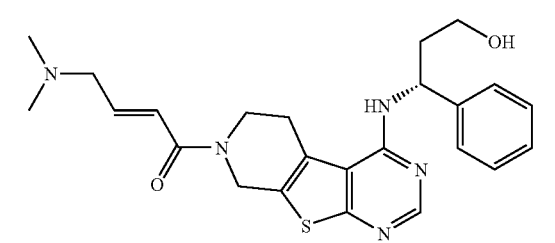
-continued
Compound 195
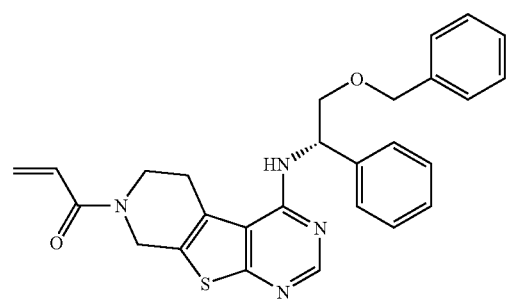
Compound 196
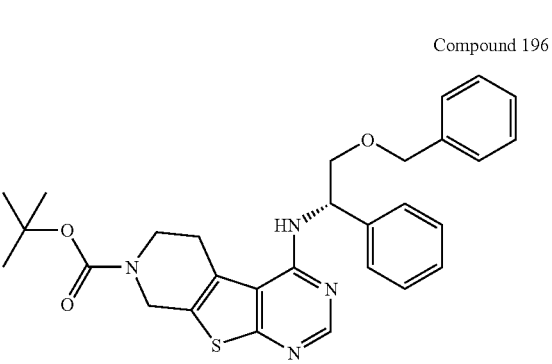
Compound 197
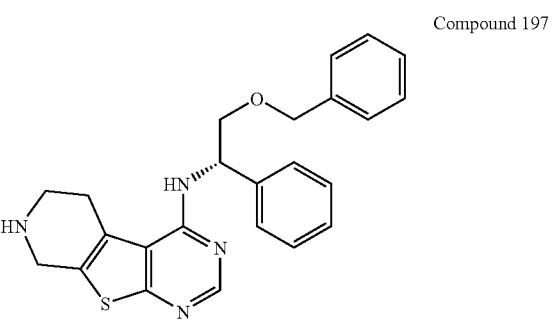
Compound 198
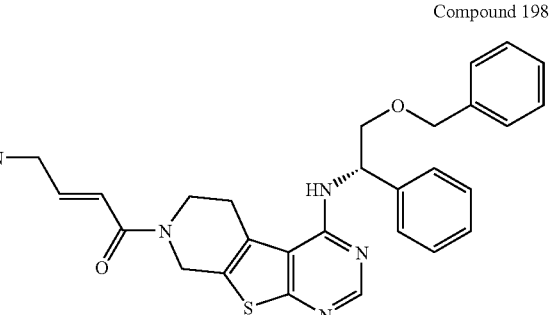
Compound 199
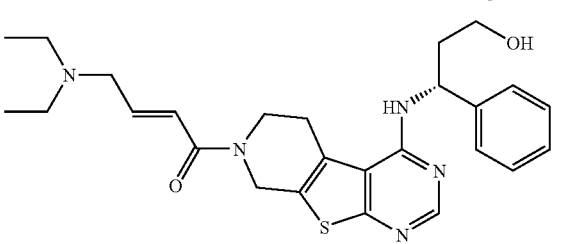

Compound 200
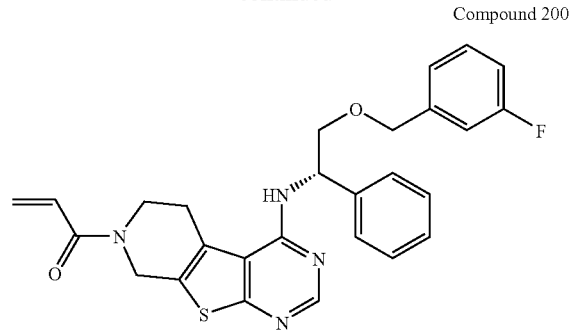
Compound 201
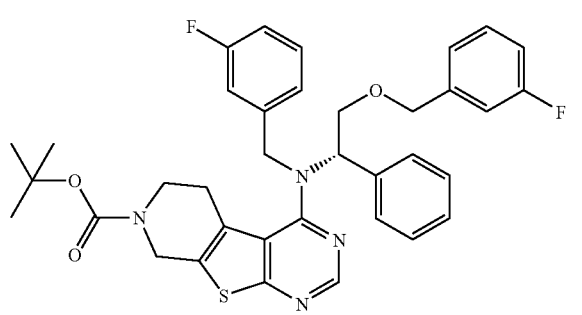
Compound 202
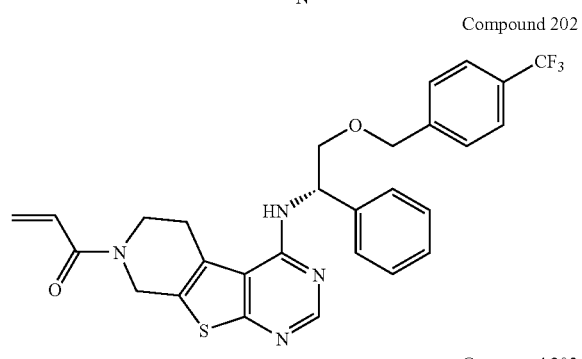
Compound 203
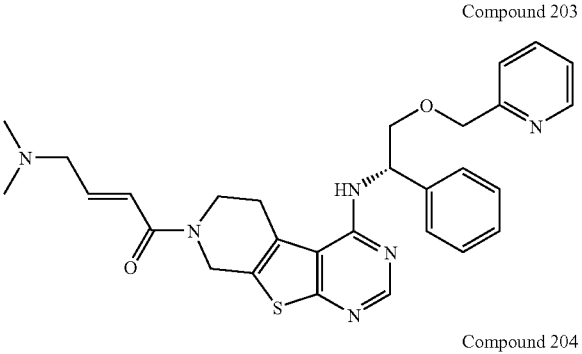
Compound 204
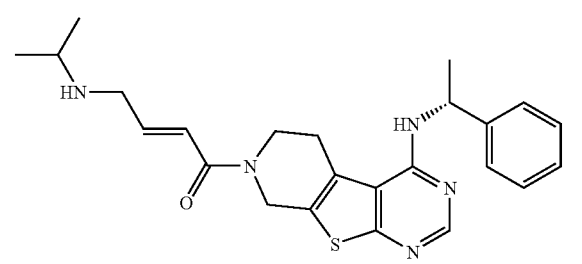
Compound 205
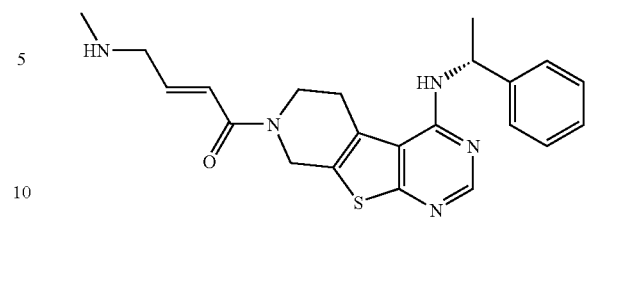
Compound 206
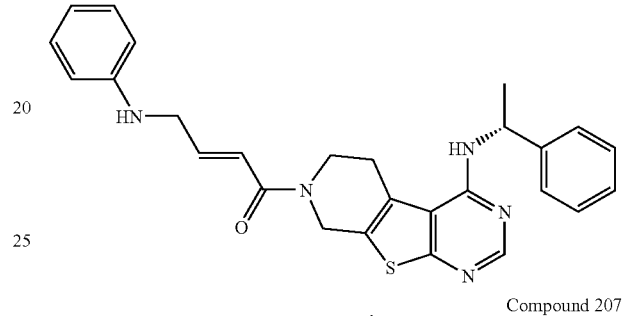
Compound 207
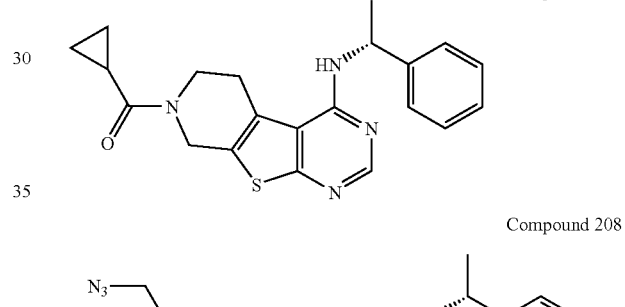
Compound 208
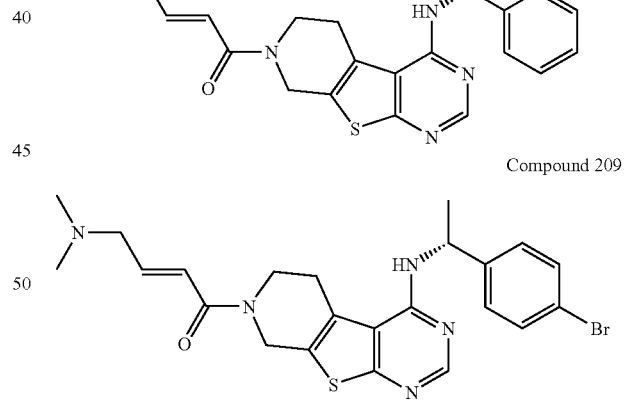
Compound 209
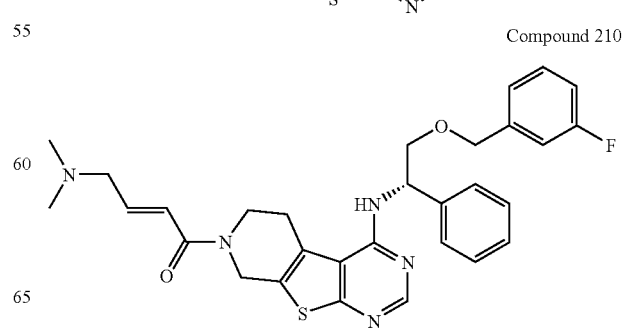
Compound 210
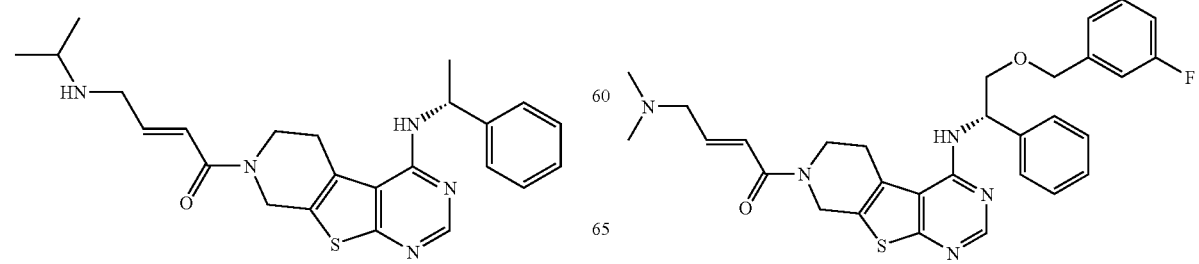

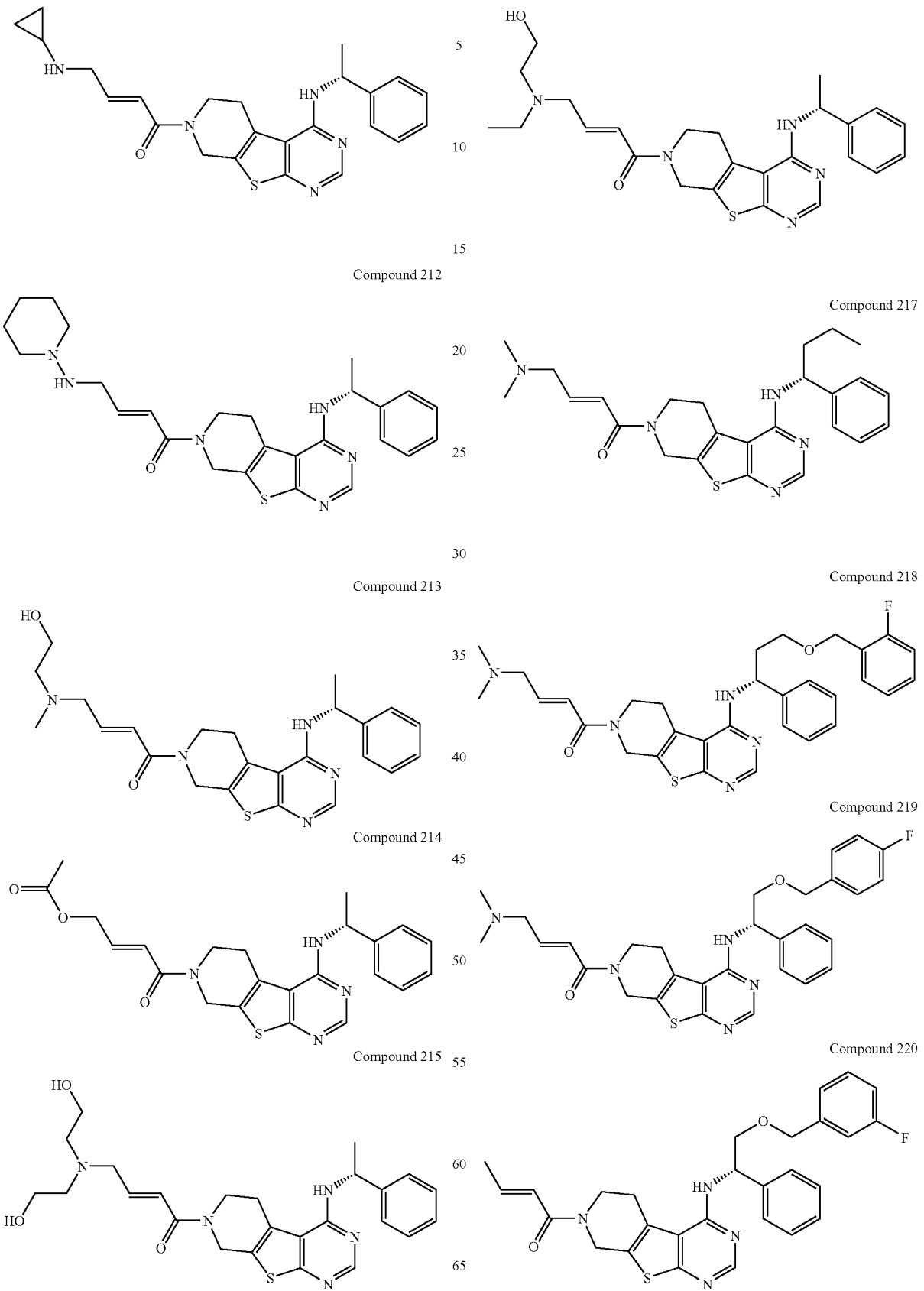

Compound 221
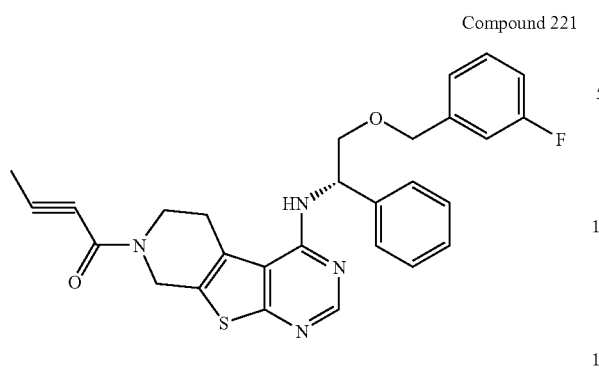
Compound 226
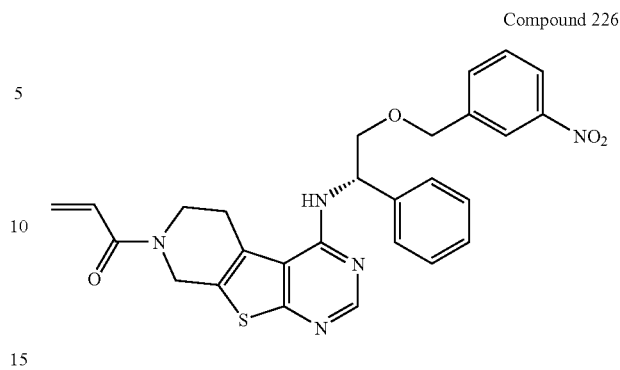
Compound 222
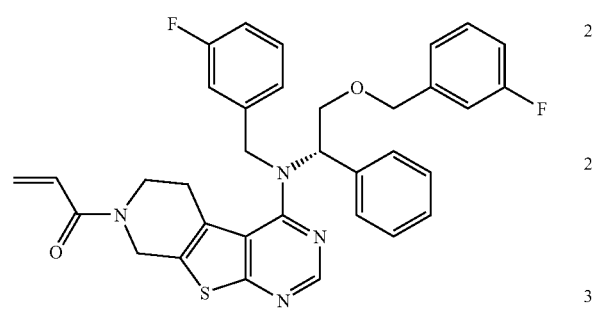
Compound 227
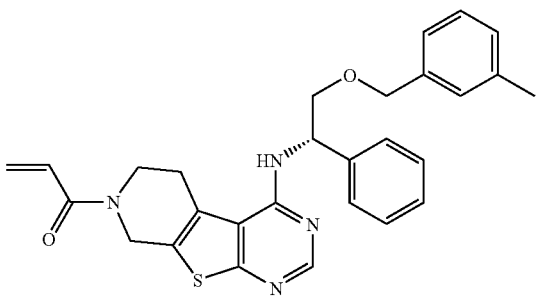
Compound 223
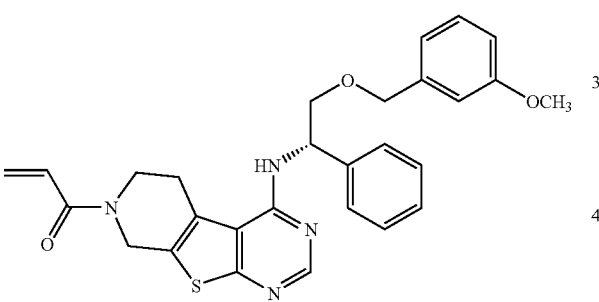
Compound 228
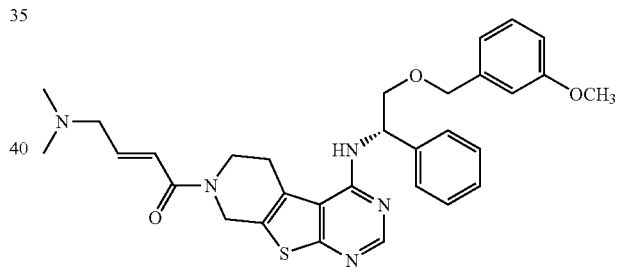
Compound 224
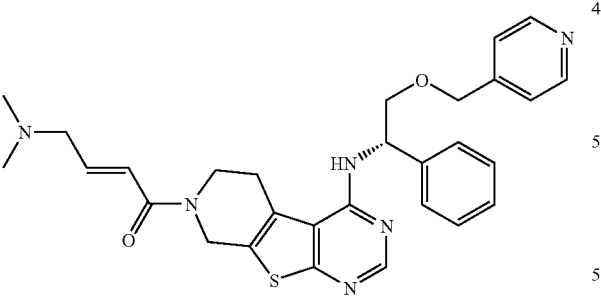
Compound 229
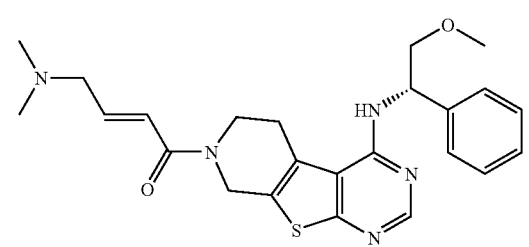
Compound 225
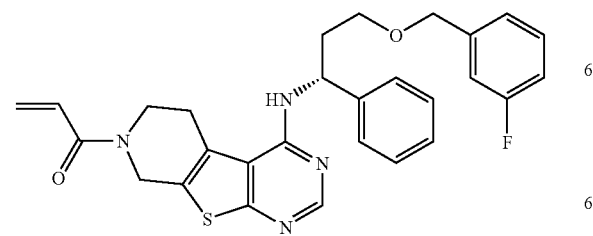
Compound 230
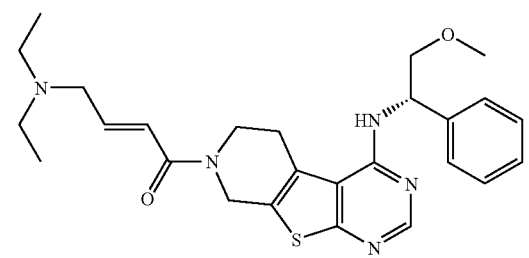

Compound 231
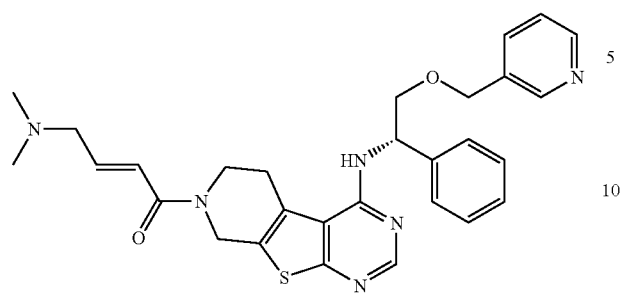
Compound 232
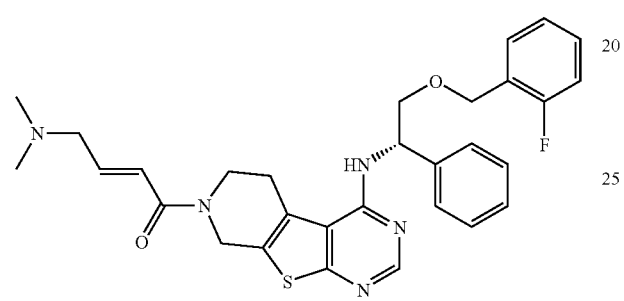
Compound 233
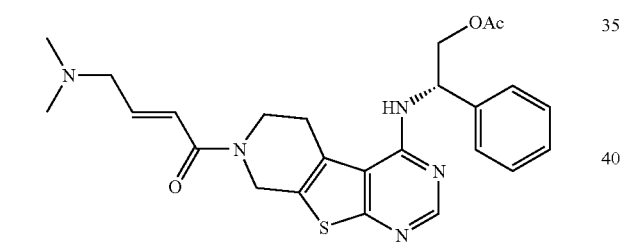
Compound 234
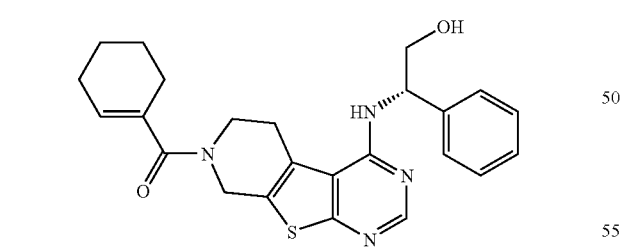
Compound 235
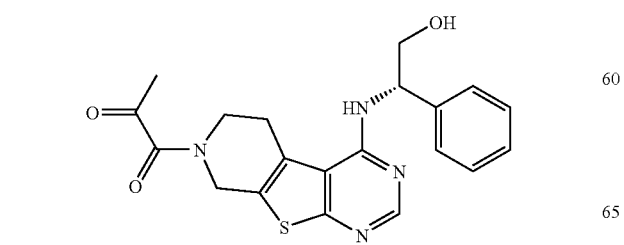
Compound 236
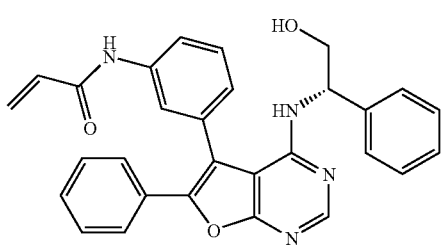
Compound 237
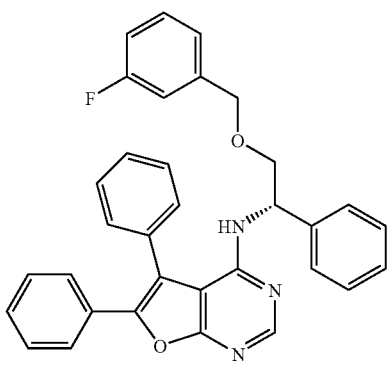
Compound 238
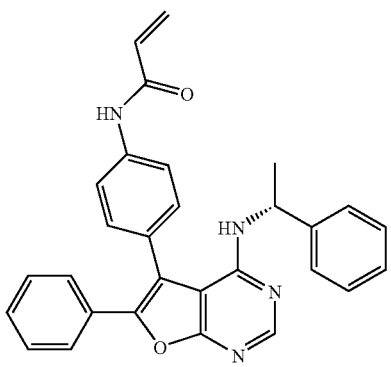
Compound 239
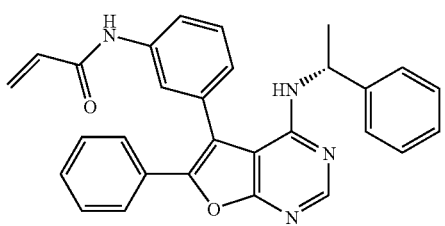
Compound 240
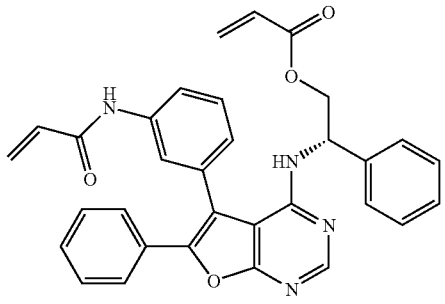

Compound 241
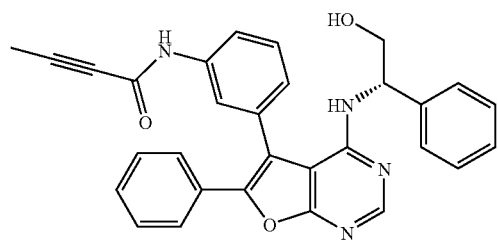
Compound 242
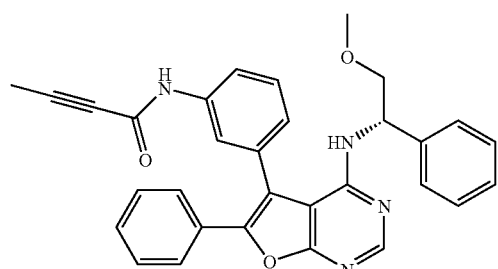
Compound 243
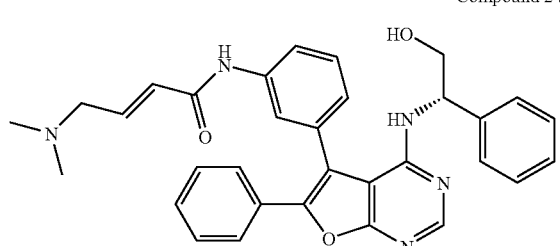
Compound 244
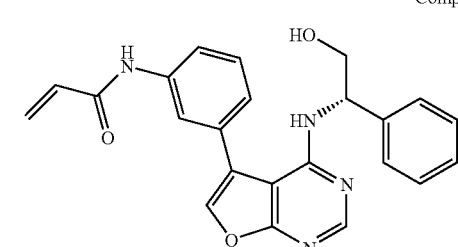
Compound 245
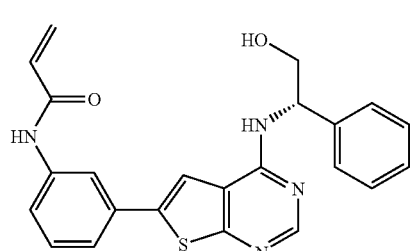
Compound 246
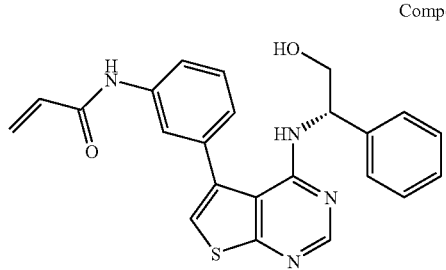
Compound 247
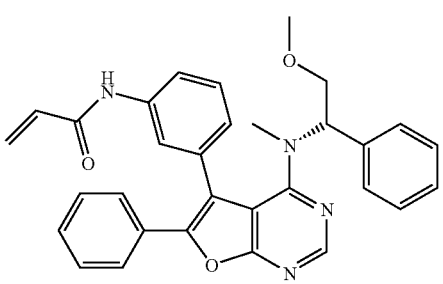
Compound 248
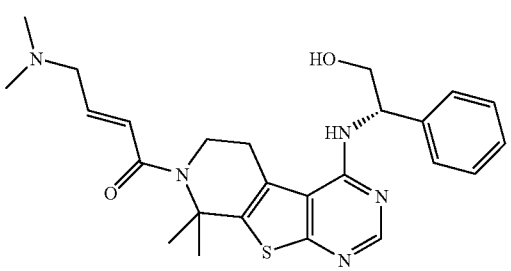
Compound 249
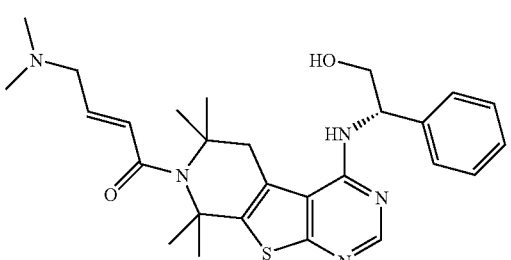
Compound 250
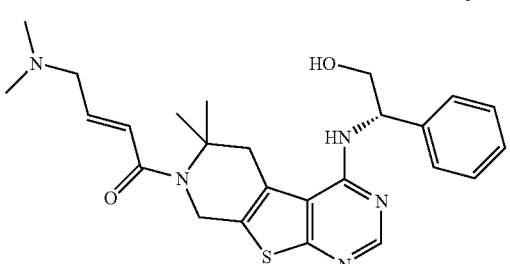
Compound 251
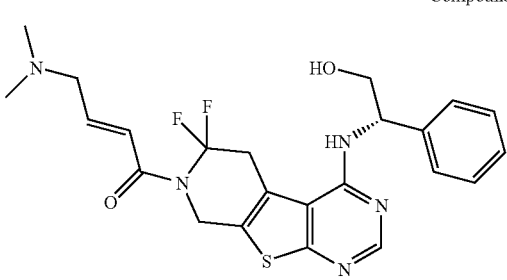

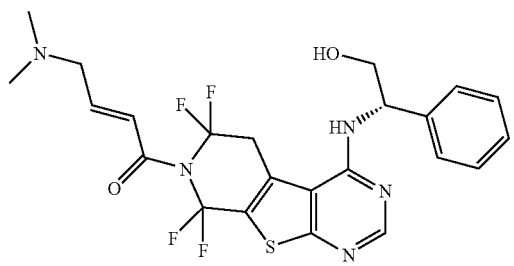
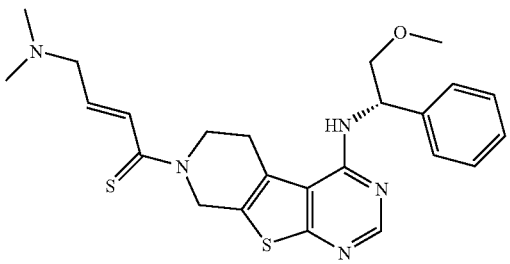

Compound 262
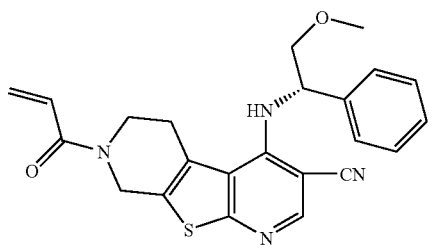
Compound 263
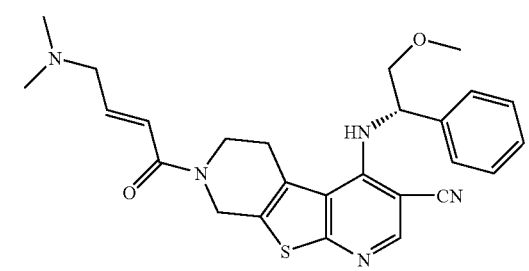
Compound 264
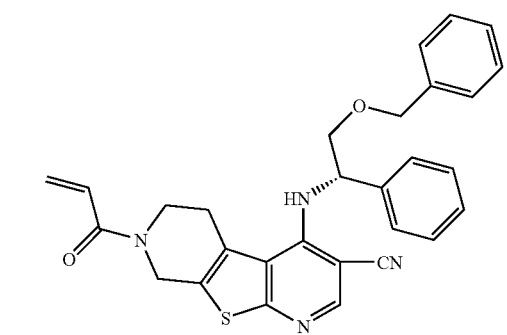
Compound 265
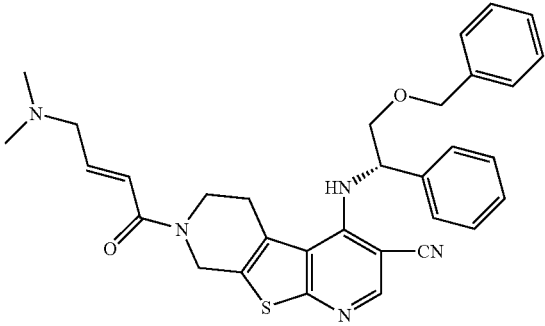
Compound 266
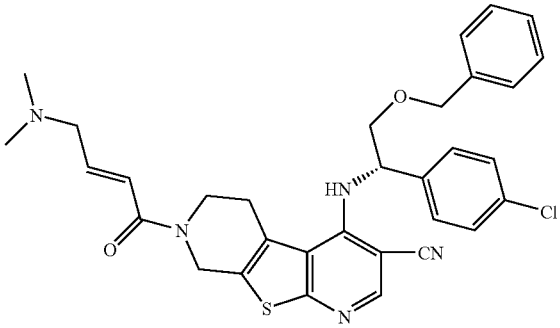
Compound 267
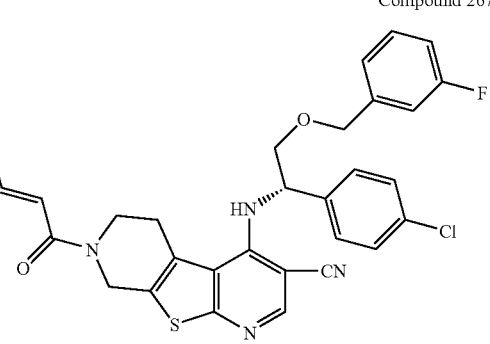
Compound 268
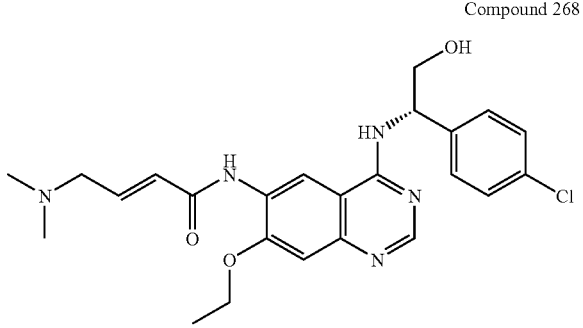
Compound 269
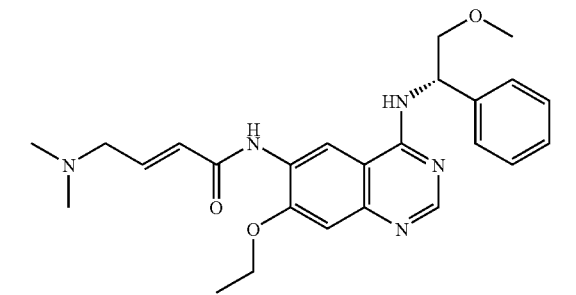
Compound 270
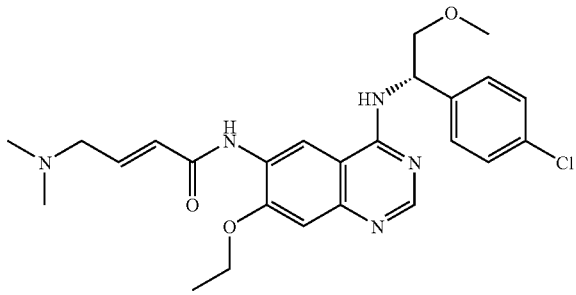
Compound 271
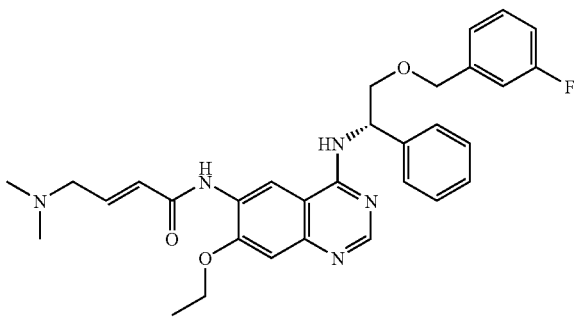

Compound 272
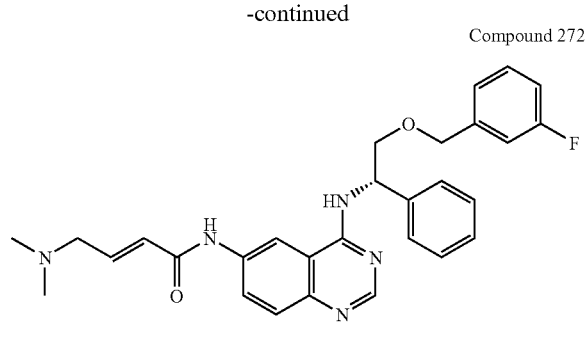
Compound 273
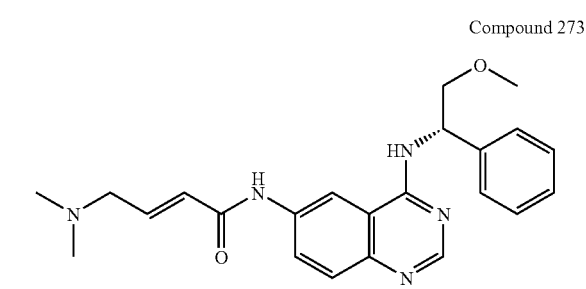
Compound 274
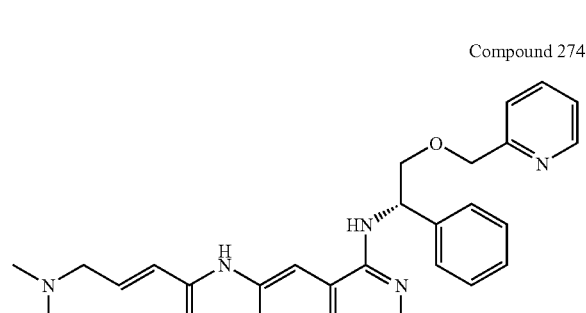
Compound 275
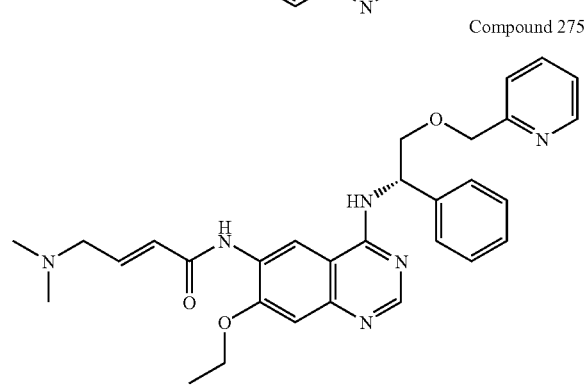
Compound 276
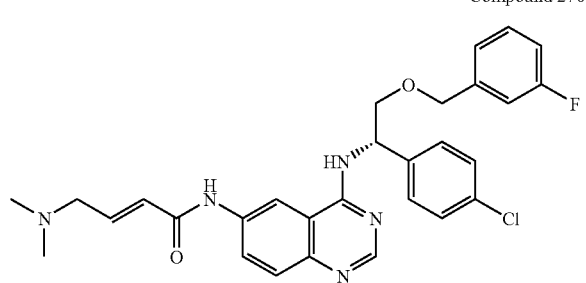
Compound 277
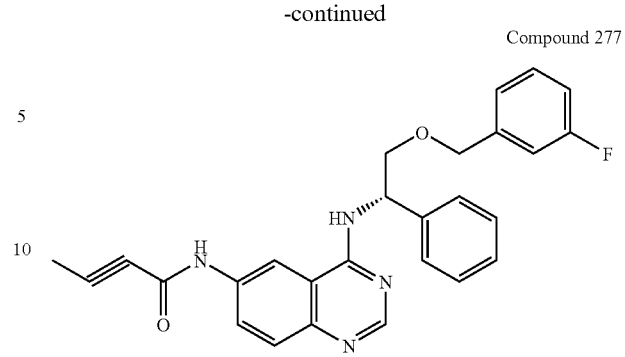
Compound 278
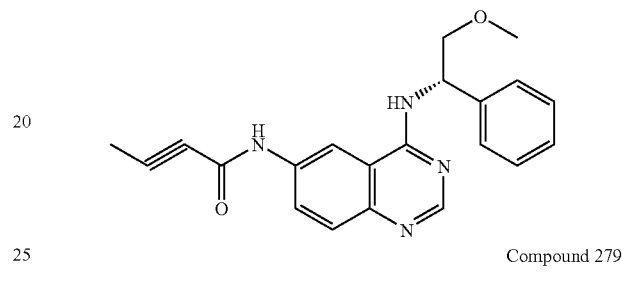
Compound 279
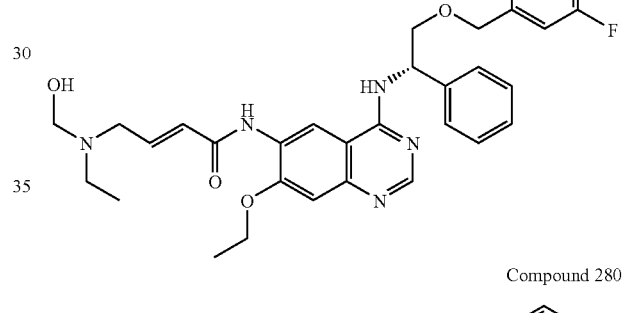
Compound 280
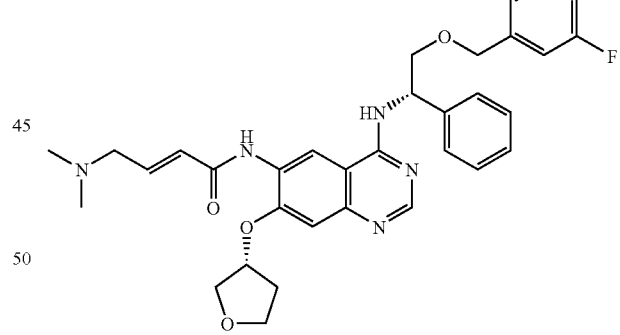
Compound 281
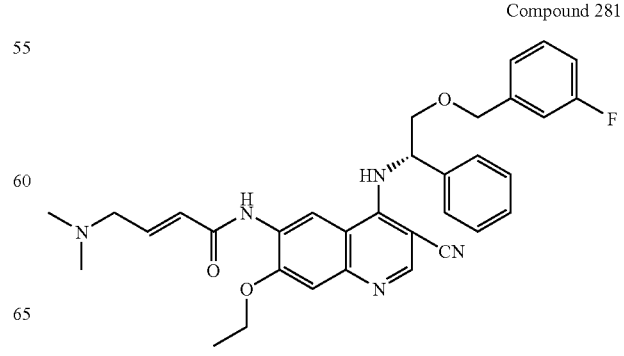

-continued
Compound 282
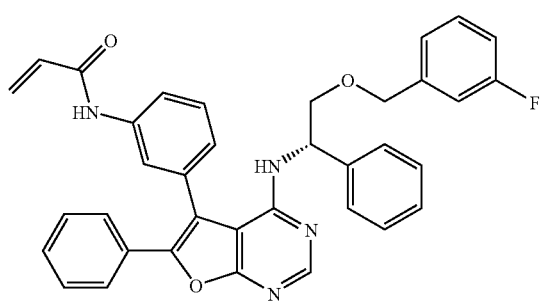
Compound 283
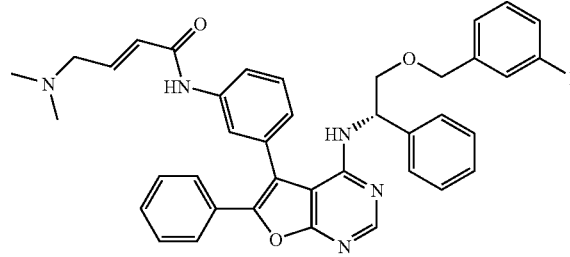
Compound 284
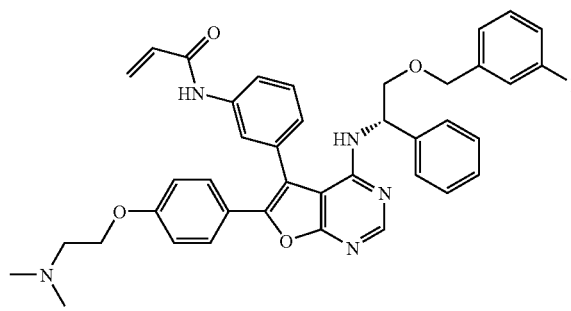
Compound 285
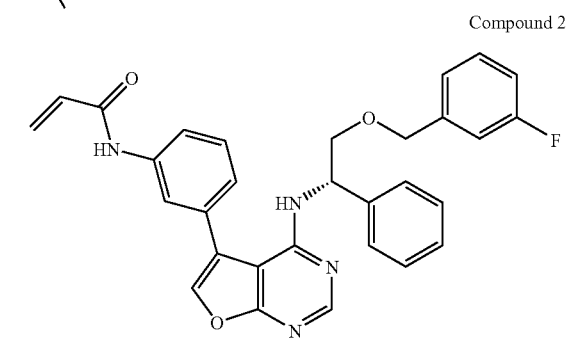
Compound 286
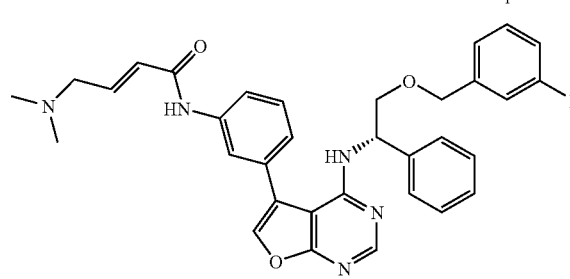
-continued
Compound 287
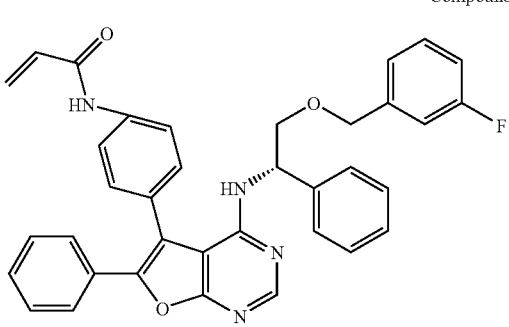
Compound 288
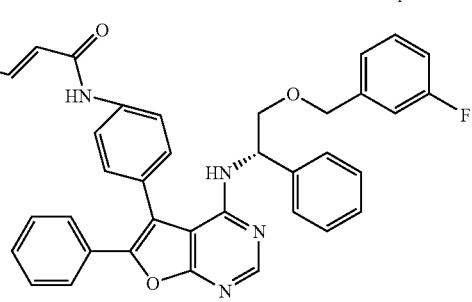
Compound 289
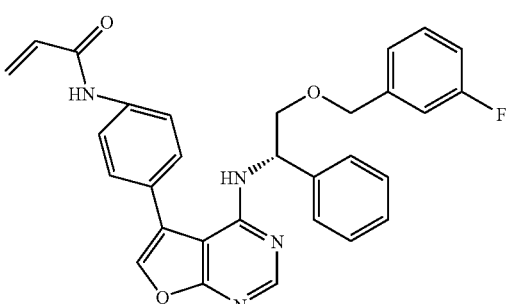
Compound 290
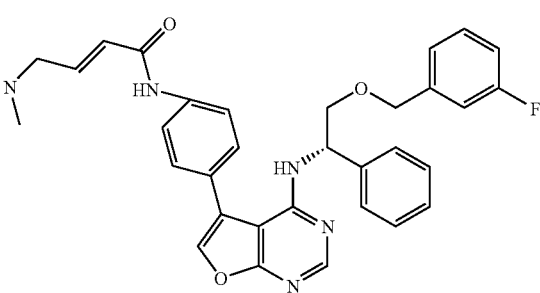
Compound 291
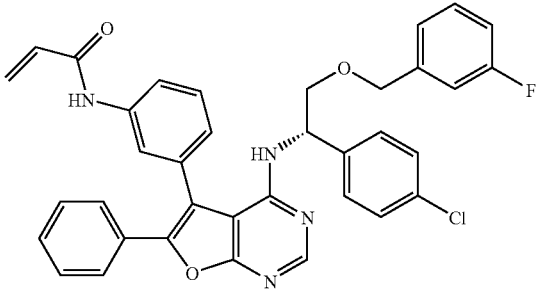

Compound 292
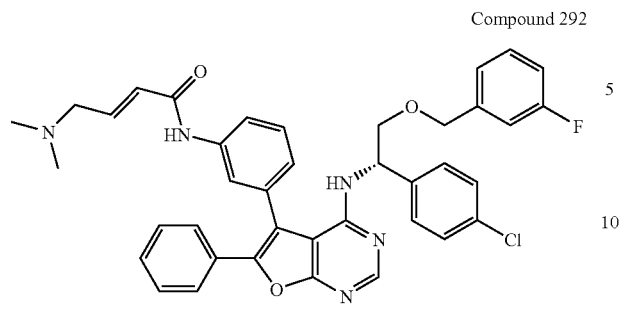
Compound 293
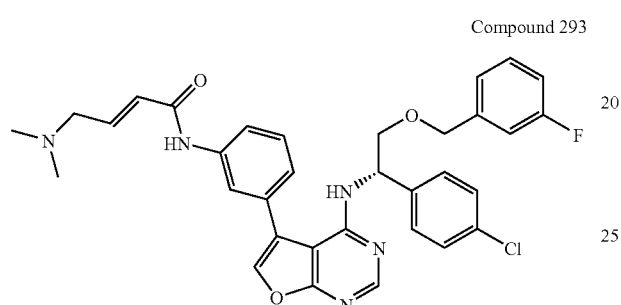
Compound 294
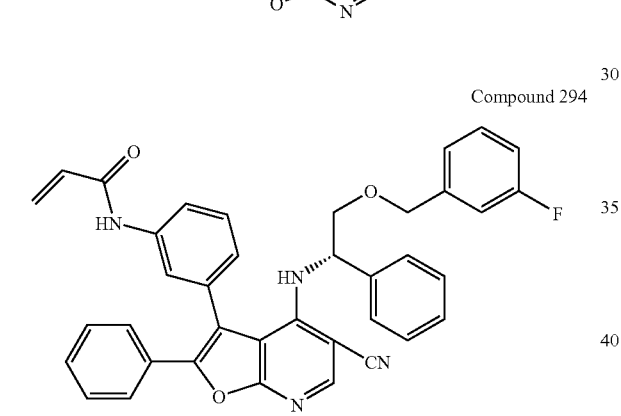
Compound 295
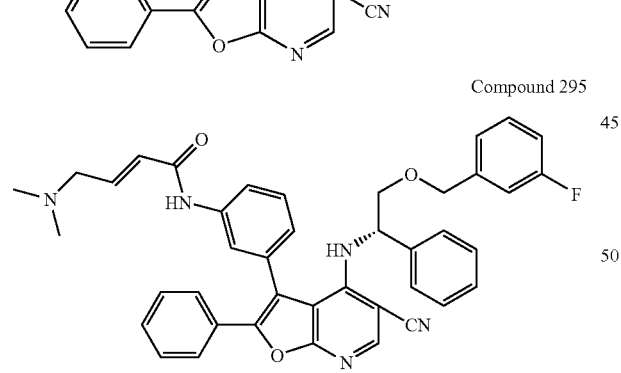
Compound 296
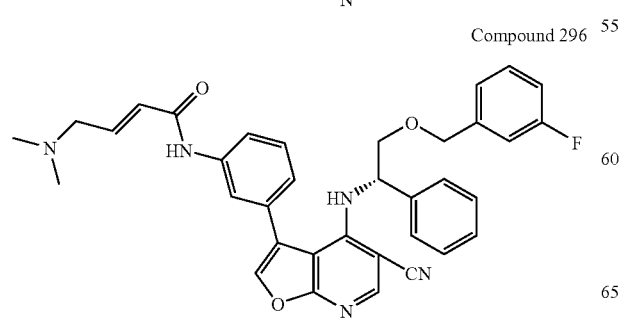
Compound 297
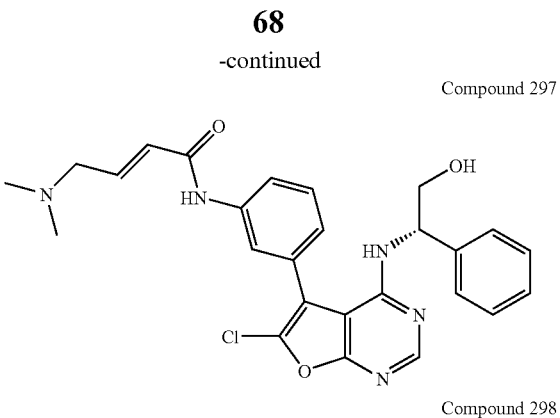
Compound 298
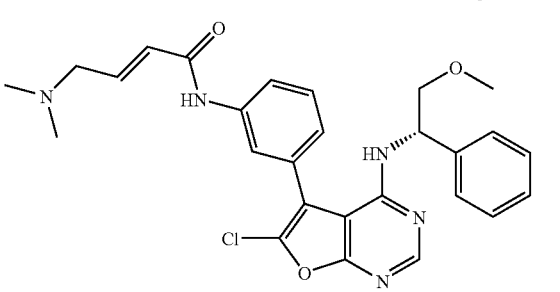
Compound 299
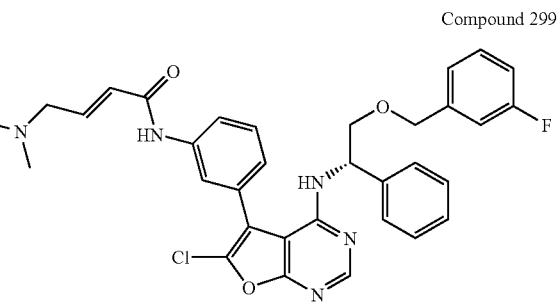
Compound 300
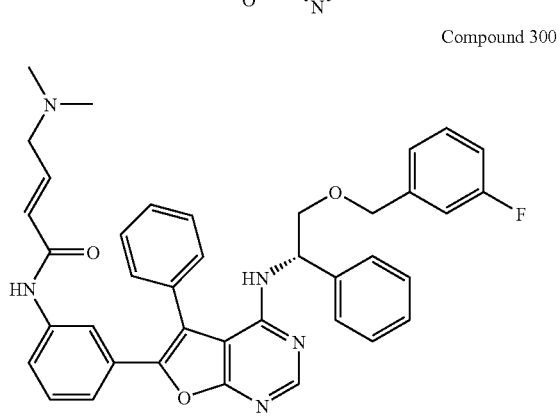
Compound 301
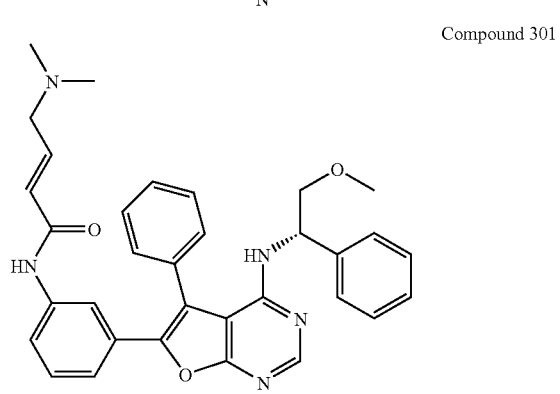

Compound 302
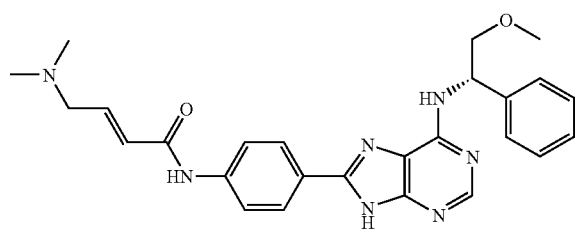
Compound 303
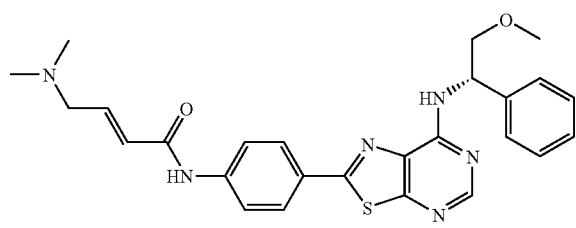
Compound 304
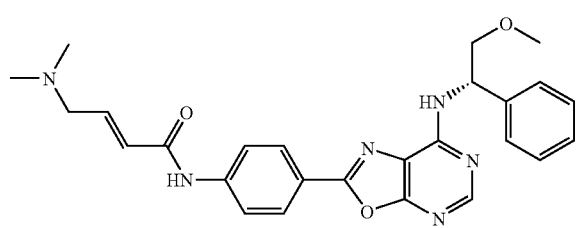
Compound 305
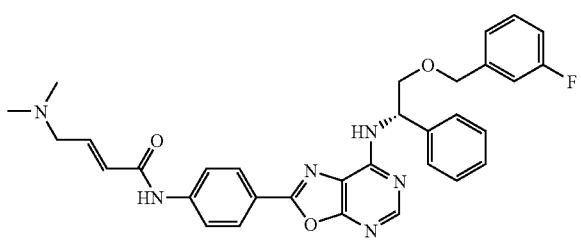
Compound 306
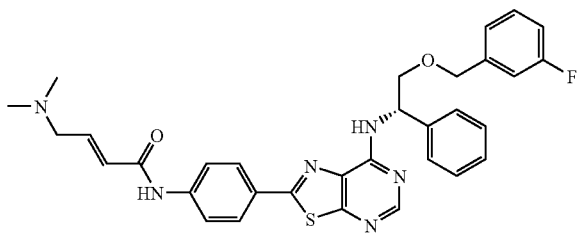
Compound 307
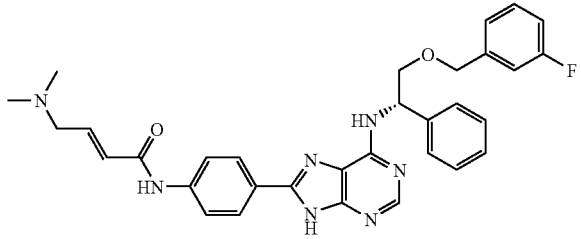
Compound 308
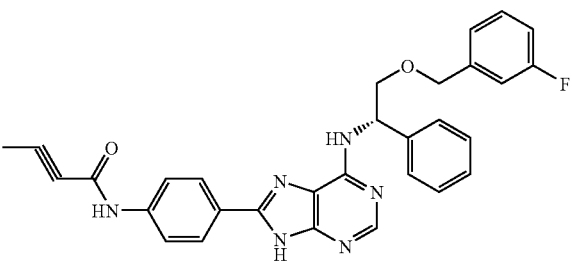
Compound 309
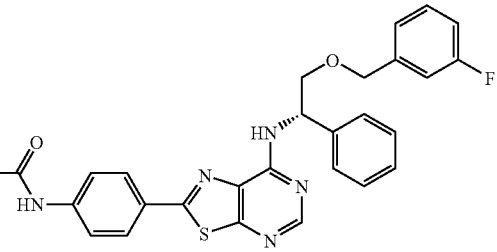
Compound 310
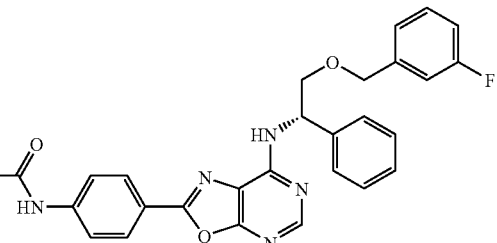
Compound 311
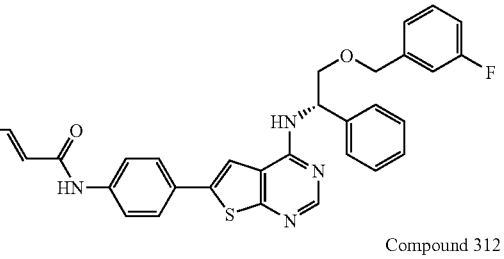
Compound 312
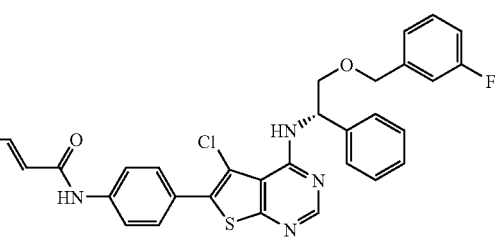
Compound 313
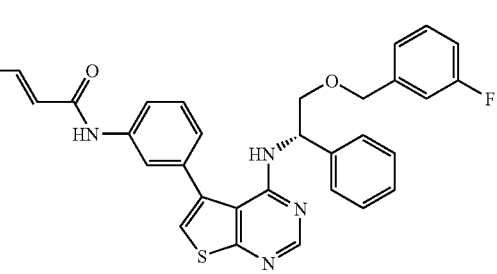

Compound 314
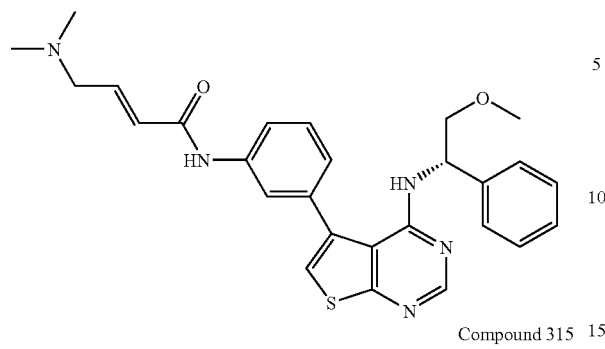
Compound 315
Compound 316
Compound 317
Compound 318
Compound 319
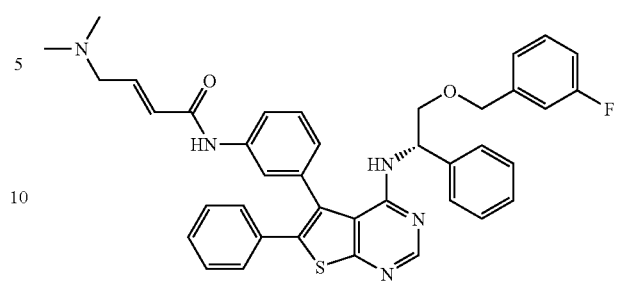
Compound 320
Compound 321
Compound 322
Compound 323

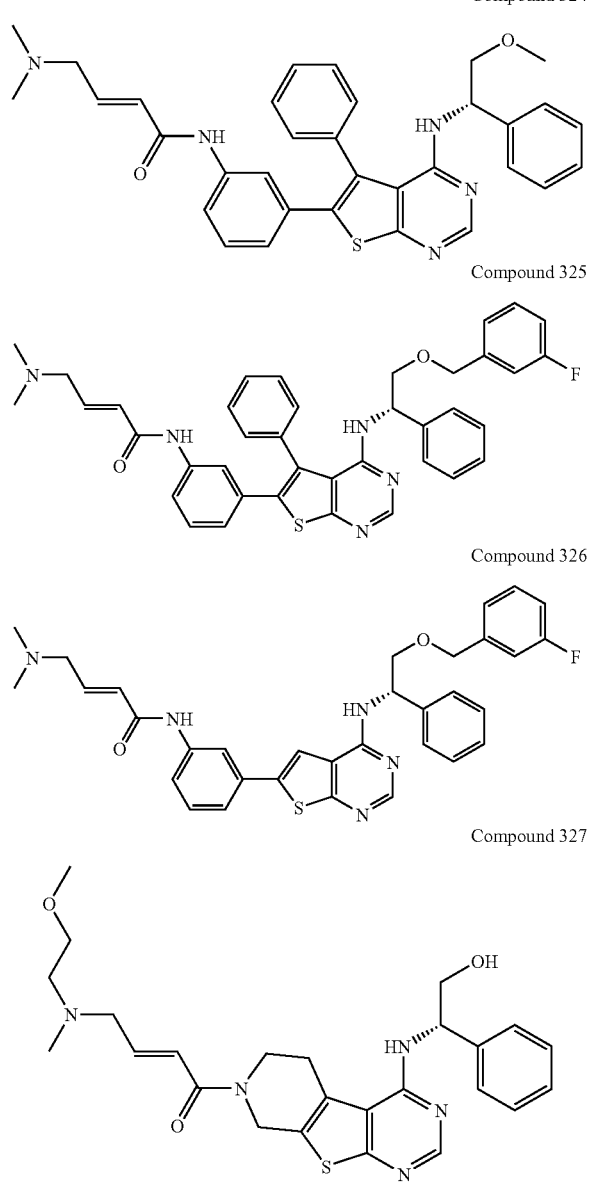

Compound 324

Compound 325

Compound 326

Compound 327

The fused bicyclic or tricyclic compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1-4 below show transformations for synthesizing compounds of this invention.

The route shown in Scheme 1 exemplifies the synthesis of thienopyrimidine compounds (VII) of the present invention. Triethylamine is added to a mixture of an appropriately substituted ketone (I), malanonitrile (II), and sulphur ($S_8$) in absolute ethanol. The resulting mixture is refluxed for 16 h, then concentrated. The residue is partitioned between water and ethyl acetate. The organic layer is concentrated and the residue is purified by silica gel chromatography to provide the thiophene compound (III). Subsequently, HCl is added to a mixture of the thiophene (III) and formic acid and the resulting mixture is refluxed for 16 h. Water is added and the precipitate formed is filtered to give the thienopyrimidinone (IV). A mixture of IV and $POCl_3$ is heated at 55-65° C. for 3 h. Water is then added followed by sodium bicarbonate to neutralize the acid. The mixture is extracted with ethyl acetate and the separated organic layer is concentrated. The residue is purified by column chromatography to afford the chlorine-substituted thienopyrimidine (V). Heating V with an appropriate amine (VI) in n-butanol for 16 h then affords the desired substituted thienopyrimidine (VII).

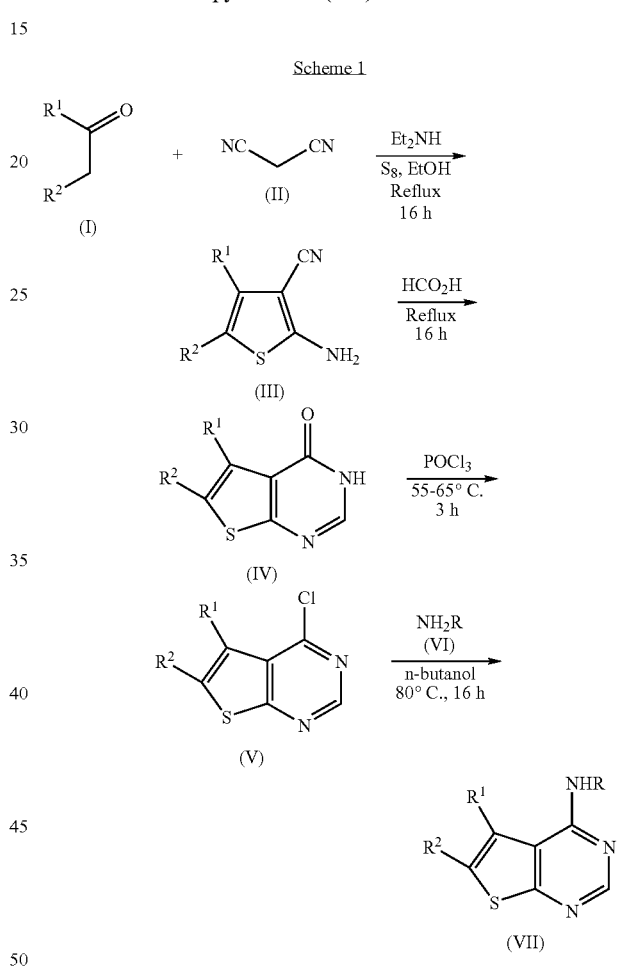

Scheme 1

The thienopyrimdine compounds XVI of this invention can be synthesized by a slightly modified route as shown in Scheme 2. Piperidin-4-one (VIII) is protected with Boc under basic conditions, and the product is reacted with malanonitrile and sulphur to form the thiophene ring. Cyclization of X with formamidine acetate in DMF at 100° C. gives the thienopyrimidinone XI. Reaction of XI with $POCl_3$ provides the chlorine-substituted thienopyrimidine (XII), which is transformed into the substituted thienopyrimidine (XIII) by reacting with an appropriate amine (VI) in hot n-butanol. Removal of the Boc protecting group within XIII with HCl in dioxane for 16 h then affords the compound XIV. Amide coupling of XIV with an appropriate acid XV using HOBt and EDC in DMF, followed by standard work up yields the desired product XVI.

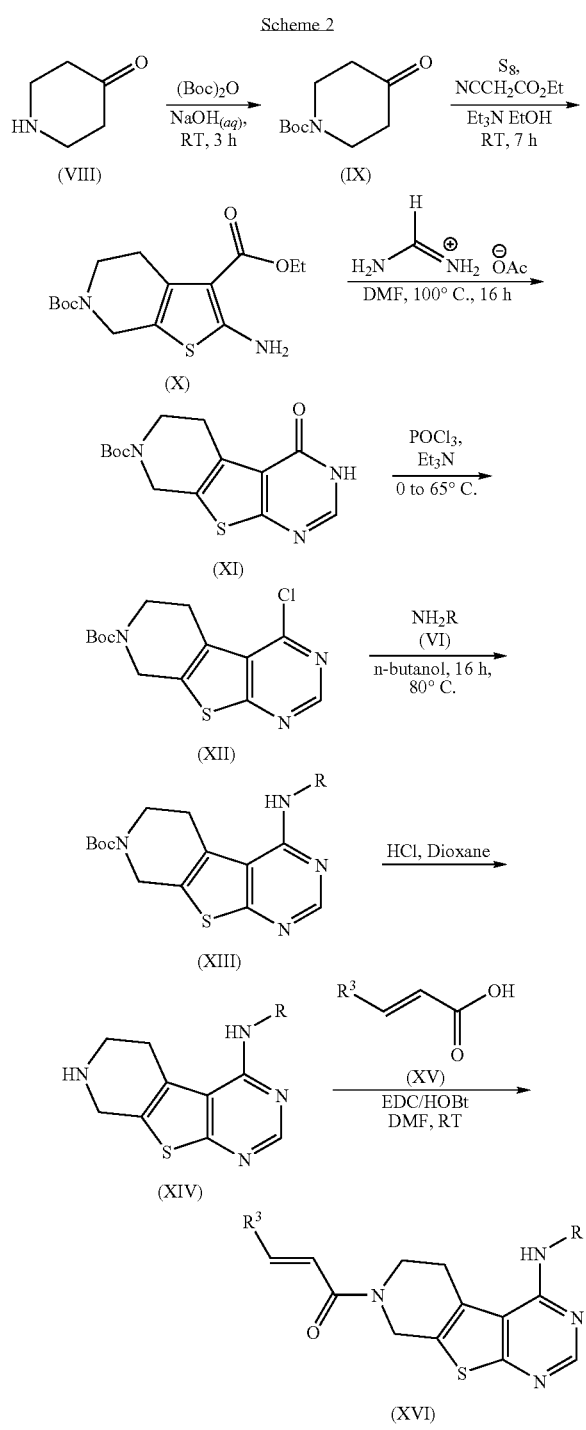

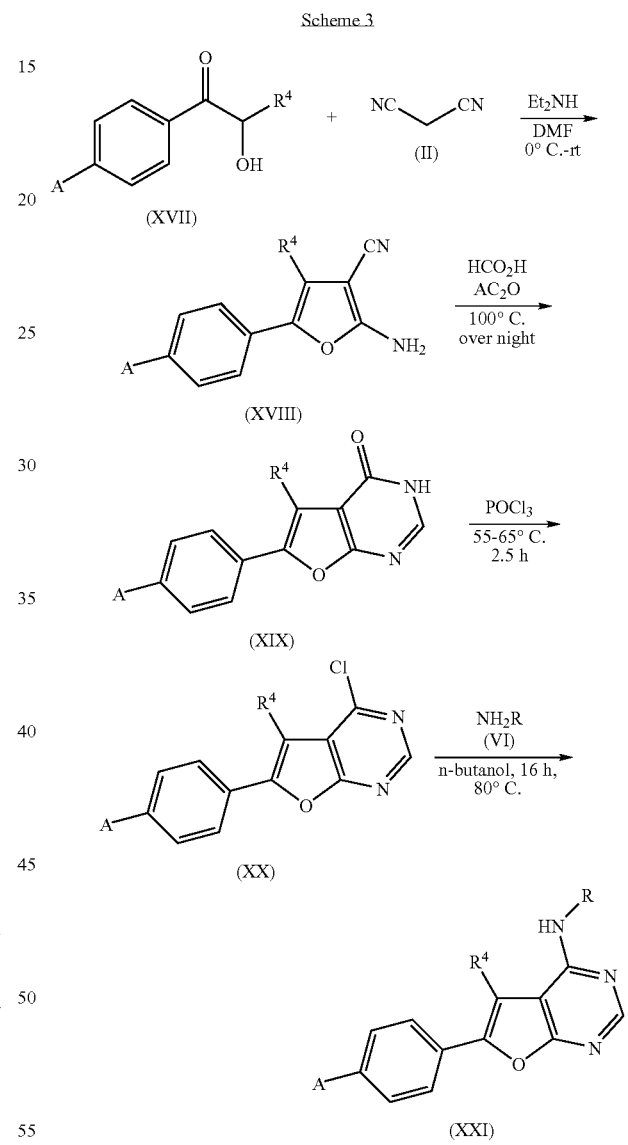

the precipitate formed is collected by filtration to afford the furanopyrimidinone (XIX). A mixture of XIX and POCl$_3$ is heated at 55-65° C. for 3 h. Water is then added, followed by sodium bicarbonate. The resulting mixture is extracted with ethyl acetate. Concentration of the organic layer, followed by purification of the residue by column chromatography, affords the chlorine-substituted furanopyrimidine (XX). Heating XX with an appropriate amine (VI) in hot n-butanol for 16 h affords the desired amino-substituted furanopyrimidine (XXI).

The route shown in Scheme 3 exemplifies the synthesis of furanopyrimidine compounds (XXI) of the present invention. Diethylamine is added dropwise over a period of 30 min to a mixture of an appropriately substituted benzoin (XVII) and malanonitrile (II) in DMF at 0° C. The resulting mixture is allowed to stir for 16 h. Water is then added, and the precipitate thus formed is collected by filtration and crystallized from ethanol to give the substituted furan (XVIII). Acetic anhydride is added dropwise over a period of 30 min to a mixture of XVIII and formic acid at 0° C. The resulting mixture is heated at 100° C. for 16 h. Water is then added and The furanopyrimidine compounds of this invention can also be synthesized by alternative methods. Scheme 4 below exemplifies such an alternative synthetic route. Bromination of a chloro-substituted furanopyrimidine (XX) using N-bromosuccinimide (NBS) in DMF affords the bromo, chloro-substituted furanopyrimidine (XXII). Alternatively, the use of N-chlorosuccinimide (NCS) affords the corresponding dichloro derivative of XXII. Reaction of XXII with an appropriate amine (VI) by heating in n-butanol gives the bromo, amino-substituted furanopyrimidine (XXIII). The furanopyrimidine compound (XXIV) of this invention is then synthesized by reacting compound XXIII with an appropriate boronic acid under the standard Suzuki coupling conditions (Pd(OAc)$_2$, PPh$_3$, and sodium carbonate in a mixture of water and dioxane under refluxing conditions for 2-3 h).

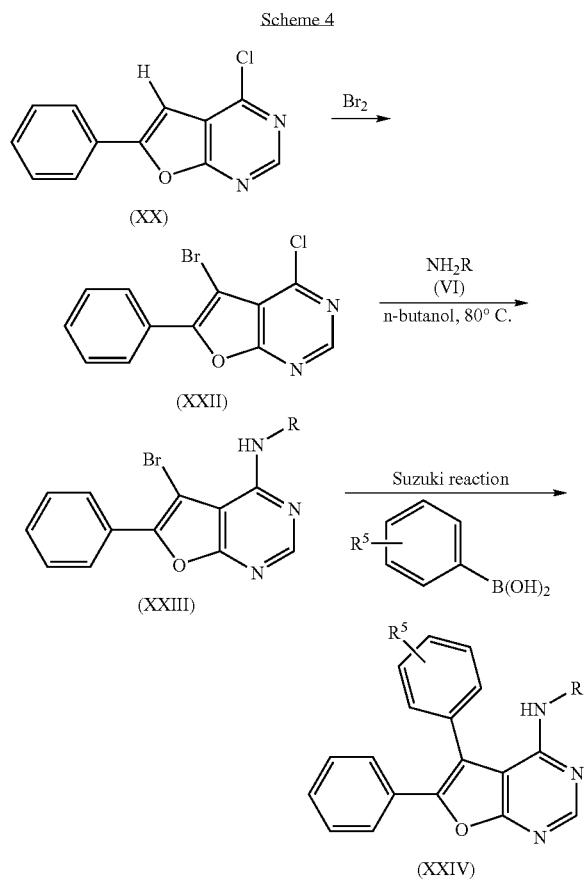

The fused bicyclic or tricyclic compounds of this invention can also be synthesized in manners similar to those outlined in Schemes 1-4 with necessary modifications as recognized by those skilled in the art.

A fused bicyclic or tricyclic compound thus synthesized can be further purified by flash column chromatography, high performance liquid chromatography, crystallization, or any other suitable methods.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of at least one of the fused bicyclic or tricyclic compounds of this invention and a pharmaceutically acceptable carrier, and (2) a method for treating cancer by administering to a subject in need of this treatment an effective amount of such a fused bicyclic or tricyclic compound.

As used herein, the term "treating" refers to administering a fused bicyclic or tricyclic compound to a subject that has cancer, or has a symptom of or a predisposition toward it, with the purpose to cure, heal, alleviate, relieve, alter, remedy, ameliorate, improve, or affect cancer, the symptoms of or the predisposition toward cancer. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

Cancer that can be treated by the methods of the invention include both solid and haematological tumours of various organs. Examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes. Other cancer types, in which EGFR kinase activity is upregulated/dysregulated, are described in *Exp. Mol. Pathol.*, 2008, 84(2):79-89 and *Crit. Rev. Oncol. Hematol.*, 1995, 19, 183.

The compounds of this invention can be administered in conjunction with a therapeutic agent selected from the group consisting of cytotoxic agents, radiotherapy, and immunotherapy. Non-limiting examples of cytotoxic agents suitable for use in combination with the protein kinase inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs, including, e.g., CC-5013 and CC-4047; protein tyrosine kinase inhibitors, including, e.g., imatinib mesylate and gefitinib; antibodies, including, e.g., trastuzumab, rituximab, cetuximab, and bevacizumab; mitoxantrone; dexamethasone; prednisone; and temozolomide.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A fused bicyclic or tricyclic compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, one or more solubilizing agents, which form more soluble complexes with the fused bicyclic or tricyclic compounds, or more solubilizing agents, can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the fused bicyclic or tricyclic compounds of this invention in inhibiting activity of EGFR kinase. The compounds can further be examined for their efficacy in treating cancer in vitro and/or in vivo. For example, a compound can be tested for its efficacy in inhibiting cancer cell growth (e.g., a growth inhibition assay of HCC827 cells) or it can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of S-2-phenyl-2-(5,6,7,8-tetrahydro-benzo[4,5]thieno[2,3-d]pyrimidin-4-ylamino)-ethanol (Compound 1)

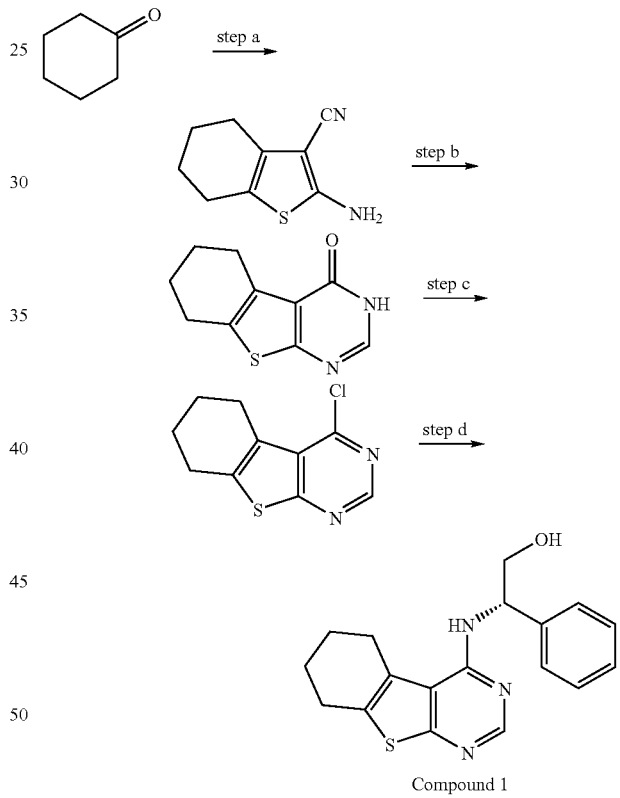

Compound 1

2-Amino-4,5,6,7-tetrahydrobenzo[b]thiophen-3-yl cyanide (step a)

To a mixture of cyclohexanone (1.18 g), malononitrile (0.66 g), and sulphur (0.40 g) in absolute ethanol (3 ml) was added triethylamine (2 mL). After refluxed for 16 h, the reaction mixture was concentrated and the residue was partitioned between water and ethyl acetate. The organic layer was concentrated and the crude compound was purified by silica gel column chromatography using a mixture of hexanes:ethyl acetate (4:1), to give the title compound (0.94 g, 44%).

3,4,5,6,7,8-Hexahydrobenzo[4,5]thieno[2,3-d]pyrimidin-4-one (step b)

To a mixture of 2-amino-4,5,6,7-tetrahydrobenzo[b]thiophen-3-yl cyanide (0.9 g) and formic acid (10 mL) was added 0.1 mL conc. HCl. After refluxed for 16 h, the reaction mixture was cooled and water (20 mL) was added. The precipitate was collected by filtration and washed thoroughly with water and hexanes to give the title compound (0.8 g, 77%). $^1$H NMR (300 MHz, CDCl$_3$): δ 7.91 (s, 1H), 3.03-3.00 (m, 2H), 2.80-2.77 (m, 2H), 1.89-1.83 (m, 4H).

4-Chloro-5,6,7,8-tetrahydrobenzo[4,5]thieno[2,3-d]pyrimidine (step c)

A mixture of 3,4,5,6,7,8-hexahydrobenzo[4,5]thieno[2,3-d]pyrimidin-4-one (0.8 g) and POCl$_3$ (10 mL) was heated at 55-65° C. for 3 h. Water was then added followed by sodium bicarbonate. The resulting mixture was extracted with ethyl acetate. The organic layer was concentrated and the crude compound was purified by silica gel column chromatography using a mixture of hexanes:ethyl acetate (20:1), to give the title compound (0.52 g, 60%). $^1$H NMR (300 MHz, CDCl$_3$): δ 8.69 (s, 1H), 3.10-3.07 (m, 2H), 2.88-2.86 (m, 2H), 1.89-1.92 (m, 4H). LC-MS (ESI) m/z 225.3 (M+H).

S-2-Phenyl-2-(5,6,7,8-tetrahydro-benzo[4,5]thieno[2,3-d]pyrimidin-4-ylamino)-ethanol (Compound 1, step d)

A mixture of 4-chloro-5,6,7,8-tetrahydrobenzo[4,5]thieno[2,3-d]pyrimidine (1 g) and S-2-amino-2-phenyl-ethanol (0.672 g, 1.1 eq) in n-butanol (1 mL) was heated at 80° C. for 16 h. The reaction mixture was concentrated and the residue was partitioned between water and dichloromethane. The organic layer was washed with brine, dried over MgSO$_4$ and concentrated. The crude compound was purified by silica gel column chromatography using a mixture of dichloromethane:methanol (30:1), to give the title compound (0.88 g). $^1$H NMR (400 MHz, CDCl$_3$): δ 8.20 (s, 1H), 7.25-7.36 (m, 5H), 6.14 (d, 1H), 5.36 (dd, 1H, J=9.6, 5.6 Hz), 3.93-4.02 (m, 2H), 2.81-2.99 (m, 2H), 2.74 (s, 2H), 1.80-1.96 (m, 4H). LC-MS (ESI) m/z 326.1 (M+H).

Example 2

Syntheses of Compounds 2-8, 17-24, 29, 30, 245, and 246

Compounds 2-8, 17-24, 29, 30, 245, and 246 were prepared in a manner similar to that described in Example 1. $^1$H NMR and MS data of these compounds are listed below.

Compound 2: $^1$H-NMR (400 MHz, CDCl$_3$): δ 8.20 (s, 1H), 7.25-7.34 (m, 5H), 6.11 (d, 1H, J=6.4 Hz), 5.35-5.38 (m, 1H), 3.93-3.99 (m, 2H), 2.88-2.93 (m, 2H), 2.73-2.76 (m, 2H), 1.82-1.88 (m, 4H). LC-MS (ESI) m/z 326.1 (M+1).

Compound 3: $^1$H-NMR (400 MHz, CDCl$_3$) δ 2.48-2.55 (m, 2H), 2.93-3.06 (m, 4H), 3.83 (brs, 1H), 4.00 (dd, 2H, J=5.2, 5.2 Hz), 5.34 (ddd, 1H, J=5.2, 5.2, 5.2 Hz), 5.80 (d, 1H, J=6.0 Hz), 7.29-7.40 (m, 5H), 8.31 (s, 1H). $^{13}$C-NMR (75 MHz, CDCl$_3$) δ 27.9 (CH$_2$), 28.9 (CH$_2$), 29.4 (CH$_2$), 57.1 (CH), 67.2 (CH$_2$), 113.4 (C), 126.4 (CH), 127.8 (CH), 128.9 (CH), 134.3 (C), 139.1 (C), 139.6 (C), 152.5 (CH), 156.3 (C). HRMS (EI) calcd. for C$_{17}$H$_{17}$N$_3$OS (M$^+$) 311.1092. found 311.1096.

Compound 4: LC-MS (ESI) m/z 300.0 (M+H)$^+$.
Compound 5: LC-MS (ESI) m/z 286.0 (M+H)$^+$.
Compound 6: LC-MS (ESI) m/z 272.0 (M+H)$^+$.
Compound 7: LC-MS (ESI) m/z 348.0 (M+H)$^+$.
Compound 8: LC-MS (ESI) m/z 382.3 (M+H)$^+$.

Compound 17: $^1$H NMR (400 MHz, CDCl$_3$): δ 8.30 (s, 1H), 7.445-7.48 (m, 1H), 7.31-7.37 (m, 4H), 6.41 (d, 1H, J=6.4 Hz), 5.90 (d, 1H, 6.4 Hz), 3.74 (s, 3H), 3.00-3.04 (m, 2H), 2.77-2.80 (m, 2H), 1.18-1.95 (m, 4H). LC-MS (ESI) m/z 354.2 (M+H).

Compound 18: $^1$H NMR (300 MHz, CDCl$_3$): δ 9.00 (s, 1H), 7.22~7.31 (m, 5H), 5.78 (s, 1H), 2.78~3.07 (m, 4H), 1.84~2.01 (m, 4H).

Compound 19: LC-MS (ESI) m/z 340.0 (M+H)$^+$.
Compound 20: LC-MS (ESI) m/z 326.0 (M+H)$^+$.
Compound 21: LC-MS (ESI) m/z 376.0 (M+H)$^+$.
Compound 22: LC-MS (ESI) m/z 362.0 (M+H)$^+$.

Compound 23: $^1$H-NMR (400 MHz, CDCl$_3$) δ 0.94 (t, 3H, J=4.0 Hz), 1.85-2.01 (m, 6H), 2.76-2.78 (m, 2H), 2.91-2.96 (m, 2H), 5.31 (q, 1H, J=4.0 Hz), 5.56 (d, 1H, J=7.6 Hz), 7.21-7.23 (m, 1H), 7.24-7.34 (m, 4H), 8.31 (s, 1H). HRMS (EI) calcd. for C$_{19}$H$_{21}$N$_3$S (M$^+$) 323.1456. found 323.1452.

Compound 24: LC-MS (ESI) m/z 324.0 (M+H)$^+$.

Compound 29: $^1$H-NMR (300 MHz, CDCl$_3$) δ 0.93 (t, 3H, J=7.2 Hz), 1.42 (s, 9H), 1.87-2.00 (m, 2H), 2.98-3.00 (m, 2H), 3.77-3.78 (m, 2H), 4.62 (s, 2H), 5.29 (td, 1H, J=7.2, 7.2 Hz), 5.41 (d, 1H, J=7.2 Hz), 7.22-7.33 (m, 5H), 8.33 (s, 1H). LCMS (ESI) m/z 425.1 [M+H]$^+$.

Compound 30: LC-MS (ESI) m/z 346.0 (M+H)$^+$.

Compound 245: $^1$H NMR (400 MHz, CDCl$_3$): δ: 8.17 (s, 1H), 8.08 (br, 1H), 7.61 (s, 1H), 7.41-7.37 (m, 3H), 7.32-7.20 (m, 6H), 6.42 (dd, J=1.8, 17.0 Hz, 1H), 6.34 (dd, J=9.6, 16.8 Hz, 1H), 5.75 (dd, J=2.0, 9.6 Hz, 1H), 5.43 (dd, J=4.0, 7.2 Hz, 1H), 4.01 (dd, J=4.2, 11.8 Hz, 1H), 3.94 (dd, J=7.4, 11.8 Hz, 1H). LCMS: 417.0 (M+H).

Compound 246: $^1$H NMR (400 MHz, CDCl$_3$): δ: 8.39 (s, 1H), 7.79 (d, J=8.4 Hz, 1H), 7.71 (s, 1H), 7.44 (t, J=8.0 Hz, 1H), 7.32 (s, 1H), 7.26-7.21 (m, 4H), 7.16 (s, 1H), 7.02 (dd, J=2.0, 7.6 Hz, 1H), 6.45 (dd, J=1.4, 17.0 Hz, 1H), 6.32 (dd, J=10.2, 17.0 Hz, 1H), 5.94 (d, J=6.8 Hz, 1H), 5.78 (dd, J=1.6, 10.0 Hz, 1H), 5.32 (br, 1H), 3.81 (d, J=8.0 Hz, 1H), 3.63 (d, J=6.8 Hz, 1H). LCMS: 417.0 (M+H).

Example 3

Synthesis of 1-[4-(2-hydroxy-1-phenyl-ethylamino)-5,8-dihydro-6H-9-thia-1,3,7-triaza-fluoren-7-yl]-propenone (Compound 12)

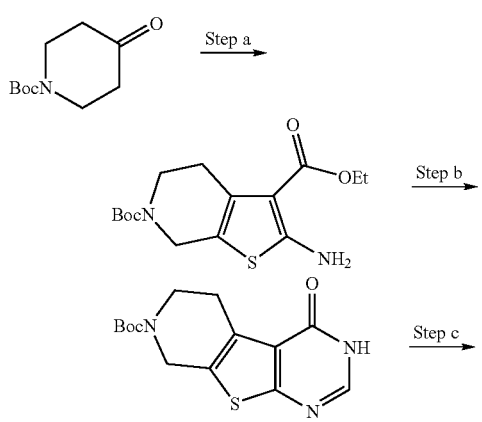

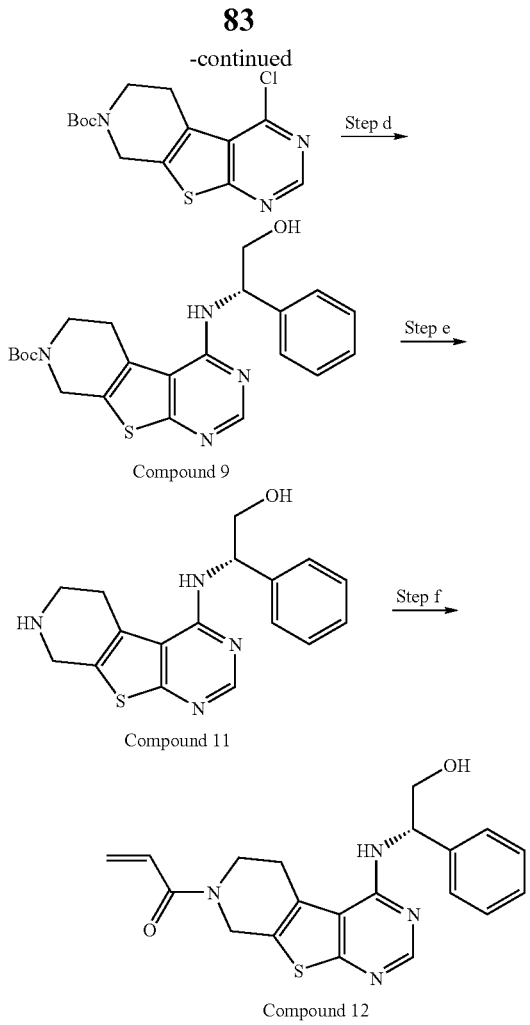

Compound 9

Compound 11

Compound 12

2-Amino-4,7-dihydro-5H-thieno[2,3-c]pyridine-3,6-dicarboxylic acid 6-tert-butyl ester 3-ethyl ester (step a)

To a mixture of 4-oxo-piperidine-1-carboxylic acid tert-butyl ester (12.9 g), ethyl cyanoacetate (7.345 g), and sulphur (2.080 g) in absolute ethanol (50 mL) was added triethylamine (9 mL). After stirring for 16 h, the precipitate was collected by filtration and washed with ethanol to give the title compound (18.7 g, 88%). $^1$H NMR (300 MHz, CDCl$_3$): δ 6.02 (s, 2H), 4.31 (s, 2H), 4.23 (q, 2H, J=7.2 Hz), 3.58 (t, 2H, J=6.0 Hz), 2.72-2.80 (brs, 2H), 1.44 (s, 9H), 1.30 (t, 3H, J=7.2 Hz). LC-MS (ESI) m/z 327.0 (M+H).

4-Oxo-3,5,6,8-tetrahydro-4H-9-thia-1,3,7-triaza-fluorene-7-carboxylic acid tert-butyl ester (step b)

A mixture of 2-amino-4,7-dihydro-5H-thieno[2,3-c]pyridine-3,6-dicarboxylic acid 6-tert-butyl ester 3-ethyl ester (18.5 g) and formamidine acetate (8.85 g) in DMF (100 mL) were heated at 100° C. for 16 h. The reaction mixture was cooled and concentrated. The residues was partitioned between water and ethyl acetate. The organic layer was washed with water 3 times and concentrated to give the title compound (15.8 g, 90%). $^1$H NMR (400 MHz, CDCl$_3$): δ 7.88 (s, 1H), 4.56-4.62 (brs, 2H), 3.62-3.70 (brs, 2H), 3.02-3.08 (brs, 2H), 1.42 (s, 9H). LC-MS (ESI) m/z 308.1 (M+H).

4-Chloro-5,8-dihydro-6H-9-thia-1,3,7-triaza-fluorene-7-carboxylic acid tert-butyl ester (step c)

To a of mixture of POCl$_3$ (30 mL) and triethylamine (50 mL) at 0° C. was added 4-oxo-3,5,6,8-tetrahydro-4H-9-thia-1,3,7-triaza-fluorene-7-carboxylic acid tert-butyl ester (10.0 g). The reaction mixture was heated at 60° C. for 3 h. Water was then added, followed by sodium bicarbonate to neutralize the reaction mixture. The resulting mixture was extracted with dichloromethane. The organic layer was concentrated and the crude compound was purified by silica gel column chromatography using a mixture of hexanes:ethyl acetate (10:1) to give the title compound (3.1 g, 25%). $^1$H NMR (400 MHz, CDCl$_3$): δ 8.70 (s, 1H), 4.69 (s, 2H), 3.74 (t, 2H, J=5.6 Hz), 3.14-3.18 (brs, 2H), 1.46 (s, 9H). LC-MS (ESI) m/z 326.0 (M+H).

4-(2-Hydroxy-1-phenyl-ethylamino)-5,8-dihydro-6H-9-thia-1,3,7-triaza-fluorene-7-carboxylic acid tert-butyl ester (Compound 9, step d)

A mixture of 4-chloro-5,8-dihydro-6H-9-thia-1,3,7-triaza-fluorene-7-carboxylic acid tert-butyl ester (0.25 g) and S-2-amino-2-phenyl-ethanol (0.128 g) in n-butanol (1 mL) was refluxed for 8 h. The reaction mixture was concentrated and the residue was partitioned between water and dichloromethane. The organic layer was concentrated and the crude compound was purified by silica gel column chromatography using a mixture of dichloromethane:methanol (20:1) to give the title compound (0.309 g, 95%). $^1$H NMR (300 MHz, CDCl$_3$): δ 8.25 (s, 1H), 7.26-7.38 (m, 5H), 6.04 (d, 1H, J=6.6 Hz), 5.36-5.43 (m, 1H), 4.62 (s, 2H), 3.97-4.02 (m, 2H), 3.72-3.81 (m, 2H), 2.90-3.08 (m, 2H), 1.46 (s, 9H). LC-MS (ESI) m/z 427.0 (M+H).

2-Phenyl-2-(5,6,7,8-tetrahydro-9-thia-1,3,7-triaza-fluoren-4-ylamino)-ethanol (Compound 11, step e)

To a mixture of 4-(2-hydroxy-1-phenyl-ethylamino)-5,8-dihydro-6H-9-thia-1,3,7-triaza-fluorene-7-carboxylic acid tert-butyl ester (0.6 g) in dichloromethane (2 mL) at room temperature was added TFA (1 mL). The reaction mixture was stirred for 4 h, then neutralized by slow addition of sodium bicarbonate solution. The precipitate formed was collected by filtration and washed with water then dichloromethane to give the title compound (0.350 g, 76%). $^1$H NMR (400 MHz, CDCl$_3$): δ 8.28 (s, 1H), 7.26-7.38 (m, 5H), 6.04 (d, 1H, J=6.4 Hz), 5.38 (d, 1H, J=4.8 Hz), 4.01 (d, 2H, J=7.6 Hz), 3.99 (d, 2H, J=3.2 Hz), 3.20 (t, 2H, J=4.4 Hz), 2.84-3.04 (m, 2H). LC-MS (ESI) m/z 327.1 (M+H).

1-[4-(2-Hydroxy-1-phenyl-ethylamino)-5,8-dihydro-6H-9-thia-1,3,7-triaza-fluoren-7-yl]-propenone (Compound 12, step f)

A mixture of acrylic acid (3.6 mg) and EDCI (9.4 mg) in anhydrous DMF was stirred for 2 h and 2-phenyl-2-(5,6,7,8-tetrahydro-9-thia-1,3,7-triaza-fluoren-4-ylamino)-ethanol was then added. The resulting mixture was stirred for 16 h, then partitioned between water and ethyl acetate. The organic layer was dried over MgSO$_4$, concentrated. The residue was purified by silica gel column chromatography using a mixture of dichloromethane:methanol (5:1) to give the title compound (8 mg, 44%). $^1$H NMR (300 MHz, CD$_3$OD): δ 8.18 (s, 1H), 7.20-7.44 (m, 5H), 6.78-6.98 (m, 1H), 6.28 (d, 1H, J=17.1 Hz), 5.78-5.84 (m, 1H), 5.39 (t, 1H, J=5.1 Hz), 4.80-

4.98 (m, 2H), 4.07 (t, 2H, J=5.7 Hz), 3.82-3.98 (m, 2H), 3.20-3.38 (m, 2H). LC-MS (ESI) m/z 381.0 (M+H).

Example 4

Syntheses of Compounds 9-11, 13-16, 25-28, and 59-68, 75, 106, 107, 154, 176, 178, 180, 181, 183-235, and 327

Syntheses of Compounds 9 and 11 were described in Example 3. Compounds 10, 13-16, 25-28, and 59-68, 75, 106, 107, 154, 176, 178, 180, 181, 183-235, and 327 were prepared in a manner similar to that described in Example 3. $^1$H NMR and MS data of these compounds are listed below.

Compound 10: $^1$H NMR (400 MHz, CDCl$_3$): δ 8.31 (s, 1H), 7.29~7.39 (m, 5H), 6.00 (d, 1H, J=6.4 Hz), 5.38~5.40 (m, 1H), 4.70 (s, 2H), 4.17 (q, 2H, J=7.2 Hz), 4.00 (d, 2H, J=4.0 Hz), 3.79~3.84 (m, 2H), 3.00~3.05 (m, 2H), 1.27 (t, 3H, J=7.2 Hz).

Compound 13: $^1$H-NMR (400 MHz, CD$_3$OD) δ 8.15 (s, 1H), 7.38-7.42 (m, 2H), 7.24-7.33 (m, 2H), 7.20-7.23 (m, 1H), 5.38-5.40 (m, 1H), 4.77-4.79 (m, 2H), 3.87-3.98 (m, 4H), 3.14-3.26 (m, 2H), 2.55 (q, 1.2H, J=7.6 Hz), 2.48 (q, 0.8H, J=7.6 Hz), 1.17 (t, 1.8H, J=7.6 Hz), 1.12 (t, 1.2H, J=7.6 Hz); HRMS (EI) calcd. for C$_{20}$H$_{21}$N$_4$O$_2$S (M$^+$) 382.1463. found 382.1466.

Compound 14: $^1$H-NMR (300 MHz, CDCl$_3$): δ 8.23 (s, 1H), 7.67 (d, 1H, J=15.6 Hz), 7.47-7.52 (m, 2H), 7.24-7.27 (m, 8H), 6.91 (d, 1H, J=15.6 Hz), 6.16 (s, 1H), 5.41 (s, 1H), 4.75-4.92 (m, 2H), 3.92-4.04 (m, 4H), 3.08 (br, 2H). LC-MS (ESI) m/z 457.1 (M+H).

Compound 15: $^1$H NMR (300 MHz, CDCl$_3$): δ −0.16 (s, 3H), −0.06 (s, 3H), 0.83 (s, 9H), 3.16 (m, 2H), 3.87~4.07 (m, 4H), 4.80~4.89 (m, 2H), 5.37~5.42 (m, 1H), 5.77 (d, 1H, J=12 Hz), 6.34 (d, 1H, J=18 Hz), 6.56~6.60 (m, 1H), 7.20~7.34 (m, 5H), 8.29 (s, 1H). LC-MS (ESI) m/z 495.2 (M+H).

Compound 16: $^1$H-NMR (300 MHz, CDCl$_3$): δ 1.97~2.03 (m, 3H), 2.96~3.24 (m, 2H), 3.84~4.15 (m, 4H), 4.67~4.82 (m, 1H), 4.92 (s, 1H), 5.35~5.45 (m, 1H), 6.13~6.16 (m, 1H), 7.23~7.36 (m, 5H), 8.22 (s, 0.5H), 8.24 (s, 0.5H); $^{13}$C-NMR (75 MHz, CDCl$_3$) δ 4.1 (CH$_3$), 25.7 (CH$_2$), 26.7 (CH$_2$), 29.6 (C), 38.4 (CH$_2$), 41.0 (CH$_2$), 43.7 (CH$_2$), 46.2 (CH$_2$), 56.5 (CH), 56.7 (CH), 66.4 (CH$_2$), 66.5 (CH$_2$), 72.4 (C), 72.5 (C), 90.1 (C), 91.3 (C), 115.3 (C), 115.4 (C), 124.0 (C), 124.9 (C), 126.4 (CH), 126.5 (C), 127.7 (C), 127.8 (CH), 128.6 (CH), 128.8 (C), 128.8 (C), 129.0 (C), 139.3 (C), 139.4 (C), 152.8 (C), 153.2 (CH), 153.3 (CH), 156.7 (C), 156.9 (C), 164.9 (C), 165.1 (C); HRMS (EI) calcd. for C$_{21}$H$_{20}$N$_4$O$_2$S (M$^+$) 392.1307. found 392.1311.

Compound 25: $^1$H-NMR (300 MHz, CDCl$_3$) δ 0.93 (t, 3H, J=7.2 Hz), 1.42 (s, 9H), 1.87-2.00 (m, 2H), 2.98-3.00 (m, 2H), 3.77-3.78 (m, 2H), 4.62 (s, 2H), 5.29 (td, 1H, J=7.2, 7.2 Hz), 5.41 (d, 1H, J=7.2 Hz), 7.22-7.33 (m, 5H), 8.33 (s, 1H). LCMS (ESI) m/z 425.1 [M+H]$^+$.

Compound 26: LC-MS (ESI) m/z 397.0 (M+H)$^+$.

Compound 27: $^1$H-NMR (400 MHz, CDCl$_3$) δ 0.93 (t, 3H, J=7.6 Hz), 1.89-19.7 (m, 2H), 2.90-3.00 (m, 2H), 3.24 (t, 2H, 5.6 Hz), 4.04 (s, 2H), 5.30 (td, 1H, 7.2, 7.2 Hz), 5.46 (d, 1H, 7.2 Hz), 7.22-7.33 (m, 5H), 8.32 (s, 1H). LCMS (ESI) m/z 325.0 [M+H]$^+$.

Compound 28: LC-MS (ESI) m/z 438.0 (M+H)$^+$.

Compound 59: $^1$H-NMR (400 MHz, CD$_3$OD): δ 7.39~7.41 (m, 2H), 7.29~7.33 (m, 2H), 7.20~7.24 (m, 1H), 6.25~6.30 (m, 1H), 5.79~5.84 (m, 1H), 5.39 (dd, 1H, J=5.2, 5.2 Hz), 4.90 (m, 2H), 3.94-4.04 (m, 2H), 3.89 (dd, 2H, J=6.0, 11.2 Hz), 3.25~3.27 (m, 2H). LC-MS (ESI) m/z 381.1 (M+H).

Compound 60: $^1$H-NMR (400 MHz, CDCl$_3$): δ −0.14 (s, 3H), −0.04 (s, 3H), 0.85 (s, 9H), 3.18~3.29 (m, 2H), 3.88~4.12 (m, 4H), 4.82~4.91 (m, 2H), 5.39~5.40 (m, 1H), 5.79 (d, 1H, J=12 Hz), 6.36 (d, 1H, J=18 Hz), 6.58~6.61 (m, 1H), 7.23-7.37 (m, 5H), 8.31 (s, 1H). LC-MS (ESI) m/z 495.3 (M+H).

Compound 61: $^1$H-NMR (400 MHz, CD$_3$OD): δ 8.12 (s, 1H), 7.32~7.43 (m, 3H), 7.28~7.30 (m, 2H), 7.19~7.23 (m, 1H), 6.16~6.32 (m, 2H), 5.38 (dd, 1H, J=5.6, 5.6 Hz), 4.76~4.83 (m, 2H), 3.86~4.02 (m, 4H), 3.21~3.33 (m, 2H). LC-MS (ESI) m/z 425.2 (M+H).

Compound 62: $^1$H NMR (400 MHz, CDCl$_3$): δ 8.30 (s, 1H), 7.28-7.40 (m, 5H), 6.80-6.98 (brs, 1H), 6.38-6.57 (m, 1H), 6.03 (d, 1H, J=13.6 Hz), 5.39 (s, 1H), 4.86 (s, 1H), 4.78 (s, 1H), 4.00-4.12 (brs, 2H), 3.90-3.99 (brs, 2H), 3.01-3.20 (brs, 4H), 2.24 (s, 6H). LC-MS (ESI) m/z 438.2 (M+H).

Compound 63: $^1$H NMR (400 MHz, CDCl$_3$): δ 8.32 (s, 1H), 7.28-7.39 (m, 5H), 6.44 (dd, 1H, J=16.4, 9.6 Hz), 6.32 (d, 1H, J=16.4 Hz), 6.02 (d, 1H, J=4.8 Hz), 5.99 (d, 1H, J=6.4 Hz), 5.41 (dd, 1H, J=10.4, 4.8 Hz), 4.47 (s, 2H), 3.96-4.23 (m, 2H), 3.63 (t, 2H, J=4.8 Hz), 3.04-3.18 (m, 2H). LC-MS (ESI) m/z 417.1 (M+H).

Compound 64: $^1$H NMR (300 MHz, CD$_3$OD): δ 8.20 (s, 1H), 7.43 (d, 2H, J=7.8 Hz), 7.31 (m, 2H), 7.21 (t, 1H, 6.9 Hz), 6.75-6.93 (m, 1H), 6.26 (d, 1H, J=16.5 Hz), 5.81 (d, 1H, J=10.8 Hz), 5.48 (q, 1H, J=6.9 Hz), 4.78-5.01 (m, 2H), 3.91-4.05 (m, 2H), 3.01-3.22 (m, 2H), 1.61 (d, 3H, J=7.2 Hz). LC-MS (ESI) m/z 365.1 (M+H).

Compound 65: $^1$H-NMR (400 MHz, CDCl$_3$): δ 8.25 (s, 0.5H), 8.24 (s, 0.5H), 7.23-7.33 (m, 5H), 6.81 (m, 1H), 6.35-6.46 (m, 1H), 6.05-6.12 (m, 2H), 5.37-5.38 (m, 1H), 4.81 (m, 1H), 4.74 (m, 1H), 3.88-3.98 (m, 4H), 3.07 (m, 4H), 2.35 (m, 4H), 1.54 (m, 4H), 1.39 (m, 2H). LC-MS (ESI) m/z 478.1 (M+H).

Compound 66: $^1$H-NMR (400 MHz, CDCl$_3$): δ 8.23 (s, 1H), 7.22-7.33 (m, 5H), 6.84-6.88 (m, 1H), 6.53 (t, 1H, J=16.2 Hz), 6.04-6.09 (m, 1H), 5.36-5.38 (m, 1H), 4.81 (m, 1H), 4.74 (m, 1H), 4.79 (m, 1H), 3.88-3.97 (m, 4H), 3.60-3.67 (m, 4H), 3.10-3.11 (m, 4H), 2.42 (m, 4H). LC-MS (ESI) m/z 480.2 (M+H).

Compound 67: $^1$H-NMR (400 MHz, CDCl$_3$): δ 8.28 (s, 1H), 7.25-7.37 (m, 5H), 6.82-6.88 (m, 1H), 6.40-6.50 (m, 1H), 6.09 (d, 1H, J=1.6 Hz), 5.35-5.40 (m, 1H), 4.76-4.88 (m, 2H), 3.89-4.03 (m, 4H), 3.13-3.16 (m, 4H), 2.60 (m, 8H), 2.28 (s, 3H). LC-MS (ESI) m/z 493.1 (M+H).

Compound 68: $^1$H-NMR (300 MHz, CDCl$_3$): δ 8.33 (s, 1H), 7.29-7.47 (m, 6H), 6.81 (dd, 1H, J=15.0, 15.0 Hz), 5.99 dd, 1H, J=6.0, 15.0 Hz), 5.39-5.42 (m, 1H), 4.90 (brs, 1H), 4.81 (brs, 1H), 4.26 (q, 1H, J=7.2 Hz), 4.25 (q, 1H, J=7.2 Hz), 3.92-4.08 (m, 4H), 3.05-3.16 (m, 2H), 1.31 (t, 1.5H, J=7.2 Hz), 1.30 (t, 1.5H, J=7.2 Hz), LC-MS (ESI) m/z 453.1 [M+1]$^+$.

Compound 75: $^1$H-NMR (300 MHz, CDCl$_3$) δ 0.96-1.06 (m, 6H), 2.55-2.58 (m, 4H), 3.11-3.28 (m, 4H), 3.93-4.02 (m, 2H), 4.08-4.13 (m, 2H), 4.80-4.85 (m, 1H), 4.85-4.92 (m, 1H), 5.39-5.44 (m, 1H), 6.08 (s, 1H), 6.52 (dd, 1H, J=14.7, 15.6 Hz), 6.90-6.97 (m, 1H), 7.27-7.41 (m, 5H), 8.32 (s, 1H). HRMS (EI) calcd. for C$_{25}$H$_{31}$N$_5$O$_2$S (M$^+$) 465.2198. found 465.2195.

Compound 106: $^1$H-NMR (400 MHz, CDCl$_3$): δ 0.86-0.91 (t, 3H), 1.77-2.01 (m, 2H), 2.97-3.11 (m, 2H), 3.90-4.08 (m, 2H), 4.79-4.89 (m, 2H), 5.26-5.43 (m, H), 5.74-5.79 (m, H), 6.24-6.36 (m, H), 7.21-7.32 (m, 5H), 8.33 (s, H). LCMS-ESI (m/z): [M+1]$^+$ 479.1.

Compound 107: $^1$H-NMR (400 MHz, CDCl$_3$): δ 0.95 (t, 3H, J=7.2 Hz), 1.85~2.04 (m, 2H), 2.17 (s, 3H), 2.37 (s, 3H), 3.13~3.17 (m, 2H), 3.84~4.03 (m, 2H), 4.80~4.89 (m, 2H), 5.30~5.46 (m, 2H), 6.53 (dd, 1H, J=4.8, 14.4 Hz), 7.25~7.36 (m, 5H), 8.37 (s, 1H). LCMS LCMS-ESI (m/z): 436.1 (M+H).

Compound 154: $^1$H NMR (300 MHz, CDCl$_3$): δ: 8.45 (s, 1H), 8.34 (s, 1H), 7.86 (d, J=7.8 Hz, 1H), 7.74 (br, 2H), 7.49-7.32 (m, 6H), 6.75 (br, 1H), 6.53 (d, J=16.8 Hz, 1H), 6.35 (dd, J=1.5, 26.1 Hz, 1H), 5.85 (d, J=10.2 Hz, 1H), 4.11 (m, 3H). LCMS: 402.1 (M+H).

Compound 176: $^1$H-NMR (400 MHz, CDCl$_3$): δ 1.97-2.02 (m, H), 2.23-2.31 (m, H), 2.96-3.03 (m, H), 3.10-3.16 (m, H), 3.68-3.91 (m, 4H), 4.79-4.95 (m, 2H), 5.58-5.63 (m, H), 5.75-5.78 (m, H), 6.30-6.42 (m, H), 6.55-6.66 (m, H), 7.27-7.33 (m, 5H), 8.33 (s, H). LC-MS (ESI) m/z 395.1 (M+H).

Compound 178: $^1$H-NMR (400 MHz, CDCl$_3$): δ 1.23-1.27 (m, 3H), 2.17-2.27 (m, 6H), 3.03-3.11 (m, 4H), 3.93-4.05 (m, 2H), 4.80-4.93 (m, 2H), 5.32-5.40 (m, H), 5.52-5.53 (m, H), 6.43-6.54 (m, H), 7.27-7.38 (m, 5H), 8.39 (s, H). LC-MS (ESI) m/z 422.5 (M+H).

Compound 180: $^1$H-NMR (400 MHz, CDCl$_3$): δ 8.22 (1H, s), 7.36-7.24 (5H, m), 6.11 (1H, s), 5.41-5.37 (1H, m), 5.27 (1H, s), 5.10 (1H, s), 3.99-3.89 (4H, m), 3.14-3.02 (2H, m), 2.00-1.91 (5H, m).

Compound 181: $^1$H-NMR (400 MHz, CDCl$_3$): δ 0.83 (s, 15H), 2.17-2.18 (m, 6H), 3.06-3.09 (m, 4H), 3.89-4.11 (m, 4H), 4.86 (m, 2H), 5.41-5.43 (m, H), 5.43-5.44 (m, H), 6.37-6.41 (m, H), 7.23-7.36 (m, 5H), 8.30 (s, H).

Compound 183: $^1$H-NMR (400 MHz, CDCl$_3$): δ 1.25 (m, 3H), 2.05-2.27 (m, 4H), 3.03-3.11 (m, 4H), 3.93-4.05 (m, 2H), 4.80-4.94 (m, 2H), 5.29-5.54 (m, H), 6.43-6.52 (m, H), 7.27-7.38 (m, 5H), 8.37 (s, H). LC-MS (ESI) m/z 422.1 (M+H).

Compound 184: $^1$H-NMR (400 MHz, CDCl$_3$): δ 1.05-1.16 (m, 6H), 1.24-1.27 (m, 3H), 2.56-2.57 (m, 4H), 3.07 (m, 2H), 3.93-3.99 (m, 2H), 4.80-4.93 (m, 2H), 5.33-5.53 (m, 2H), 6.46-6.59 (m, H), 7.28-7.38 (m, 5H), 8.39 (s, H).

Compound 185: $^1$H-NMR (300 MHz, CDCl$_3$): δ 8.31 (s, 1H), 7.22~7.38 (m, 5H), 6.54~6.66 (m, 1H), 6.30~6.39 (m, 1H), 5.99~6.11 (m, 1H), 5.75~5.79 (m, 1H), 5.52 (m, 1H), 4.80~4.88 (m, 2H), 3.76~4.13 (m, 4H), 3.38 (s, 3H), 3.03~3.04 (m, 2H). LC-MS (ESI) m/z 395.1 (M+H).

Compound 186: $^1$H-NMR (400 MHz, CDCl$_3$): δ 8.29 (s, 0.5H), 8.28 (s, 0.5H), 7.23-7.31 (m, 5H), 6.88-6.92 (m, 1H), 6.51-6.59 (m, 1H), 6.29-6.36 (m, 1H), 5.38-5.40 (m, 1H), 4.81-4.88 (m, 2H), 3.86-4.05 (m, 4H), 3.17 (m, 4H), 2.32 (s, 6H), 0.83 (s, 9H), −0.11 (s, 3H), −0.20 (s, 3H); LC-MS (ESI) m/z 552.2 (M+H).

Compound 187: $^1$H NMR (300 MHz, CDCl$_3$): d 8.52 (s, 1H), 7.82 (br, 1H), 7.42 (br, 1H), 7.17 (m, 1H), 6.92 (m, 2H), 6.52 (m, 1H), 4.90 (br d, 2H), 4.03 (br, 2H), 3.17 (br, 4H), 2.29 (s, 6H). LC-MS (ESI) m/z 446.0 (M+H)$^+$.

Compound 188: $^1$H-NMR (400 MHz, CDCl$_3$): δ 1.97-2.05 (m, H), 2.24-2.30 (m, H), 2.97-3.01 (m, H), 3.09-3.15 (m, H), 3.65-3.99 (m, 4H), 4.85-4.91 (m, 2H), 5.58-5.62 (m, H), 5.76-5.79 (m, H), 6.30-6.38 (m, H) 7.26-7.39 (m, 5H), 8.34 (s, H). LC-MS (ESI) m/z 395.1 (M+H).

Compound 189: $^1$H-NMR (400 MHz, CDCl$_3$): δ 1.12-1.15 (m, 3H), 1.61-1.64 (m, 3H), 2.41-2.49 (m, 2H), 2.94-3.08 (m, 2H), 3.78-3.86 (m, H), 3.92-4.01 (m, H), 4.77-4.89 (m, 2H), 5.50-5.55 (m, H), 7.27-7.41 (m, 5H), 8.39 (s, H).

Compound 190: $^1$H-NMR (400 MHz, CDCl$_3$): δ 1.13-1.20 (m, 6H), 1.62-1.64 (m, 3H), 2.54-2.68 (m, 4H), 3.04-3.08 (m, 2H), 3.28-3.29 (m, 2H), 3.44-3.99 (m, 2H), 4.80-4.89 (m, 2H), 5.33-5.39 (m, H), 5.53 (m, H), 6.44-6.58 (m, H), 7.27-7.38 (m, 5H), 8.40 (s, H).

Compound 191: $^1$H-NMR (400 MHz, CDCl$_3$): δ 0.93-0.97 (t, 3H), 1.13-1.16 (m, 6H), 1.92-2.01 (m, 2H), 2.16-2.56 (m, 4H), 3.10-3.28 (m, 2H), 3.46-3.47 (m, 2H), 3.95-4.01 (m, 2H), 4.79-4.92 (m, 2H), 5.29-5.44 (m, 2H), 6.46-6.60 (m, H), 7.25-7.30 (m, 5H), 8.36 (s, H).

Compound 192: $^1$H-NMR (400 MHz, CDCl$_3$): δ 2.05-2.17 (m, 6H), 2.27-2.33 (m, H), 2.49-2.77 (m, H), 2.92-2.95 (m, H), 3.07-3.15 (m, 4H), 3.74-3.88 (m, 4H), 4.81-4.51 (m, H), 4.76-4.85 (m, 2H), 5.36-5.39 (m, H), 6.42-6.52 (m, H), 7.26-7.36 (m, 4H), 8.36 (s, H). LCMS-ESI (m/z): 452.1 (M+H).

Compound 193: $^1$H-NMR (400 MHz, CDCl$_3$): δ 2.47-2.49 (m, H), 2.76-2.78 (m, H), 2.91-2.96 (m, H), 3.08-3.13 (m, H), 3.74-3.88 (m, 4H), 4.48-4.49 (m, H), 4.76-4.85 (m, 2H), 5.76-5.82 (m, H), 6.31-6.38 (m, H), 6.54-6.64 (m, H), 7.25-7.36 (m, 5H), 8.38 (s, H).

Compound 194: $^1$H-NMR (400 MHz, CDCl$_3$): δ 1.96-2.02 (m, 6H), 3.03-3.16 (m, 4H), 3.75-3.96 (m, 4H), 4.74-4.95 (m, 2H), 6.43-6.53 (m, H), 6.68-6.89 (m, 2H), 7.25-7.35 (m, 5H), 8.30 (s, H). LCMS-ESI (m/z): 452.1 (M+H).

Compound 195: $^1$H-NMR (400 MHz, CDCl$_3$): δ 8.30 (s, 1H), 7.22~7.31 (m, 10H), 6.57 (dd, 1H, J=10.8, 17.8 Hz), 6.35 (dd, 1H, J=8.0, 17.6 Hz), 6.15 (m, 1H), 5.77~5.79 (m, 1H), 5.51~5.52 (m, 1H), 4.78~4.88 (m, 2H), 4.52 (s, 2H), 3.77~3.95 (m, 4H), 2.94~3.00 (m, 2H). LC-MS (ESI) m/z 471.2 (M+H).

Compound 196: $^1$H-NMR (400 MHz, CDCl$_3$): δ 8.29 (s, 1H), 7.22~7.37 (m, 10H), 6.14 (d, 1H, J=6.8 Hz), 5.52 (m, 1H), 4.63 (s, 2H), 4.52 (s, 2H), 3.71~3.89 (m, 4H), 2.93~2.94 (m, 2H), 1.49 (s, 9H). LC-MS (ESI) m/z 517.2 (M+H).

Compound 197: $^1$H-NMR (300 MHz, CDCl$_3$): δ 8.28 (s, 1H), 7.21~7.39 (m, 10H), 6.22 (d, 1H, J=6.6 Hz), 5.52~5.55 (m, 1H), 4.52 (s, 2H), 4.04 (d, 2H, J=2.1 Hz), 3.91 (dd, 1H, J=4.2, 9.6 Hz), 3.82 (dd, 1H, J=4.8, 9.6 Hz), 3.16 (dd, 2H, J=6.0, 6.0 Hz), 2.88~2.90 (m, 2H). LC-MS (ESI) m/z 417.1 (M+H).

Compound 198: $^1$H-NMR (300 MHz, CDCl$_3$): δ 8.29 (s, 1H), 7.22~7.35 (m, 10H), 6.88 (m, 1H), 6.43~6.49 (m, 1H), 6.13 (m, 1H), 5.52 (m, 1H), 4.79~4.85 (m, 2H), 4.53 (s, 2H), 3.87~3.91 (m, 2H), 3.79 (m, 2H), 3.10~3.11 (m, 2H), 2.99 (m, 2H), 2.27 (m, 6H). LC-MS (ESI) m/z 528.2 (M+H).

Compound 199: $^1$H-NMR (400 MHz, CDCl$_3$): δ 0.87-0.94 (m, 6H), 2.27-2.40 (m, 2H), 2.56-2.57 (m, 4H), 2.99-3.26 (m, 4H), 3.64-4.16 (m, 4H), 4.65 (m, 2H), 5.53-5.59 (m, 2H), 6.93-6.98 (m, H), 7.25-7.36 (m, 5H), 8.36 (s, H).

Compound 200: $^1$H NMR (300 MHz, CDCl$_3$): δ 8.32 (s, 1H), 7.39-6.98 (m, 7H), 6.99 (m, 2H), 6.63 (dd, 1H, J$_1$=9.3 Hz, J$_2$=16.2 Hz), 6.37 (d, 1H, J=6.9 Hz), 6.12 (d, NH), 5.79 (d, 1H, J=9.6 Hz), 5.57 (br s, 1H), 4.84 (br, 2H), 4.53 (s, 2H), 3.89 (m, 2H), 3.06 (br, 2H). LC-MS (ESI) m/z 489.1 (M+H).

Compound 201: $^1$H-NMR (400 MHz, CDCl$_3$): δ 8.57 (s, 1H), 7.30 (m, 7H), 6.88 (m, 6H), 5.18 (m, 1H), 4.59 (m, 4H), 4.42 (br, 2H), 3.71 (br, 1H), 3.54 (br, 1H), 3.13 (br, 1H), 3.00 (br, 1H). LC-MS (ESI) m/z 643.2 (M+H).

Compound 202: $^1$H NMR (300 MHz, CDCl$_3$): δ 8.34 (s, 1H), 7.58 (d, 2H, J=8.4 Hz), 7.37-7.25 (m, 7H), 6.99 (m, 2H), 6.59 (dd, 1H, J$_1$=10.5 Hz, J$_2$=16.5 Hz), 6.36 (d, 1H, J=16.5 Hz), 6.09 (s, NH), 5.79 (dd, 1H, J$_1$=1.8 Hz, J$_2$=11.1 Hz), 5.60 (br s, 1H), 4.85 (m, 2H), 4.60 (m, 2H), 3.79 (m, 4H), 3.05 (br, 2H). LC-MS (ESI) m/z 539.2 (M+H).

Compound 203: $^1$H NMR (400 MHz, CDCl$_3$): δ 8.52 (d, 1H, J=14.4 Hz), 8.31 (s, 1H), 7.63 (m, 1H), 7.19-7.39 (m, 2H), 6.92 (br, 1H), 6.48 (br, 1H), 6.24 (br, 1H), 5.58 (s, 1H), 4.88 (m, 2H), 4.67 (s, 1H), 4.00 (m, 4H), 3.11 (m, 4H) 2.27 (s, 6H). LC-MS (ESI) m/z 529.3 (M+H).

Compound 204: $^1$H-NMR (400 MHz, CDCl$_3$): δ 1.60 (s, 6H), 1.54-1.56 (m, 3H), 2.94-2.96 (m, 3H), 3.39-3.43 (m, 4H), 3.77-3.87 (m, H), 4.70-4.85 (m, 2H), 6.43-6.60 (m, H), 6.86-6.93 (m, H), 7.17-7.31 (m, 5H), 8.46 (s, H). LC-MS (ESI) m/z 436.2 (M+H).

Compound 205: ¹H-NMR (400 MHz, CDCl₃): δ 1.52-1.54 (d, 3H), 2.28 (s, 3H), 3.21-3.48 (m, 4H), 3.91 (m, 2H), 5.39-5.44 (m, H), 6.46-6.48 (m, H), 6.65-6.72 (m, H), 7.16-7.43 (m, 5H), 8.22 (s, H).

Compound 206: ¹H-NMR (400 MHz, CDCl₃): δ 1.34-1.38 (m, 3H), 2.88-3.06 (m, 2H), 3.72-3.73 (m, 2H), 3.82-3.95 (m, 2H), 4.58 (m, H), 4.76-4.88 (m, H), 5.49-5.50 (m, H), 6.87-6.97 (m, H), 7.03-7.09 (m, H), 7.14-7.35 (m, 8H), 8.33 (s, H).

Compound 207: ¹H-NMR (400 MHz, CDCl₃): δ 0.80-0.82 (m, 2H), 1.01-1.21 (m, 2H), 1.61-1.74 (m, 3H), 1.79-1.90 (m, H), 2.95-3.04 (m, 2H), 3.94-4.06 (m, 2H), 4.78-4.89 (m, 2H), 5.31-5.38 (m, H), 7.24-7.35 (m, 5H), 8.37 (s, H). LC-MS (ESI) m/z 379.1 (M+H).

Compound 208: ¹H-NMR (300 MHz, CDCl₃): δ 8.39 (s, 1H), 7.27~7.36 (m, 5H), 6.85 (m, 1H), 6.54~6.61 (m, 1H), 5.51~5.53 (m, 1H), 5.28~5.37 (m, 1H), 4.79~4.89 (m, 2H), 3.92~4.05 (m, 4H), 3.05 (m, 2H), 1.61 (d, 3H, 6.6 Hz). LC-MS (ESI) m/z 420.2 (M+H).

Compound 209: ¹H-NMR (300 MHz, CDCl₃): δ 8.35 (s, 1H), 7.43~7.45 (m, 2H), 7.24 (m, 2H), 6.86~6.91 (m, 1H), 6.40~6.53 (m, 1H), 5.44 (m, 1H), 5.22~5.29 (m, 1H), 4.78~4.85 (m, 2H), 3.91~4.10 (m, 2H), 3.03~3.09 (m, 4H), 2.25 (s, 6H), 1.57 (d, 3H, J=6.0 Hz). LC-MS (ESI) m/z 502.1 (M+H).

Compound 210: ¹H NMR (300 MHz, CDCl₃): δ 8.33 (s, 1H), 7.31 (m, 6H), 6.98 (m, 3H), 6.49 (br, m, 1H), 6.11 (br, s, 1H), 5.58 (s, 1H), 4.85 (d, 2H), 6.22 (s, 2H), 3.77 (br, 4H), 3.08 (m, 4H), 2.29 (s, 6H). LC-MS (ESI) m/z 546.0 (M+H).

Compound 211: ¹H-NMR (400 MHz, CDCl₃): δ 0.35-0.44 (m, 4H), 1.58-1.60 (m, 4H), 3.0-3.02 (m, 2H), 3.40-3.48 (m, 2H), 3.88-3.94 (m, 2H), 4.75-4.84 (m, 2H), 5.48-5.50 (m, H), 6.37-6.47 (m, H), 6.94-6.95 (m, H), 7.24-7.34 (m, 5H), 8.35 (s, H). LC-MS (ESI) m/z 434.2 (M+H).

Compound 212: ¹H-NMR (400 MHz, CDCl₃): δ 1.23-1.32 (m, 6H), 1.43-1.60 (m, 4H), 2.15-2.23 (m, 3H), 2.89-2.98 (m, 2H), 3.05-3.13 (m, 2H), 3.91-3.97 (m, 2H), 4.78-4.84 (m, H), 6.40-6.51 (m, H), 6.90-6.92 (m, H), 7.25-7.36 (m, H), 7.25-7.36 (m, 4H), 8.38 (s, H).

Compound 213: ¹H-NMR (400 MHz, CDCl₃): δ 1.39-1.48 (m, 3H), 2.15-2.25 (m, 3H), 2.45-2.57 (m, 2H), 2.85-2.89 (m, 2H), 3.04-3.26 (m, 2H), 3.74-3.91 (m, 2H), 4.51-4.59 (m, 2H), 6.64-6.56 (m, H), 6.86-6.91 (m, H), 7.17-7.36 (m, 5H), 8.32 (s, H).

Compound 214: ¹H-NMR (300 MHz, CDCl₃): δ 8.38 (s, 1H), 7.23~7.36 (m, 5H), 6.85~6.88 (m, 1H), 6.45~6.54 (m, 1H), 5.50~5.51 (m, 1H), 5.27~5.32 (m, 1H), 4.73~4.88 (m, 4H), 3.88~3.98 (m, 2H), 3.01~3.90 (m. 2H), 2.11 (s, 3H), 1.60 (d, 3H, J=5.2 Hz). LC-MS (ESI) m/z 437.2 (M+H).

Compound 215: ¹H-NMR (400 MHz, CDCl₃): δ 1.24-1.28 (m, 3H), 2.70-2.73 (m, 4H), 3.04-3.07 (m, 2H), 3.40-3.47 (m, 2H), 3.65-3.66 (m, 4H), 3.86-3.99 (m, 2H), 4.77-4.87 (m, 2H), 5.49-5.55 (m, H), 6.64-6.70 (m, H), 6.88-6.92 (m, H), 7.26-7.40 (m, 5H), 8.38 (s, H).

Compound 216: ¹H-NMR (300 MHz, CDCl₃): δ 1.05-1.07 (m, 3H), 1.61-1.63 (m, 3H), 2.52-2.64 (m, 3H), 2.72-3.05 (m, 2H), 3.33-3.46 (m, 2H), 3.63-3.64 (m, 2H), 3.91-3.98 (m, 2H), 4.79-4.87 (m, 2H), 5.51-5.53 (m, H), 6.44-6.57 (m, H), 6.92-7.24 (m, H), 7.27-7.37 (m, 5H) 8.38 (s, H).

Compound 217: ¹H-NMR (400 MHz, CDCl₃): δ 0.92-0.94 (m, 3H), 1.28-1.44 (m, 2H), 1.85-1.92 (m, 2H), 2.26-2.31 (m, 6H), 3.10-3.13 (m, 3H), 3.94-3.99 (m, 2H), 4.78-4.86 (m, 2H), 5.37-5.41 (m, H), 6.43-6.58 (m, H), 6.88-6.92 (m, H), 7.24-7.34 (m, 5H), 8.34 (s, H).

Compound 218: ¹H NMR (300 MHz, CDCl₃): δ 8.28 (s, 1H), 7.24 (m, 9H), 6.92 (m, 1H), 6.76 (m, 1H), 6.45 (m, 1H), 5.65 (m, 1H), 4.81 (m, 2H), 4.53 (s, 2H), 6.63 (m, 4H), 3.12 (d, 2H, J=5.7 Hz), 2.95 (br, 2H), 2.28 (s, 6 h), 2.06 (br, 2H). LC-MS (ESI) m/z 560.3 (M+H).

Compound 219: ¹H NMR (300 MHz, CDCl₃): δ 8.32 (s, 1H), 7.29 (m, 7H), 7.99 (m, 3H), 6.46 (br, 1H), 6.10 (br, NH), 5.56 (br, 1H), 4.52 (d, 2H, J=3.9 Hz), 4.51 (s, 2H), 3.83 (m, 4H), 3.09 (m, 4H), 2.34 (s, 6H). LC-MS (ESI) m/z 546.1 (M+H).

Compound 220: ¹H NMR (300 MHz, CDCl₃): δ 8.32 (s, 1H), 7.30 (m, 6H), 6.99 (m, 3H), 6.32 (br, NH), 6.12 (d, 1H), 5.57 (br, 1H), 4.86 (m, 2H), 4.53 (s, 2H), 3.88 (br, 4H), 3.05 (br, 2H), 1.93 (d, 3H, J=4.8 Hz). LC-MS (ESI) m/z 503.2 (M+H).

Compound 221: ¹H NMR (300 MHz, CDCl₃): δ 8.33 (s, 1H), 7.33 (m, 7H), 6.95 (m, 3H), 6.10 (m, 1H), 5.57 (m, 1H), 4.98 (s, 1H), 4.84 (s, 1H), 4.52 (m, 2H), 4.09 (m, 1H), 3.96 (m, 1H), 3.87 (m, 2H), 3.05 (m, 4H), 2.07 (s, 3H). LC-MS (ESI) m/z 501.2 (M+H).

Compound 222: ¹H NMR (300 MHz, CDCl₃): δ 8.48 (s, 1H), 7.23 (m, 7H), 8.87 (m, 6H), 6.56 (m, 1H), 6.35 (d, 1H, J=16.8 Hz), 7.75 (d, 1H, J=9.6 Hz), 5.15 (m, 1H), 4.90 (m, 2H), 4.65 (br, 2H), 4.55 (br, 2H), 4.36 (br, 2H), 3.71 (br, 2H), 3.06 (br, 2H). LC-MS (ESI) m/z 598.3 (M+H).

Compound 223: ¹H-NMR (400 MHz, CDCl₃): δ 2.70-2.80 (m, 2H), 3.63-3.69 (m, 2H), 3.76 (s, 3H), 3.77-3.91 (m, 2H), 4.48 (s, 2H), 4.79-4.87 (m, 2H), 5.78-5.81 (m, H), 6.16-6.18 (m, H), 6.33-6.40 (m, H), 6.56-6.60 (m, H), 6.79-6.83 (m, 4H), 7.24-7.37 (m, 5H), 8.31 (s, H).

Compound 224: ¹H NMR (300 MHz, CDCl₃): δ 8.53 (d, 2H, J=5.4 Hz), 8.35 (s, 1H), 7.32 (m, 5H), 7.10 (br, 2H), 6.94 (br m, 1H), 6.55 (br m, 1H), 6.04 (br m, 1H), 5.63 (br s, 1H), 4.86 (br m, 2H), 4.57 (m, 4H), 3.99 (br m, 4H), 3.08 (br, 4H), 2.12 9br s, 6H). LC-MS (ESI) m/z 529.2 (M+H).

Compound 225: ¹H-NMR (300 MHz, CDCl₃): δ 8.36 (s, 1H), 7.23-7.30 (m, 1H), 6.95-7.06 (m, 4H), 6.56-6.59 (m, 1H), 6.33 (d, 1H, J=17.4 Hz), 5.73 (d, 1H, J=10.2 Hz), 5.59 (m, 1H), 4.72-4.85 m, 2H), 4.49 (s, 2H), 3.71-3.96 (m, 6H), 2.97 (t, 2H, J=5.7 Hz).

Compound 226: LC-MS (ESI) m/z 516.0 [M+1]⁺.

Compound 227: ¹H-NMR (400 MHz, CDCl₃): δ 2.30 (s, 3H), 3.02 (m, 2H), 3.83-3.98 (m, 4H), 4.53 (s, 2H), 4.79-4.89 (m, 2H), 5.54-5.78 (m, H), 5.80-6.16 (m, H), 6.33-6.39 (m, H), 6.59-6.63 (m, H), 7.02-7.38 (m, 9H), 8.32 (s, H). LC-MS (ESI) m/z 485.2 (M+H).

Compound 228: ¹H-NMR (400 MHz, CDCl₃): δ 2.27 (s, 6H), 2.99-3.11 (m, 4H), 3.71 (s, 3H), 3.85-4.02 (m, 4H), 4.52 (s, H), 4.80-4.87 (m, 2H), 6.12-6.14 (m, H), 6.44-6.53 (m, H), 6.83-6.93 (m, H), 7.24-7.36 (m, 9H), 8.31 (s, H).

Compound 229: ¹H-NMR (400 MHz, CDCl₃) δ 2.28 (m, 6H), 3.13 (m, 4H), 3.40 (s, 3H), 3.79 (m, 2H), 3.97~4.09 (m, 2H), 4.82~4.89 (m, 2H), 5.54 (m, 1H), 6.04~6.13 (m, 1H), 6.45~6.58 (m, 1H), 6.91~6.95 (m, 1H), 7.24~7.40 (m, 5H), 8.33 (s, 1H); LCMS-ESI (m/z): 452.0 [M+H]⁺.

Compound 230: ¹H-NMR (300 MHz, CDCl₃) δ 1.06 (t, 6H, J=6.9 Hz), 2.53~2.57 (m, 4H), 3.15 (m, 2H), 3.30 (m, 2H), 3.40 (s, 3H), 3.72~3.80 (m, 2H), 3.97~4.07 (m, 2H), 4.82~4.88 (m, 2H), 5.55 (m, 1H), 6.05~6.14 (m, 1H), 6.47~6.61 (m, 1H), 6.95~7.00 (m, 1H), 7.24~7.40 (m, 5H), 8.33 (s, 1H); LCMS-ESI (m/z): 480.0 [M+H]⁺.

Compound 231: ¹H NMR (300 MHz, CDCl₃): δ 8.54 (m, 2H), 8.42 (s, 1H), 7.53 (d, 1H, J=7.5 Hz), 7.29 (m, 6H), 6.91 (br, 1H), 6.45 (m, 1H), 6.06 (br, NH), 5.59 (br, 1H), 4.84 (m, 2H), 4.51 (s, 2H), 3.83 (m, 4H), 3.11 (m, 4H), 2.29 (s, 6H). LC-MS (ESI) m/z 529.1 (M+H).

Compound 232: ¹H NMR (300 MHz, CDCl₃): δ 8.29 (s, 1H), 7.25 (m, 9H), 6.92 (br m, 1H), 6.45 (m, 1H), 6.19 (br, 1H), 5.58 (br s, 1H), 4.85 (br m, 2H), 4.60 (br s, 2H), 3.89 (br m, 4H), 3.08 (br m, 4H), 2.28 (s, 6 h), 2.28 (br s, 6H). LC-MS (ESI) m/z 546.1 (M+H).

Compound 233: ¹H-NMR (400 MHz, CDCl₃): δ 8.30 (s, H) 7.22-7.36 (m, 5H), 6.45-6.47 (d, 1H), 5.44-5.41 (m, H), 4.09-3.89 (m, 4H), 3.26-3.29 (t, 2H), 3.06-3.09 (t, 2H), 0.82-0.84 (m, 15H).

Compound 234: ¹H-NMR (400 MHz, CDCl₃): δ 8.26 (1H, s), 7.36-7.03 (5H, m), 6.10 (1H, d, J=6.4 Hz), 5.90 (1H, t, J=3.6 Hz), 5.41 (1H, q, J=4.0 Hz), 4.11-3.88 (4H, m), 3.15-3.01 (2H, m) 2.99-2.13 (6H, m), 1.69-1.57 (4H, m).

Compound 235: ¹H NMR (400 MHz, CDCl₃): δ 8.30 (s, 1H), 7.28-7.38 (m, 5H), 5.99 (d, 1H, J=6.0 Hz), 5.41 (t, 1H, J=4.8 Hz), 4.79 (m, 2H), 3.96-4.02 (m, 2H), 3.82-3.85 (m, 2H), 3.09-3.16 (m, 2H), 2.48 (s, 1.8H), 2.45 (s, 1.2H), LC-MS (ESI) m/z 397.0 [M+H]⁺.

Compound 327: ¹H NMR (CDCl₃, 400 MHz) δ 8.31 (s, 1H), 7.38~7.28 (m, 5H), 6.90 (d, J=10 Hz, 1H), 6.62 (t, J=16.8 Hz, 1H), 6.02 (s, 1H), 5.39 (d, J=5.2 Hz, 1H), 4.84 (d, J=16.8 Hz, 2H), 4.00 (s, 3H), 3.93 (s, 2H), 3.62 (s, 1H), 3.47 (t, J=5 Hz, 2H), 3.34 (d, J=5 Hz, 4H), 3.23 (s, 2H), 2.57 (s, 2H), 2.31 (s, 3H). LCMS-ESI m/z 482.1 (M+H)⁺.

Example 5

Synthesis of S-2-(5,6-diphenyl-furo[2,3-d]pyrimidin-4-ylamino)-2-phenyl-ethanol (Compound 31)

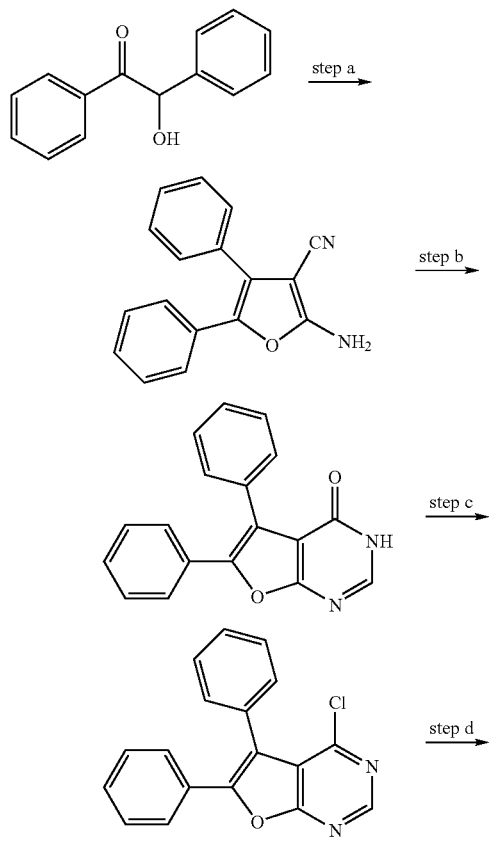

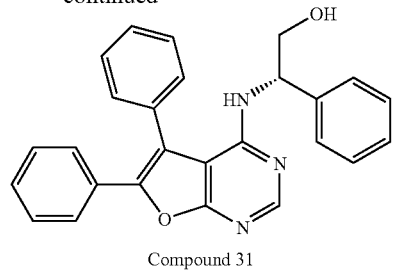

Compound 31

2-Amino-4,5-diphenylfuran-3-carbonitrile (step a)

Diethylamine (13.8 g) was added dropwise over a period of 30 min to a mixture of benzoin (10 g) and malononitrile (3.8 g) in DMF (30 ml) at 0° C. (the internal temperature should not exceed 40° C.). After the resulting mixture was stirred at room temperature for 16 h, water (100 mL) was added. The resulting precipitate was filtered, washed with sufficient amount of water, then with hexanes, and dried. The solid was recrystallized from ethanol to provide yellowish-brown solid product of the title compound (6 g, 49%). ¹H NMR (300 MHz, CDCl₃): δ 7.47-7.34 (m, 8H), 7.28-7.18 (m, 2H), 4.94 (br, 2H). LC-MS (ESI) m/z 261.1 (M+H).

5,6-Diphenylfuro[2,3-d]pyrimidin-4(3H)-one (step b)

A mixture of 2-amino-4,5-diphenylfuran-3-carbonitrile (2.0 g) and formic acid (24 mL) was cooled to 0° C. and acetic anhydride (24 mL) was added dropwise. The resulting mixture was stirred for another 1 h and was then heated at 100° C. for 16 h. The reaction mixture was cooled and water was added (40 mL). The precipitate was collected by filtration and washed thoroughly with water and hexanes to give the title compound (2.1 g, 95%). ¹H NMR (300 MHz, CDCl₃): δ 7.94 (s, 1H), 7.56-7.52 (m, 4H), 7.46-7.43 (m, 3H), 7.32-7.28 (m, 3H), 7.22 (s, 1H). LC-MS (ESI) m/z 289.1 (M+H).

4-Chloro-5,6-diphenylfuro[2,3-d]pyrimidine (step c)

A mixture of 5,6-diphenylfuro[2,3-d]pyrimidin-4(3H)-one (3 g) and POCl₃ (30 mL) was heated at 55-65° C. for 3 h. Water was then added followed by sodium bicarbonate. The resulting mixture was extracted with ethyl acetate. The organic layer was concentrated and the crude compound was purified by silica gel column chromatography using a mixture of hexanes:ethyl acetate (95:5) to give the title compound as a white solid (2 g, 63%). ¹H NMR (300 MHz, CDCl₃): δ 8.77 (s, 1H), 7.61-7.58 (m, 2H), 7.52-7.46 (m, 5H), 7.35-7.32 (m, 3H). LC-MS (ESI) m/z 307.0 (M+H).

S-2-(5,6-Diphenyl-furo[2,3-d]pyrimidin-4-ylamino)-2-phenyl-ethanol (Compound 31, step d)

A mixture of 4-chloro-5,6-diphenylfuro[2,3-d]pyrimidine (0.160 g) and S-2-amino-2-phenyl-ethanol (0.137 g, 2 eq) in n-butanol (5 mL) was heated at 80° C. for 16 h. The reaction mixture was concentrated and the residue was partitioned between water and ethyl acetate. The organic layer was concentrated and the crude compound was purified by silica gel column chromatography using a mixture of dichloromethane:methanol (40:1) to give the title compound (0.140 g, 69%). ¹H NMR (300 MHz, CDCl₃): δ 8.31 (s, 1H), 7.50-7.47 (m, 2H), 7.45 (br s, 4H), 7.47-7.40 (m, 7H), 6.94 (m, 2H), 5.24 (d, 1H, J=5.6 Hz), 5.16 (m, 1H), 3.72 (m, 2H). LC-MS (ESI) m/z 408.5 (M+H).

Example 6

Synthesis of S—N-(3-(4-(2-hydroxy-1-phenylethylamino)-6-phenylfuro[2,3-d]pyrimidin-5-yl)phenyl)acrylamide (Compound 236)

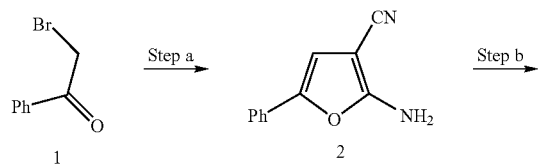

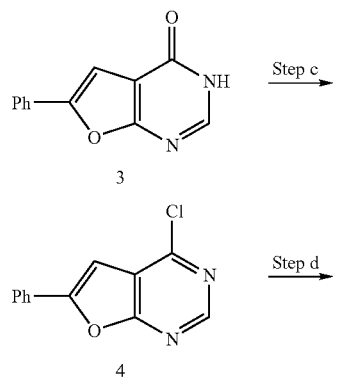

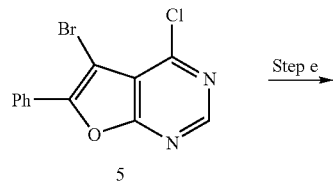

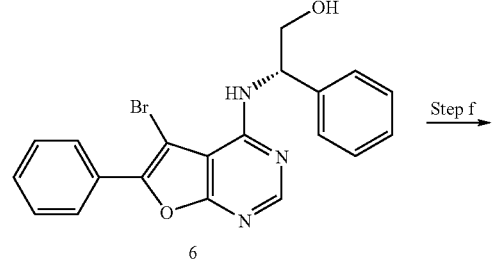

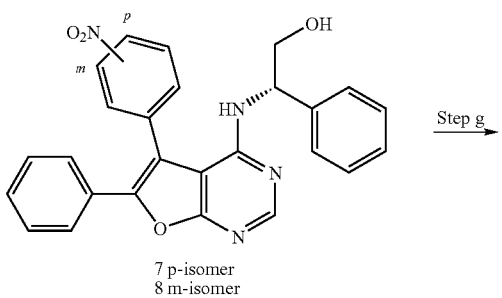

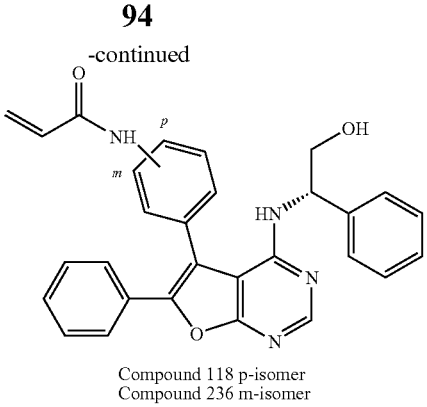

Compound 118 p-isomer
Compound 236 m-isomer

2-Amino-5-phenyl-furan-3-carbonitrile (2 from step a)

2 was prepared in 38% yield from 2-bromo acetophenone (1), similar to 2-amino-4,5-diphenylfuran-3-carbonitrile (see Example 5 above). $^1$H NMR (300 MHz, CDCl$_3$) δ 7.50-7.47 (m, 2H), 7.39-7.33 (m, 2H), 7.27-7.25 (m, 1H), 6.54 (s, 1H), 4.86 (br, 2H). LCMS (ESI) m/z 185.0 (M+H)$^+$.

6-Phenyl-3H-furo[2,3-d]pyrimidin-4-one (3 from step b)

3 was prepared in 80% yield from 2, similar to 5,6-diphenylfuro[2,3-d]pyrimidin-4(3H)-one (see Example 5 above). $^1$H NMR (300 MHz, CD$_3$OD) δ 9.00 (br, 1H), 8.36 (br, 1H), 7.67 (d, J=7.5 Hz, 2H), 7.44-7.38 (m, 2H), 7.32-7.25 (m, 1H), 7.10 (s, 1H). LCMS (ESI) m/z 235.0 (M+Na)$^+$.

4-Chloro-6-phenyl-furo[2,3-d]pyrimidine (4 from step c)

4 was prepared in 94% yield from 3, similar to 4-chloro-5,6-diphenylfuro[2,3-d]pyrimidine (see Example 5 above). $^1$H NMR (300 MHz, CDCl$_3$) δ 8.75 (s, 1H), 7.93-7.89 (m, 2H), 7.55-7.26 (m, 3H), 7.09 (s, 1H). LCMS (ESI) m/z 231.0 (M+H)$^+$.

5-Bromo-4-chloro-6-phenyl-furo[2,3-d]pyrimidine (5 from step d)

N-Bromosuccinimide (1.16 g, 6.50 mmol) was added portion wise to 4-chloro-6-phenyl-furo[2,3-d]pyrimidine (4) (1.0 g, 4.33 mmol) in 20 mL DMF. After the resulting mixture was stirred at room temperature for 3 h, water (100 mL) was added. The resulting precipitate was filtered, washed with water, the crude compound was purified by silica gel column chromatography using a mixture of ethyl acetate:n-hexane (1:10), to provide 5 (1.14 g, 85%). $^1$H NMR (300 MHz, CDCl$_3$): δ 8.75 (s, 1H), 8.20-8.16 (m, 2H), 7.55-7.51 (m, 3H). LCMS (ESI) m/z 308.9 (M+H)$^+$, 310.9 (M+2+H)$^+$.

S-2-(5-Bromo-6-phenyl-furo[2,3-d]pyrimidin-4-ylamino)-2-phenyl-ethanol (6 from step e)

4-5-Bromo-4-chloro-6-phenyl-furo[2,3-d]pyrimidine (5) (0.2 g; 1 equiv) and (S)-(+)-phenylglycinol (1.5 equiv) in n-butanol (5 mL) were heated at 80° C. for 16 h. The reaction mixture was concentrated and the residue was partitioned between water (50 mL) and ethyl acetate (3×50 mL). The organic layer was concentrated and the crude compound was purified by silica gel column chromatography using a mixture of dichloromethane:methanol (40:1), to give 2-(5-bromo-6-phenyl-furo[2,3-d]pyrimidin-4-ylamino)-2-phenyl-ethanol (6) in 69% yield. ¹H NMR (300 MHz, CDCl₃): δ 8.30 (s, 1H), 8.07-8.02 (m, 2H), 7.51-7.30 (m, 8H), 6.89 (d, J=6.9 Hz, 1H), 5.50-5.45 (m, 1H), 4.05 (d, J=4.8 Hz, 2H), 3.39 (brs, 1H). LCMS (ESI) m/z 411.1 (M+H⁺).

S-2-[5-(4-Nitro-phenyl)-6-phenyl-furo[2,3-d]pyrimidin-4-ylamino]-2-phenyl-ethanol (7 from step f)

A mixture of 6 (410 mg, 1.0 mmol) and p-nitrobenzene boronic acid (195 mg, 1.2 mmol), was dissolved in dioxane (2.0 mL) under nitrogen atmosphere. Added Pd(dppf)₂Cl₂ (4.2 mg, 0.05 mmol) and Na₂CO₃ solution (2 M, 1.0 mL) to this mixture and heated at 95° C. for 16 h under nitrogen. After completion, the reaction mixture was cooled to room temperature, added water and extracted with ethyl acetate (3×20 mL). Combined organics dried over NaSO₄, and concentrated under vacuum and the residue obtained was purified over silica gel flash column chromatography using hexane:ethyl acetate=1:1 to give 7 (346 mg, 77%). ¹H NMR (300 MHz, CDCl₃): δ 8.41 (s, 1H), 8.29 (d, J=8.4 Hz, 2H), 7.67 (d, J=8.4 Hz, 2H), 7.50-7.47 (m, 2H), 7.34-7.26 (m, 6H), 7.09-7.05 (m, 2H), 5.23 (dd, J=10.2, 5.4 Hz, 1H), 5.16 (d, J=5.4 Hz, 1H), 3.88-3.84 (m, 2H), 3.31 (t, J=5.4 Hz, 1H). LC-MS (ESI) m/z 453.1 (M+H)⁺.

S-2-[5-(3-Nitro-phenyl)-6-phenyl-furo[2,3-d]pyrimidin-4-ylamino]-2-phenyl-ethanol (8 from step f)

8 was synthesized in 75% yield from 6, in a manner similar to 7 using m-nitrobenzene boronic acid. ¹H NMR (300 MHz, CDCl₃): δ 8.41 (s, 2H), 8.30 (ddd, J=8.1, 1.2, 1.2 Hz, 1H), 7.82 (dd, J=7.8, 1.2 Hz, 1H), 7.65 (dd, J=8.1, 7.8 Hz, 1H), 7.50-7.47 (m, 2H), 7.34-7.26 (m, 6H), 7.11-7.07 (m, 2H), 5.27-5.20 (m, 2H), 3.88-3.84 (m, 2H), 3.31 (t, J=5.4 Hz, 1H). LC-MS (ESI) m/z 453.1 (M+H)⁺.

S—N-{4-[4-(2-Hydroxy-1-phenyl-ethylamino)-6-phenyl-furo[2,3-d]pyrimidin-5-yl]-phenyl}-acrylamide (Compound 118 from step g)

A mixture of 7 (136 mg, 0.3 mmol) and 5% Pd/C (10 mg) in EtOH (3 mL) was hydrogenated at atmospheric pressure for 16 h. Filtered the reaction mixture over celite, removed solvents under vacuum to give 2-[5-(4-amino-phenyl)-6-phenyl-furo[2,3-d]pyrimidin-4-ylamino]-2-phenyl-ethanol. To a mixture of the above compound and pyridine (0.05 mL, 0.6 mmol) in a solution of ether (3 mL), was added acryloyl chloride (0.03 mL, 0.33 mmol) and stirred the reaction mixture at room temperature for 16 h. Added water, and extracted with ethyl acetate (3×20 mL). Combined organics dried over MgSO₄, concentrated under vacuum and the residue purified over silica gel flash column chromatography using hexane:ethyl acetate=2:3 to give Compound 118 (29 mg, 20%). ¹H NMR (300 MHz, CDCl₃) δ 8.33 (s, 1H), 8.00 (brs, 1H), 7.80-7.71 (m, 2H), 7.57 (d, J=8.4 Hz, 2H), 7.47-7.44 (m, 3H), 7.30-7.19 (m, 5H), 7.07 (d, J=8.4 Hz, 2H), 6.50 (d, J=16.8 Hz, 1H), 6.32 (dd, J=16.8, 10.2 Hz, 1H), 5.83 (d, J=10.2 Hz, 1H), 5.45 (d, J=6.3 Hz, 1H), 5.20-5.18 (m, 1H), 3.86-3.73 (m, 2H). LCMS (ESI) m/z 477.1 (M+H).

S—N-{3-[4-(2-Hydroxy-1-phenyl-ethylamino)-6-phenyl-furo[2,3-d]pyrimidin-5-yl]-phenyl}-acrylamide (Compound 236 from step g)

Compound 236 was synthesized in 25% yield from 8, in a manner similar to Compound 118. ¹H NMR (300 MHz, CDCl₃): δ 8.58 (brs, 1H), 8.27 (s, 1H), 7.79-7.64 (m, 2H), 7.49-7.46 (m, 2H), 7.40 (t, J=7.5 Hz, 1H), 7.27-7.20 (m, 8H), 7.05-7.02 (d, J=7.5 Hz, 2H), 6.46 (d, J=16.8 Hz, 1H), 6.28 (dd, J=16.8, 10.2 Hz, 1H), 5.73 (d, J=10.2 Hz, 1H), 5.64 (d, J=6.0 Hz, 1H), 5.30 (brs, 1H), 3.86 (dd, J=11.4, 2.7 Hz, 1H), 3.69 (dd, J=11.4, 6.9 Hz, 1H). HRMS (EI) calcd. for C₂₉H₂₄N₄O₃ 476.1848. found 476.1843.

Example 7

Synthesis of (S,E)-4-(dimethylamino)-N-(3-(4-(2-hydroxy-1-phenylethylamino)-6-phenylfuro[2,3-d]pyrimidin-5-yl)phenyl)but-2-enamide (Compound 243)

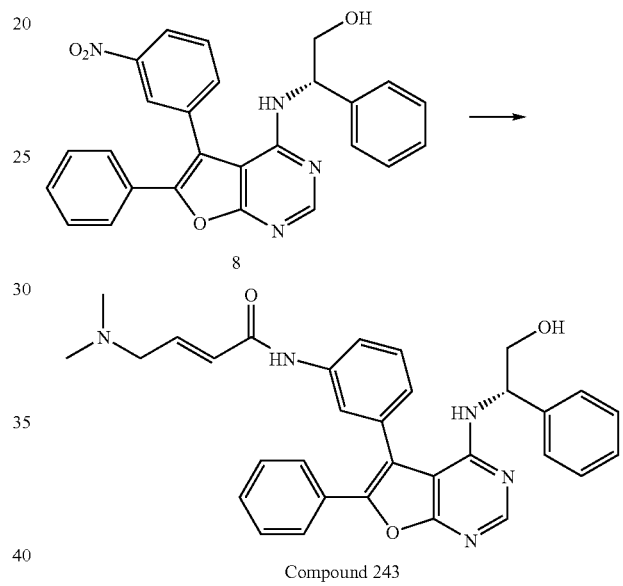

Compound 243

A mixture of 8 (1 g, 0.002 mmol, see Example 6 above) and 5% Pd/C (10 mg) in MeOH (10 mL) was hydrogenated at 3 atmospheric pressure for 8 h. Filtered the reaction mixture over celite, removed solvents under vacuum to give S-2-[5-(3-amino-phenyl)-6-phenyl-furo[2,3-d]pyrimidin-4-ylamino]-2-phenyl-ethanol. To a mixture of the above compound in DCM (5 mL), was added 4-bromocrotonoic acid (422 mg, 2.55 mmol), EDCI (490 mg, 2.55 mmol) and stirred the reaction mixture for 8 h. Then added N,N-dimethylamine (1.18 ml, 23.2 mmol) and continued stirring for 8 h at room temperature. Added water to the reaction mixture and extracted with dichloromethane (3×20 mL). Combined organics dried over MgSO₄, concentrated under vacuum and the residue purified over silica gel flash column chromatography using dichloromethane:methanol (20:1) to give Compound 243 (370 mg, 30%).

¹H NMR (300 MHz, CDCl₃): δ 8.32 (s, 1H), 8.20 (brs, 1H), 7.78-7.73 (m, 2H), 7.54-7.51 (m, 2H), 7.42 (t, J=7.8 Hz, 1H), 7.27-7.18 (m, 7H), 7.05-7.02 (m, 2H), 6.94 (dt, J=15.9, 6.0 Hz, 1H), 6.14 (d, J=15.9 Hz, 1H), 5.67 (d, J=6.6 Hz, 1H), 5.34 (brs, 1H), 3.87 (dd, J=11.4, 2.7 Hz, 1H), 3.67 (dd, J=11.4, 6.9 Hz, 1H), 2.71 (brs, 1H), 2.25 (s, 6H). LC-MS (ESI) m/z 534.1 (M+H).

Example 8

Syntheses of Compounds 32-58, 237-242, 244, and 247

Compounds 32-58, 237-242, 244, and 247 were prepared in a manner described in Example 5, 6, or 7. $^1$H NMR and MS data of these compounds are listed below.

Compound 32: $^1$H NMR (300 MHz, CDCl$_3$): δ 8.39 (s, 1H), 7.58-7.26 (m, 13H), 6.99 (m, 2H), 5.35 (d, 1H, J=6.3 Hz), 5.26 (m, 1H), 3.80 (m, 2H). LC-MS (ESI) m/z 408.1 (M+H).

Compound 33: LC-MS (ESI) m/z 422.1 (M+H)$^+$.

Compound 34: LC-MS (ESI) m/z 422.2 (M+H)$^+$.

Compound 35: $^1$H NMR (300 MHz, CDCl$_3$): δ 8.37 (s, 1H), 7.58 (m, 2H), 7.35-7.26 (m, 8H), 5.19 (dd, 1H, J$_1$=5.7 Hz, J$_2$=10.5 Hz), 3.86 (s, 3H), 3.80 (dd, 2H, J$_1$=4.5 Hz, J$_2$=10.8 Hz). LC-MS (ESI) m/z 438.7 (M+H).

Compound 36: $^1$H NMR (300 MHz, CDCl$_3$): δ 8.35 (s, 1H), 7.50 (m, 2H,), 7.33-7.26 (m, 7H), 7.03 (m, 2H), 6.81 (m, 2H), 5.31 (d, 1H, J=5.7 Hz), 5.17 (dd, 1H, J$_1$=5.4 Hz, J$_2$=10.2 Hz), 3.85 (s, 3H), 3.81 (m, 2H), 3.76 (s, 3H). LC-MS (ESI) m/z 468.4 (M+H).

Compound 37: $^1$H NMR (300 MHz, CDCl$_3$): δ 8.35 (s, 1H), 7.57 (m, 3H,), 7.45 (d, 2H, J=7.5 Hz), 7.32-7.26 (m, 6H), 7.07 (m, 3H), 5.41 (d, 1H, J=6.3 Hz), 5.20 (dd, 1H, J$_1$=6.3 Hz, J$_2$=9.3 Hz), 3.78 (m, 2H), 2.25 (s, 3H). LC-MS (ESI) m/z 465.7 (M+H).

Compound 38: $^1$H NMR (300 MHz, CDCl$_3$): δ 8.28 (s, 1H), 7.65 (m, 2H), 7.49 (m, 2H), 7.40, (t, 1H, J=8.4 Hz), 7.26-7.15 (m, 7H), 7.05 (m, 2H), 5.61 (d, 1H, J=6.0 Hz), 5.30 (br, 1H), 3.84 (m, 1H), 3.70 (dd, 1H, J$_1$=6.3 Hz, J$_2$=10.8 Hz), 2.14 (s, 3H). LC-MS (ESI) m/z 465.7 (M+H).

Compound 39: $^1$H NMR (300 MHz, CDCl$_3$): δ 8.36 (s, 1H), 7.59 (m, 2H), 7.49 (m, 2H), 7.36-7.26 (m, 7H), 7.10 (m, 2H), 6.05 (s, 2H), 5.46 (d, 1H, J=5.1 Hz), 5.21 (dd, 1H, J$_1$=5.4 Hz, J$_2$=10.5 Hz), 3.85 (d, 2H, J=6.8 Hz). LC-MS (ESI) m/z 452.6 (M+H).

Compound 40: $^1$H NMR (300 MHz, CDCl$_3$): δ 8.38 (s, 1H), 7.28 (m, 2H), 7.42-7.26 (m, 8H), 6.88 (d, 1H, J=6.0 Hz), 6.49 (m, 2H), 5.35 (dd, 1H, J$_1$=3.9 Hz, J$_2$=15 Hz), 3.99 (dd, 2H, J$_1$=7.5 Hz, J$_2$=11.4 Hz). LC-MS (ESI) m/z 398.6 (M+H).

Compound 41: $^1$H NMR (300 MHz, CDCl$_3$): δ 8.36 (s, 1H), 7.68 (m, 2H), 7.62 m, (2H), 7.38-7.28 (m, 6H), 7.26 (m, 2H), 6.54 (m, 1H), 5.75 (d, 1H, J=6.3 Hz), 5.30 (q, 1H, J=5.4 Hz), 3.89 (m, 2H). LC-MS (ESI) m/z 398.7 (M+H).

Compound 42: $^1$H NMR (300 MHz, CDCl$_3$): δ 8.35 (s, 1H), 7.78 (m, 2H), 7.46-7.33 (m, 8H), 6.87 (s, 1H), 5.38 (d, 1H, J=5.7 Hz), 4.08 (d, 2H, J=5.1 Hz). LC-MS (ESI) m/z 332.6 (M+H).

Compound 43: $^1$H NMR (300 MHz, CDCl$_3$): δ 8.32 (s, 1H), 8.06 (m, 2H), 7.52-7.26 (m, 8H), 6.90 (d, 1H, J=7.2 Hz), 5.48 (m, 1H), 4.05 (m, 2H). LC-MS (ESI) m/z 411.1 (M+H).

Compound 44: $^1$H NMR (300 MHz, CDCl$_3$): δ 8.35 (s, 1H), 8.07 (m, 2H), 7.52-7.26 (m, 8H), 5.79 (m, 1H), 4.57 (dd, 1H, J$_1$=7.2 Hz, J$_2$=11.7 Hz), 4.45 (dd, 1H, J$_1$=4.8 Hz, J$_2$=11.4 Hz). LC-MS (ESI) m/z 452.0 (M+H).

Compound 45: $^1$H NMR (300 MHz, CDCl$_3$): δ 8.35 (s, 1H), 8.06 (m, 2H), 7.53-7.26 (m, 8H), 6.65 (d, 1H, J=7.2 Hz), 5.48 (m, 1H), 4.07 (m, 2H), 3.03 (br, 1H). LC-MS (ESI) m/z 366.5 (M+H).

Compound 46: $^1$H NMR (300 MHz, CDCl$_3$): δ 8.40 (s, 1H), 7.60-7.57 (m, 6H), 7.33-7.21 (m, 9H), 5.84 (d, 1H, J=9.0 Hz), 5.71 (d, 1H, J=6.6 Hz), 3.68 (s, 3H). LC-MS (ESI) m/z 436.2 (M+H).

Compound 47: LC-MS (ESI) m/z 450.6 (M+H)$^+$.

Compound 48: LC-MS (ESI) m/z 464.2 (M+H)$^+$.

Compound 49: LC-MS (ESI) m/z 478.2 (M+H)$^+$.

Compound 50: $^1$H NMR (300 MHz, CDCl$_3$+CD$_3$OD): δ 8.19 (s, 1H), 7.44-7.42 (m, 7H), 7.24-7.17 (m, 8H), 5.55 (s, 1H). LC-MS (ESI) m/z 422.1 (M+H).

Compound 51: LC-MS (ESI) m/z 421.2 (M+H)$^+$.

Compound 52: LC-MS (ESI) m/z 480.0 (M+H)$^+$.

Compound 53: LC-MS (ESI) m/z 424.0 (M+H)$^+$.

Compound 54: LC-MS (ESI) m/z 406.5 (M+H)$^+$.

Compound 55: LC-MS (ESI) m/z 406.6 (M+H)$^+$.

Compound 56: $^1$H NMR (300 MHz, CDCl$_3$): δ 8.36 (s, 1H), 7.32 (d, 2H, J=7.8 Hz), 7.42-7.24 (m, 8H), 6.83 (s, 1H), 5.73 (br, 1H), 5.21 (d, 1H, J=7.2 Hz), 1.99 (m, 2H), 1.00 (t, 3H, J=7.5 Hz). LC-MS (ESI) m/z 330.1 (M+H)$^+$.

Compound 57: $^1$H NMR (300 MHz, CDCl$_3$): δ 8.35 (s, 1H), 8.03 (m, 2H), 7.51-7.44 (m, 2H), 7.42-7.34 (m, 5H), 7.31-7.34 (m, 1H), 6.17 (d, 1H, J=7.8 Hz), 6.35 (q, 1H, J=7.8 Hz), 2.01 (m, 2H), 0.99 (t, 3H, J=7.5 Hz). LC-MS (ESI) m/z 363.9 (M+H)$^+$.

Compound 58: LC-MS (ESI) m/z 310.1 (M+H)$^+$.

Compound 237: $^1$H NMR (300 MHz, CDCl$_3$,): δ 8.34 (s, 1H), 7.53 (m, 4H), 7.41 (m, 3H), 7.27 (m, 7H), 7.15 (m, 2H), 6.96 (m, 1H), 6.85 (d, 1H, J=7.5 Hz), 6.77 (d, J=9.6 Hz), 5.55 (m, 1H), 5.46 (m, 1H), 4.34 (d, 2H, J=5.4 Hz), 3.67 (m, 1H), 3.54 (m, 1H). LC-MS (ESI) m/z 516.2 (M+H).

Compound 238: H NMR (300 MHz, CDCl$_3$): δ 8.38 (s, 1H), 7.85-7.70 (m, 3H), 7.75-7.44 (m, 3H), 7.29-7.20 (m, 6H), 7.12 (d, J=6.9 Hz, 2H), 6.52 (d, J=16.8 Hz, 1H), 6.34 (dd, J=16.8, 9.9 Hz, 1H), 5.85 (d, J=9.9 Hz, 1H), 5.87-5.82 (m, 1H), 4.99 (d, J=7.8 Hz, 1H), 1.38 (d, J=6.9 Hz, 3H). LC-MS (ESI) m/z 461.2 (M+H).

Compound 239: $^1$H NMR (300 MHz, CDCl$_3$): δ 8.38 (s, 1H), 7.96-7.91 (m, 1H), 7.55-7.47 (m, 5H), 7.29-7.18 (m, 6H), 7.12 (d, J=6.6 Hz, 2H), 6.46 (d, J=16.8 Hz, 1H), 6.23 (dd, J=16.8, 10.2 Hz, 1H), 5.80 (d, J=10.2 Hz, 1H), 5.36-5.28 (m, 1H), 5.04 (d, J=7.5 Hz, 1H), 1.38 (d, J=6.6 Hz, 3H). LC-MS (ESI) m/z 461.2 (M+H).

Compound 240: $^1$H NMR (300 MHz, CDCl$_3$): δ 8.36 (s, 1H), 8.11 (brs, 1H), 7.57-7.47 (m, 4H), 7.30-7.21 (m, 8H), 7.08-7.06 (m, 2H), 6.47 (d, J=16.8 Hz, 1H), 6.28 (dd, J=16.8, 8.1 Hz, 2H), 5.99 (dd, J=16.8, 10.2 Hz, 1H), 5.82-5.77 (m, 2H), 5.33 (d, J=8.4 Hz, 1H), 4.50 (brs, 1H), 4.30-4.20 (m, 1H). LC-MS (ESI) m/z 531.0 (M+H).

Compound 241: $^1$H NMR (300 MHz, CDCl$_3$): δ 8.37 (s, 1H), 7.67-7.64 (m, 2H), 7.56-7.52 (m, 3H), 7.42 (t, J=7.8 Hz, 1H), 7.29-7.22 (m, 7H), 7.07-7.04 (m, 2H), 5.48-5.47 (m, 1H), 5.30-5.29 (m, 1H), 3.88-3.75 (m, 3H), 2.01 (s, 3H). LC-MS (ESI) m/z 489.1 (M+H).

Compound 242: $^1$H NMR (300 MHz, CDCl$_3$): δ 8.35 (s, 1H), 7.76-7.73 (m, 2H), 7.61-7.21 (m, 11H), 7.06-7.03 (m, 2H), 5.54-5.53 (m, 1H), 5.00-4.97 (m, 1H), 4.04-4.02 (m, 2H), 3.49 (s, 3H), 2.28 (s, 3H). LC-MS (ESI) m/z 503.1 (M+H).

Compound 244: $^1$H NMR (300 MHz, CDCl$_3$): δ 8.24 (s, 1H), 8.04 (s, 1H), 7.65 (d, J=8.4 Hz, 1H), 7.50-7.29 (m, 9H), 7.00 (brs, 1H), 6.48 (d, J=16.8 Hz, 1H), 6.38 (dd, J=16.8, 9.6 Hz, 1H), 5.78 (d, J=9.6 Hz, 1H), 5.38 (brs, 1H), 4.03-3.97 (m, 2H), 2.32 (s, 1H). LC-MS (ESI) m/z 401.0 (M+H).

Compound 247: $^1$H-NMR (400 MHz, CDCl$_3$): δ 2.24 (s, 3H), 3.44 (s, 3H), 3.79-3.83 (m, H), 3.99-4.01 (m, H), 5.77-5.80 (d, H), 6.19-6.30 (m, H), 6.39-6.47 (d, 2H), 7.03-7.48 (m, 10H), 8.46 (s, H).

Example 9

Inhibiting EGFR Kinase Activity

The EGFR kinase assay was carried out in a 96-well plate at 37° C. for 60 min with a 50 μl mixture including the following components: 50 ng GST-EGFR-KD$^{WT}$ proteins, 25 mM Tris-HCl, pH 7.5, 4 mM MnCl$_2$, 2 mM DTT, 10 mM MgCl$_2$, 0.1 mg/ml bovine serum albumin, 10 μM poly(Glu, Tyr) 4:1, 0.5 mM Na$_3$VO$_4$, 5 μM ATP and a test compound. Following incubation, 50 μl Kinase-Glo Plus Reagent (Promega) was added and the mixture was further incubated at 25° C. for 20 min. A 70 μl aliquot of each reaction mixture was transferred to a black microtiter plate and the luminescence was measured on Wallac Vector 1420 multilabel counter (PerkinElmer).

GST-EGFR-KD$^{WT}$ protein expression and purification were done in a manner as set forth in Analytical Biochemistry 377 (2008) 89-94.

Compounds 1-68, 75, 106, 107, 118, 154, 176, 178, 180, 181, 183-247, and 327 were tested in this assay. Unexpectedly, Compounds 1, 7, 8, 15, 18, 20, 22, 23, 31, 35, 38-43, 45, 61, 154, 181, 188, 192, 204, 206, 238-240, 242, and 247 showed IC$_{50}$ values (i.e., the concentration of a test compound at which activity of 50% of EGFR is inhibited) between 101 nM and 0.9 μM; Compounds 36, 37, 63, 118, 186, 220, 230, and 244 showed IC$_{50}$ values between 60 and 100 nM; and Compounds 12, 50, 53, 62, 64-67, 75, 106, 107, 176, 178, 185, 187, 190, 191, 193-195, 198-200, 202, 203, 205, 208-219, 223, 224, 226-229, 231-233, 236, 241, 243, 245, 246, and 327 and showed IC$_{50}$ values lower than 59 nM.

Example 10

In Vitro Anticancer Activity

HCC827 cell viability was examined by the MTS assay (Promega, Madison, Wis., USA). 1000 HCC827 cells in 100 μl RPMI1640 with 10% FBS medium were seeded in each well of a 96-well plate. After 96-h incubation with a test compound, the cells were further incubated with 20 μl of a MTS/PMS mixture (MTS/PMS ratio: 20:1) in each well of the 96-well plate for 2 h at 37° C. in a humidified incubator with 5% CO$_2$ to allow viable cells to convert the tetrazolium salt (MTS) into formazan. The amount/concentration of formazan, which indicates the number of live cells, was determined by measuring its absorbance at 490 nm using a PerkinElmer Victor2 plate reader (PerkinElmer, Shelton, Conn., USA).

Based on the test results in Example 9, only Compounds 1, 3-5, 7-8, 12, 15, 23, 31, 35, 37-51, 53, 54, 56, 62-68, 75, 106, 107, 118, 176, 178, 181, 185-188, 190-195, 198, 200, 202-206, 208-219, 223, 224, 226-232, 236, 238, 239, 241, and 243-246 were tested in this assay. Unexpectedly, Compounds 3, 4, 15, 23, 31, 40, 42, 44, 46, 47, 54, 56, 118, 186, 188, 193, 206, and 244 showed IC$_{50}$ values (i.e., the concentration of a test compound which causes 50% of the cell death) between 301 nM and 999 nM; Compounds 1, 35, 37-39, 41, 63, 202, and 245 showed IC$_{50}$ values between 100 nM and 300 nM; and Compounds 12, 62, 64-68, 75, 106, 107, 176, 178, 181, 185, 187, 190-192, 194, 195, 198, 200, 203-205, and 208-219, 223, 224, 226-232, 236, 238, 239, 241, 243, and 246 showed IC$_{50}$ values between 1 nM, and 99 nM.

Example 11

Double Mutant EGFR Kinase Assay

GST-EGFR-KD$^{L858R/T790M}$ containing the EGFR kinase catalytic domain (residues from 696 to 1022 and with L858R/T790M) were expressed in Sf9 insect cells transfected with the baculovirus containing pBac-PAK8-GST-EGFR-KD$^{L858R/T790M}$ plasmid. GST-EGFR-KD$^{L858R/T790}$M protein expression and purification were done in a manner similar to that reported earlier (Analytical Biochemistry 377 (2008) 89-94).

The EGFR$^{L858R/T790M}$ Kinase-Glo assays were carried out in 96-well plates at 37° C. for 60 min in a final volume of 50 μL including the following components: 200 ng GST-EGFR-KD$^{L858R/T790M}$ proteins, 25 mM HEPES, pH 7.4, 4 mM MnCl$_2$, 2 mM DTT, 10 mM MgCl$_2$, 0.1 mg/ml bovine serum albumin, 10 μM poly(Glu,Tyr) 4:1, 0.5 mM Na$_3$VO$_4$, 1 μM ATP, and a test compound. Following incubation, 50 μL Kinase-Glo Plus Reagent (Promega) was added and the mixture was incubated at 25° C. for 20 min. A 70 μL aliquot of each reaction mixture was transferred to a black microtiter plate and the luminescence was measured on Wallac Vector 1420 multilabel counter (PerkinElmer).

Compounds 9, 11-16, 36, 59-68, 75, 106, 107, 118, 154, 176, 178, 180, 181, and 183-236, 238-241, 243, 245-247, and 327 were tested in this assay. Unexpectedly, Compounds 63-67, 75, 106, 178, 188, 190, 191, 193, 198, 203, 205, 211, 215, 228, 232, 239, and 241 showed IC$_{50}$ values (i.e., the concentration of a test compound at which activity of 50% of mutant EGFR is inhibited) between 500 nM and 2.5 μM; and Compounds 12, 62, 176, 185, 187, 195, 200, 202, 210, 223, 226, 227, 236, 240, and 243 showed IC$_{50}$ values between 10 nM and 499 nM.

Example 12

In Vivo Anticancer Activity

In vivo efficacy of the compounds of this invention was assessed using lung cancer xenograft mice (injected with HCC827), as described in Cancer Research 2004, 64, 4621-4628.

HCC827 cells were injected via s.c. in nude mice to form lung cancer xenograft mice. Mice bearing tumor with a size of ~100 mm$^3$ were randomly assigned to two groups: a vehicle control group (10 mice), and a treatment group (21 mice). Of the treated mice, 21 received Compound 62 at a daily dosage of 5 mg/kg and 15 mg/kg via IV injection through the tail veins for 5 days/week for 2 consecutive weeks (days 1-5 and 8-12).

Unexpected, at the dosage of 5 and 15 mg/kg, Compound 62 suppressed tumor growth significantly (p<0.05), indicating its potent in vivo anti-cancer activity. Upon treatment with this compound, the tumor size was 39% (5 mg/kg) or 23% (15 mg/kg) of that of the vehicle controls at the end of the observation period on the 22nd day post treatment.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

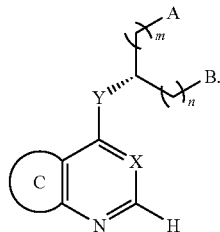

Wherein the compound is a furo[2,3-d]pyrimidine compound

X is N;
Y is O, S, or $NR_2$, in which $R_2$ is H, alkyl, alkenyl, alkynyl, aryl, heteroaryl, cycloalkyl, cycloalkenyl, heterocycloalkyl, or heterocycloalkenyl;
A is alkyl, alkenyl, alkynyl, aryl, heteroaryl, cycloalkyl, cycloalkenyl, heterocycloalkyl, heterocycloalkenyl, halo, cyano, nitro, $OR_3$, $OC(O)R_3$, $C(O)R_3$, $C(O)OR_3$, $C(O)NR_3R_4$, $NR_3R_4$, $NHC(O)R_3$, $NHC(O)NR_3R_4$, $NHC(S)R_3$, $NHC(O)OR_3$, $SO_2R_3$, $SO_3R_3$, or $SO_2NR_3R_4$, in which each of $R_3$ and $R_4$, independently, is H, alkyl, alkenyl, alkynyl, silyl, aryl, heteroaryl, cycloalkyl, cycloalkenyl, heterocycloalkyl, or heterocycloalkenyl, $R_3$ and $R_4$ are optionally substituted, or $R_3$ and $R_4$, together with the nitrogen atoms to which they are bonded, are heterocycloalkyl, heterocycloalkenyl, or heteroaryl;
B is aryl or heteroaryl;
each of m and n, independently, is 0, 1, or 2; and
ring C is

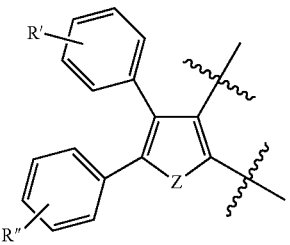

or

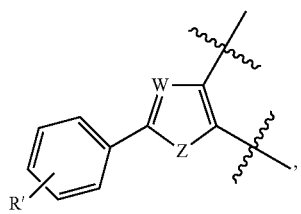

in which
R", is H, alkyl, alkenyl, alkynyl, aryl, heteroaryl, cycloalkyl, cycloalkenyl, heterocycloalkyl, heterocycloalkenyl, halo, nitro, cyano, $OR_a$, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$, in which each of $R_a$ and $R_b$, independently, is H, alkyl, alkenyl, alkynyl, aryl, heteroaryl, cycloalkyl, cycloalkenyl, heterocycloalkyl, or heterocycloalkenyl, $R_a$ and $R_b$ are optionally substituted, or $R_a$ and $R_b$, together with the nitrogen atoms to which they are bonded, are heterocycloalkyl, heterocycloalkenyl, or heteroaryl, R' is $NR_bC(O)R_a$, $R_{a'}$ being

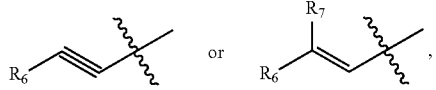

in which $R_6$ is H, alkyl, alkenyl, alkynyl, aryl, heteroaryl, cycloalkyl, cycloalkenyl, heterocycloalkyl, heterocycloalkenyl, $C(O)R_c$, $C(O)OR_c$, $C(O)NR_cR_d$, or $CH_2NR_cR_d$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl, or $R_c$ and $R_d$, together with the nitrogen atoms to which they are bonded, are heterocycloalkyl, heterocycloalkenyl, or heteroaryl, and $R_7$ is H, alkyl, alkenyl, alkynyl, aryl, heteroaryl, cycloalkyl, cycloalkenyl, heterocycloalkyl, or heterocycloalkenyl;

Z is O, and W is $CR_5$, in which $R_5$ is alkenyl, alkynyl, aryl substituted with $OR_a$, or $NR_bC(O)R_a$, heteroaryl, cycloalkyl, cycloalkenyl, heterocycloalkyl, heterocycloalkenyl, halo, nitro, $C(O)OR_a$, $C(O)NR_aR_b$, $NR_bC(O)R_a$, $NHC(O)NR_aR_b$, $NR_bC(S)R_a$, $NHSO_2R_a$, or $NR_aR_b$.

2. The compound of claim 1, wherein the compound is of formula (II):

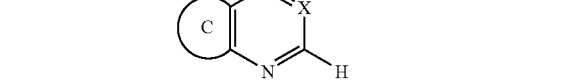

3. The compound of claim 1, wherein B is phenyl and n is 0.

4. The compound of claim 3, wherein m is 1 and A is $OR_3$, $R_3$ being H, aryl, heteroaryl, or $C_{1-3}$ alkyl optionally substituted with aryl or heteroaryl.

5. The compound of claim 4, wherein X is N, Y is NH, and Z is O.

6. The compound of claim 2, wherein B is phenyl and n is 0.

7. The compound of claim 6, wherein A is $C(O)OR_3$ and m is 0.

8. The compound of claim 7, wherein X is N, Y is NH, and Z is O.

9. The compound of claim 8, wherein W is $CR_5$, in which $R_5$ is halo.

10. The compound of claim 6, wherein and R" is OR$_a$.

11. The compound of claim 10, wherein m is 1 and A is OR$_3$, R$_3$ being H, aryl, heteroaryl, or C$_{1-3}$ alkyl optionally substituted with aryl or heteroaryl.

12. The compound of claim 11, wherein X is N, Y is NH, and Z is O.

13. The compound of claim 2, wherein the compound is one of the following compounds:

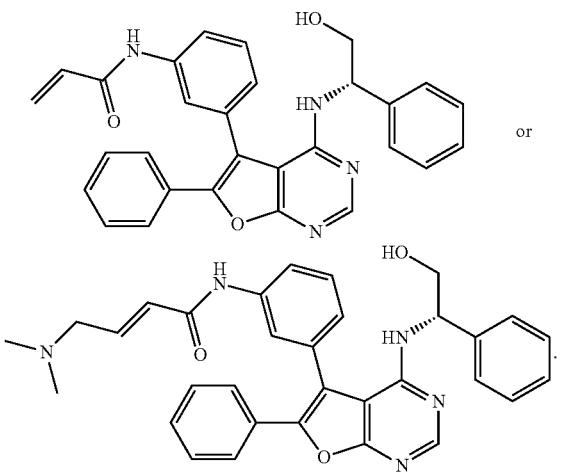

or

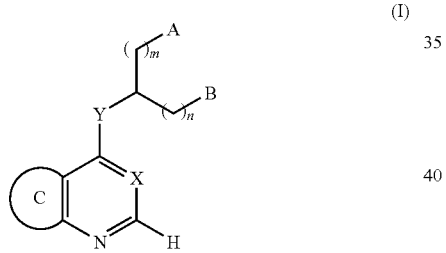

14. A compound of formula (I):

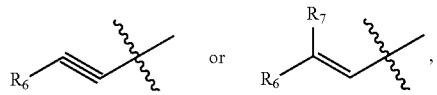

(I)

wherein the compound is a furo[2,3-d]pyrimidine compound

X is N;

Y is O, S, or NR$_2$, in which R$_2$ is H, alkyl, alkenyl, alkynyl, aryl, heteroaryl, cycloalkyl, cycloalkenyl, heterocycloalkyl, or heterocycloalkenyl;

A is alkenyl, alkynyl, aryl, heteroaryl, cycloalkyl, cycloalkenyl, heterocycloalkyl, heterocycloalkenyl, halo, cyano, nitro, OR$_3$, OC(O)R$_3$, C(O)R$_3$, C(O)OR$_3$, C(O)NR$_3$R$_4$, NR$_3$R$_4$, NHC(O)R$_3$, NHC(O)NR$_3$R$_4$, NHC(S)R$_3$, NHC(O)OR$_3$, SO$_2$R$_3$, SO$_3$R$_3$, or SO$_2$NR$_3$R$_4$, in which each of R$_3$ and R$_4$, independently, is H, alkyl, alkenyl, alkynyl, silyl, aryl, heteroaryl, cycloalkyl, cycloalkenyl, heterocycloalkyl, or heterocycloalkenyl, R$_3$ and R$_4$ are optionally substituted, or R$_3$ and R$_4$, together with the nitrogen atoms to which they are bonded, are heterocycloalkyl, heterocycloalkenyl, or heteroaryl;

B is aryl or heteroaryl;

each of m and n, independently, is 0, 1, or 2; and ring C is

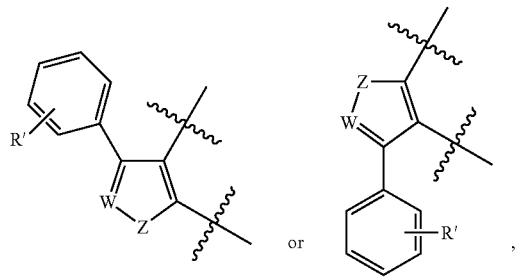

in which

R' is NR$_b$C(O)R$_{a'}$, R$_{a'}$ being

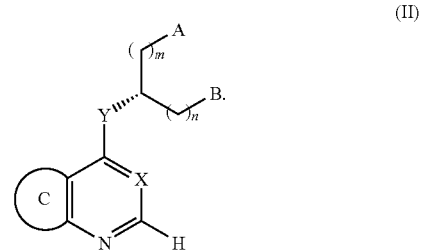

in which R$_6$ is H, alkyl, alkenyl, alkynyl, aryl, heteroaryl, cycloalkyl, cycloalkenyl, heterocycloalkyl, heterocycloalkenyl, C(O)R$_c$, C(O)OR$_c$, C(O)NR$_c$R$_d$, or CH$_2$NR$_c$R$_d$, in which each of R$_c$ and R$_d$, independently, is H, alkyl, alkenyl, alkynyl, aryl, heteroaryl, cycloalkyl, cycloalkenyl, heterocycloalkyl, or heterocycloalkenyl, or R$_c$ and R$_d$, together with the nitrogen atoms to which they are bonded, are heterocycloalkyl, heterocycloalkenyl, or heteroaryl, and R$_7$ is H, alkyl, alkenyl, alkynyl, aryl, heteroaryl, cycloalkyl, cycloalkenyl, heterocycloalkyl, or heterocycloalkenyl, in which R$_b$ is H, alkyl, alkenyl, alkynyl, aryl, heteroaryl, cycloalkyl, cycloalkenyl, heterocycloalkyl, or heterocycloalkenyl, Z is O, and W is CR$_5$, in which R$_5$ is H, alkyl, alkenyl, alkynyl, aryl, heteroaryl, cycloalkyl, cycloalkenyl, heterocycloalkyl, heterocycloalkenyl, halo, nitro, C(O)OR$_a$, C(O)NR$_a$R$_b$, NR$_b$C(O)R$_a$, NHC(O)NR$_a$R$_b$, NR$_b$C(S)R$_a$, NHSO$_2$R$_a$, or NR$_a$R$_b$, in which each of R$_a$ and R$_b$, independently, is H, alkyl, alkenyl, alkynyl, aryl, heteroaryl, cycloalkyl, cycloalkenyl, heterocycloalkyl, or heterocycloalkenyl, R$_a$ and R$_b$ are optionally substituted, or R$_a$ and R$_b$, together with the nitrogen atoms to which they are bonded, are heterocycloalkyl, heterocycloalkenyl, or heteroaryl.

15. The compound of claim 14, wherein the compound is of formula (II):

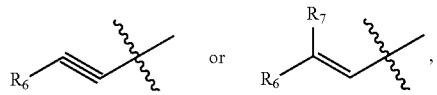

(II)

16. The compound of claim 15, wherein m is 1 and A is OR$_3$, R$_3$ being H, aryl, heteroaryl, or C$_{1-3}$ alkyl optionally substituted with aryl or heteroaryl.

17. The compound of claim 15, wherein the compound is one of the following compounds:
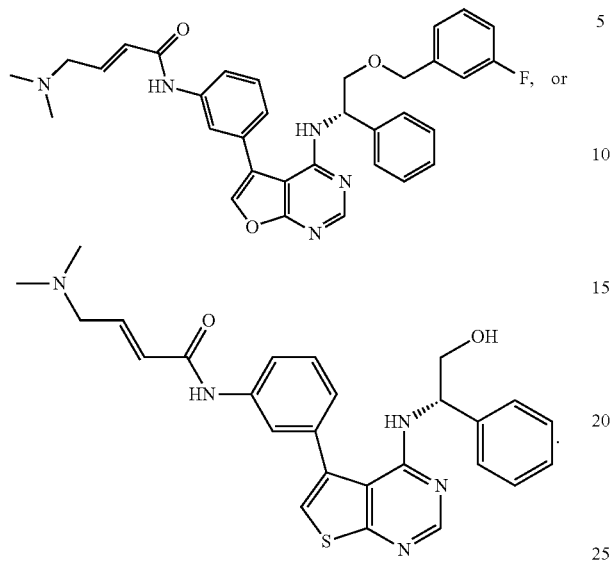
18. A pharmaceutical composition, comprising a compound of claim 2 and a pharmaceutically acceptable carrier.
19. A pharmaceutical composition, comprising a compound of claim 15 and a pharmaceutically acceptable carrier.
* * * * *